US009809637B2

(12) United States Patent
Kumar et al.

(10) Patent No.: US 9,809,637 B2
(45) Date of Patent: Nov. 7, 2017

(54) TRANSFORMING GROWTH FACTOR BETA RECEPTOR II FUSION POLYPEPTIDES

(71) Applicant: Acceleron Pharma Inc., Cambridge, MA (US)

(72) Inventors: Ravindra Kumar, Acton, MA (US); Asya Grinberg, Lexington, MA (US); Dianne S. Sako, Medford, MA (US); Roselyne Castonguay, Malden, MA (US); Rita Steeves, Stoneham, MA (US)

(73) Assignee: ACCLERON PHARMA INC., Cambridge, MA (US)

( * ) Notice: Subject to any disclaimer, the term of this patent is extended or adjusted under 35 U.S.C. 154(b) by 0 days.

(21) Appl. No.: 15/044,883

(22) Filed: Feb. 16, 2016

(65) Prior Publication Data

US 2016/0376341 A1    Dec. 29, 2016

Related U.S. Application Data

(63) Continuation of application No. 14/465,182, filed on Aug. 21, 2014, now abandoned.

(60) Provisional application No. 61/906,849, filed on Nov. 20, 2013, provisional application No. 61/906,270, filed on Nov. 19, 2013, provisional application No. 61/868,713, filed on Aug. 22, 2013.

(51) Int. Cl.
*C07K 14/71* (2006.01)
*C07K 14/495* (2006.01)
*C07K 16/22* (2006.01)
*A61K 38/00* (2006.01)

(52) U.S. Cl.
CPC ............ *C07K 14/71* (2013.01); *C07K 14/495* (2013.01); *C07K 16/22* (2013.01); *A61K 38/00* (2013.01); *C07K 2317/76* (2013.01); *C07K 2319/30* (2013.01); *C07K 2319/31* (2013.01)

(58) Field of Classification Search
CPC ...... C07K 14/495; C07K 14/71; C07K 16/22; C07K 2317/76; C07K 2319/30; C07K 2319/31; A61K 38/00
See application file for complete search history.

(56) References Cited

U.S. PATENT DOCUMENTS

| | | |
|---|---|---|
| 5,543,143 A | 8/1996 | Reed |
| 5,571,714 A | 11/1996 | Dasch et al. |
| 5,662,904 A | 9/1997 | Ferguson et al. |
| 5,693,607 A * | 12/1997 | Segarini ................ C07K 14/71 435/69.1 |
| 5,772,998 A | 6/1998 | Dasch et al. |
| 5,783,185 A | 7/1998 | Dasch et al. |
| 5,844,099 A | 12/1998 | Stahl et al. |
| 6,001,969 A | 12/1999 | Lin et al. |
| 6,008,011 A | 12/1999 | Lin et al. |
| 6,046,157 A | 4/2000 | Lin et al. |
| 6,090,383 A | 7/2000 | Dasch et al. |
| 6,294,350 B1 | 9/2001 | Peterson |
| 6,419,928 B1 | 7/2002 | Dasch et al. |
| 6,630,326 B2 | 10/2003 | Markowitz et al. |
| 6,998,125 B2 | 2/2006 | Hanna et al. |
| 7,786,261 B2 | 8/2010 | De Crescenzo et al. |
| 7,795,389 B2 | 9/2010 | Sun et al. |
| 7,867,496 B2 | 1/2011 | Khanna et al. |
| 8,067,389 B2 | 11/2011 | Kumar et al. |
| 8,283,449 B2 | 10/2012 | Galipeau et al. |
| 8,318,135 B2 | 11/2012 | O'Connor-McCourt et al. |
| 8,591,901 B2 | 11/2013 | Ledbetter et al. |
| 8,658,135 B2 | 2/2014 | O'Connor-McCourt et al. |
| 2002/0004037 A1 | 1/2002 | Koteliansky et al. |
| 2004/0192583 A1 | 9/2004 | Medicherla et al. |
| 2004/0234967 A1 | 11/2004 | Moskowitz |
| 2005/0148555 A1 | 7/2005 | Gupta et al. |
| 2005/0203022 A1 | 9/2005 | Gotwals et al. |
| 2006/0286105 A1 | 12/2006 | Ledbetter et al. |
| 2008/0261879 A1 | 10/2008 | Melton et al. |
| 2009/0004182 A1 | 1/2009 | Baiocchi et al. |
| 2009/0036382 A1 | 2/2009 | Bressan et al. |
| 2009/0042780 A1 | 2/2009 | Knopf et al. |
| 2010/0003256 A1 | 1/2010 | Lu et al. |
| 2010/0008911 A1 | 1/2010 | Streisand et al. |
| 2010/0204104 A1 | 8/2010 | Qiu et al. |
| 2011/0008364 A1 | 1/2011 | Ledbetter et al. |
| 2011/0104121 A1 | 5/2011 | Wira et al. |
| 2011/0177070 A1 | 7/2011 | Lofquist et al. |
| 2011/0236309 A1 | 9/2011 | O'Connor-Mccourt et al. |
| 2011/0245107 A1 | 10/2011 | Kuchroo et al. |
| 2012/0010178 A1 | 1/2012 | Rubin et al. |
| 2012/0114640 A1 | 5/2012 | Kulkarni et al. |
| 2013/0011397 A1 | 1/2013 | Pasricha |
| 2013/0039911 A1 | 2/2013 | Bedi et al. |
| 2013/0045272 A1 | 2/2013 | Niitsu et al. |
| 2015/0056199 A1 | 2/2015 | Kumar et al. |
| 2015/0080320 A1 | 3/2015 | Desai |
| 2015/0225483 A1 | 8/2015 | Lo |
| 2016/0017026 A1 | 1/2016 | Wei et al. |
| 2016/0298093 A1 | 10/2016 | Kumar et al. |

FOREIGN PATENT DOCUMENTS

| | | |
|---|---|---|
| CN | 101852804 A | 10/2010 |
| EP | 0 975 771 B1 | 2/2000 |

(Continued)

OTHER PUBLICATIONS

Zwaagstra JC et al. Molecular Cancer Therapeutics. 11(7):1477-1487. Jul. 2012. Available online at—doi:10.1158/1535-7163.MCT-12-0060.*

(Continued)

*Primary Examiner* — Robert Landsman
(74) *Attorney, Agent, or Firm* — White & Case LLP

(57) ABSTRACT

In certain aspects, the present disclosure relates to polypeptides comprising a truncated, ligand-binding portion of the extracellular domain of TβRII polypeptide useful to selectively antagonize a TβRII ligand. The disclosure further provides compositions and methods for use in treating or preventing TGFβ associated disorders.

9 Claims, 7 Drawing Sheets

(56) References Cited

FOREIGN PATENT DOCUMENTS

| WO | WO-91/19513 A1 | 12/1991 |
|---|---|---|
| WO | WO 98/48024 A1 | 10/1998 |
| WO | WO 99/65948 A1 | 12/1999 |
| WO | WO-01/66140 A1 | 9/2001 |
| WO | WO 03/011908 A2 | 2/2003 |
| WO | WO-03/061587 A2 | 7/2003 |
| WO | WO-2004/098637 A1 | 11/2004 |
| WO | WO 2005/019258 A2 | 3/2005 |
| WO | WO-2006/036729 A2 | 4/2006 |
| WO | WO-2008/060371 A1 | 5/2008 |
| WO | WO 2008/157367 A1 | 12/2008 |
| WO | WO-2008/157367 A1 | 12/2008 |
| WO | WO 2010/003118 A1 | 1/2010 |
| WO | WO 2011/109789 A2 | 11/2011 |
| WO | WO-2012/030394 A1 | 3/2012 |
| WO | WO 2013/000234 A1 | 1/2013 |
| WO | WO 2013/012648 A1 | 1/2013 |
| WO | WO 2013/164694 A1 | 11/2013 |
| WO | WO 2014/172584 A1 | 10/2014 |

OTHER PUBLICATIONS

Agarwal et al., "Bone marrow fibrosis in primary myelofibrosis: pathogenic mechanisms and the role of Tgf-beta," Stem Cell Investigation. vol. 3(5): 1-10. (General Review) (2016).

Akhurst et al., "Targeting the TGF beta signalling pathway in disease," Nature Review Drug Discovery. vol. 11(10): 790-810 (2012).

Chagraoui et al., "Prominent role of TGF-beta 1 in thrombopoietin-induced myelofibrosis in mice," Blood, vol. 100(10): 3495-3503 (2002).

del Re et al., "In the absence of type III receptor, the transorming growth factor (TGF)-beta type II-B receptor requires the type I receptor to bind TGF-beta2," J Biol Chem, vol. 279(21): 22765-22772 (2004).

Dennler et al, "Direct binding of Smad3 and Smad4 to critical TGF beta-inducible elements in the promoter of human plasminogen activator inhibitor-type 1 gene," EMBO, vol. 17(11): 3091-3100 (1998).

Gastinne et al., "Adenoviral-mediated TGF-beta1 inhibition in a mouse model of myelofibrosis inhibit bone marrow fibrosis development," Experimental Hematology, vol. 35, Issue 1: 64-74 (2007).

Grobet et al., "A deletion in the bovine myostatin gene causes the double-muscled phenotype in cattle," Nat Genet, vol. 17(1): 71-74 (1997).

Harrison et al., "Prodomains regulate the synthesis, extracellular localisation and activity of TGF-beta superfamily ligands," Growth Factors, vol. 29(5): 174-186 (2011).

Hirai and Fijita, "A Human Transforming Growth Factor-beta Type II Receptor that Contains an Insertion in the Extracellular Domain," Ex. Cell Res., vol. 223 135-141 (1996).

Isaka et al., "Gene therapy by transforming growth factor-beta receptor-IgG Fc chimera suppressed extracellular matrix accumulation in experimental glomerulonephritis," Kidney International, vol. 55(2): 467-475 (1999).

Komesli et al., "Chimeric extracellular domain of type II transforming growth factor (TGF)-beta receptor fused to the Fc region of human immunoglobulin as a TGF-beta antagonist," Eur. J. Biochem., vol. 254: 505-513 (1998).

Konrad et al., "Alternative splicing of TGF-betas and their high-affinity receptors T beta RI, T beta RII and T beta RIII (betaglycan) reveal new variants in human prostatic cells," BMC Genomics, vol. 8: 318 (2007).

Lin et al. "Expression cloning of the TGF-beta type II receptor, a functional transmembrane serine/threonine kinase," Cell, vol. 68(4): 775-785 (1992).

Mascarenhas et al., "Anti-transforming growth factor-beta therapy in patients with myelofibrosis," Leukemia & Lymphoma. vol. 55(2): 450-452 (2014).

Massagué, J., "How cells read TGF-beta signals," Nat. Rev. Mol. Cell Biol. 1(3): 169-178 (2000).

Nikawa, Jun-ichi. "A cDNA encoding the human transforming growth factor beta receptor suppresses the growth defect of yeast mutant," Gene, vol. 149: 367-372 (1994).

R&D Systems, Recombinant Human TGF-β RBII Fc Chimera , Catalog No. 341-BR (2015).

R&D Systems, Recombinant Human TGF-βRI Isoform 2 Fc Chimera Catalog No. 1003-RT (2015).

Radaev et al., "Ternary complex and transforming factor-beta1 reveals isoform-specific ligand recognition and receptor recruitment in the superfamily, " J Biol Chem, vol. 285(19):14806-14814 (2010).

Rotzer et al., "Type III TGF-beta receptor-independent signaling of TGFB2 via TBRII-B, an alternatively spliced TGF-B type II receptor," The EMBO Journal, vol. 20(3): 480-490 (2001).

Schuelke et al., "Myostatin mutation associated with gross muscle hypertrophy in a child," N Engl J Med vol. 350(26): 2682-26888 (2004).

Shi et al., "Latent TGF-beta structure and activation," Nature, vol. 474(7351): 343-349 (2011).

Suzuki et al., "Cloning of an isoform of mouse TGF-beta type II receptor gene," FEBS Letters, vol. 335: 19-22 (1994).

Yan et al., "A Model of Myelofibrosis and Osterosclerosis in Mice Induced by Overexpressing Thrombopoietin (mpl Ligand): Reversal of Disease by Bone Marrow Transplantation," Blood, vol. 88(2): 402-409 (1996).

Vannucchi et al., "A pathobiologic pathway linking thrombopoietin, GATA-1, and TGF-beta1 in the development of myelofibrosis," Blood, vol. 105(9): 3493-3501 (2005).

Wrana et al., "TGF beta signals through a heteromeric protein kinase receptor complex," Cell vol. 71(6): 1003-1014 (1992).

Xing et al., "Transgenic expression of $JAK2^{V617F}$ causes myeloproliferative disorders in mice," vol. 111(10): 5109-5117 (2008).

Zahr et al., "Bone marrow fibrosis in myelofibrosis: pathogenesis, prognosis and targeted strategies," Haematologica, vol. 101(6): 660-671 (2016).

Zauli et al., "Reduced responsiveness of bone marrow megakaryocyte progenitors to platelet-derived transforming growth factor beta 1, produced in normal amount, in patients with essential thromboycythamia," Br J Haematol, vol. 83(1): 14-20 (1993).

Yan et al., "A Model of Myelofibrosis and Osterosclerosis in Mice Induced by Overexpressing Thrombopoietin (mpl Ligand): Reversal of Disease by Bone Marrow Transplantation," Blood, vol. 88(2) 402-409 (1996).

Kontani et al., "Spontaneous elicitation of potent antitumor immunity and eradication of established tumors by administration of DNA encoding soluble transforming growth factor-[beta] II receptor without active antigen-sensitization," Cancer Immunol. Immunotherapy; vol. 55: 579-487 (2006).

Xin et al., "Suppression of Cyclosporine a Nephrotoxicity in Vivo by Transforming Growth Factor beta Receptor-Immunoglobulin G Chimeric Protein," Transplantation, vol. 77(9): 1433-1442 (2004).

Zwaagstra et al., "Engineering and Therapeutic Application of Single-Chain Bivalent TGF-[beta] Family Traps," Molecular Cancer Therapeutics, vol. 11(7): 1477-1487 (2012).

* cited by examiner

|     |            |            |            |            |            |
|-----|------------|------------|------------|------------|------------|
| 1   | MPGQELRTVN | GSQMLLVLLV | LSWLPHGGAL | SLAEASRASF | PGPSELHSED |
| 51  | SRFRELRKRY | EDLLTRLRAN | QSWEDSNTDL | VPAPAVRILT | PEVRLGSGGH |
| 101 | LHLRISRAAL | PEGLPEASRL | HRALFRLSPT | ASRSWDVTRP | LRRQLSLARP |
| 151 | QAPALHLRLS | PPPSQSDQLL | AESSSARPQL | ELHLRPQAAR | GRRRARARNG |
| 201 | DHCPLGPGRC | CRLHTVRASL | EDLGWADWVL | SPREVQVTMC | IGACPSQFRA |
| 251 | ANMHAQIKTS | LHRLKPDTVP | APCCVPASYN | PMVLIQKTDT | GVSLQTYDDL |
| 301 | LAKDCHCI   | (SEQ ID NO: 1) |        |            |            |

FIGURE 1

```
  1  ATGCCCGGGC AAGAACTCAG GACGGTGAAT GGCTCTCAGA TGCTCCTGGT
 51  GTTGCTGGTG CTCTCGTGGC TGCCGCATGG GGGCGCCCTG TCTCTGGCCG
101  AGGCGAGCCG CGCAAGTTTC CCGGGACCCT CAGAGTTGCA CTCCGAAGAC
151  TCCAGATTCC GAGAGTTGCG GAAACGCTAC GAGGACCTGC TAACCAGGCT
201  GCGGGCCAAC CAGAGCTGGG AAGATTCGAA CACCGACCTC GTCCCGGCCC
251  CTGCAGTCCG GATACTCACG CCAGAAGTGC GGCTGGGATC CGGCGGCCAC
301  CTGCACCTGC GTATCTCTCG GGCCGCCCTT CCCGAGGGGC TCCCCGAGGC
351  CTCCCGCCTT CACCGGGCTC TGTTCCGGCT GTCCCCGACG GCGTCAAGGT
401  CGTGGGACGT GACACGACCG CTGCGGCGTC AGCTCAGCCT TGCAAGACCC
451  CAGGCACCCG CGCTGCACCT GCGACTGTCG CCGCCGCCGT CGCAGTCGGA
501  CCAACTGCTG GCAGAATCTT CGTCCGCACG GCCCCAGCTG GAGTTGCACT
551  TGCGGCCGCA AGCCGCCAGG GGGCGCCGCA GAGCGCGTGC GCGCAACGGG
601  GACCACTGTC CGCTCGGGCC CGGGCGTTGC TGCCGTCTGC ACACGGTCCG
651  CGCGTCGCTG GAAGACCTGG GCTGGGCCGA TTGGGTGCTG TCGCCACGGG
701  AGGTGCAAGT GACCATGTGC ATCGGCGCGT GCCCGAGCCA GTTCCGGGCG
751  GCAAACATGC ACGCGCAGAT CAAGACGAGC CTGCACCGCC TGAAGCCCGA
801  CACGGTGCCA GCGCCCTGCT GCGTGCCCGC CAGCTACAAT CCCATGGTGC
851  TCATTCAAAA GACCGACACC GGGGTGTCAC TCCAGACCTA TGATGACTTG
901  TTAGCCAAAG ACTGCCACTG CATA          (SEQ ID NO: 2)
```

FIGURE 2

```
  1  MAPPALQAQP  PGGSQLRFLL  FLLLLLLLLS  WPSQGDALAM  PEQRPSGPES
 51  QLNADELRGR  FQDLLSRLHA  NQSREDSNSE  PSPDPAVRIL  SPEVRLGSHG
101  QLLLRVNRAS  LSQGLPEAYR  VHRALLLLTP  TARPWDITRP  LKRALSLRGP
151  RAPALRLRLT  PPPDLAMLPS  GGTQLELRLR  VAAGRGRRSA  HAHPRDSCPL
201  GPGRCCHLET  VQATLEDLGW  SDWVLSPRQL  QLSMCVGECP  HLYRSANTHA
251  QIKARLHGLQ  PDKVPAPCCV  PSSYTPVVLM  HRTDSGVSLQ  TYDDLVARGC
301  HCA         (SEQ ID NO: 3)
```

FIGURE 3

```
  1  ATGGCCCCGC CCGCGCTCCA GGCCCAGCCT CCAGGCGGCT CTCAACTGAG
 51  GTTCCTGCTG TTCCTGCTGC TGTTGCTGCT GCTGCTGTCA TGGCCATCGC
101  AGGGGGACGC CCTGGCAATG CCTGAACAGC GACCCTCCGG CCCTGAGTCC
151  CAACTCAACG CCGACGAGCT ACGGGGTCGC TTCCAGGACC TGCTGAGCCG
201  GCTGCATGCC AACCAGAGCC GAGAGGACTC GAACTCAGAA CCAAGTCCTG
251  ACCCAGCTGT CCGGATACTC AGTCCAGAGG TGAGATTGGG GTCCCACGGC
301  CAGCTGCTAC TCCGCGTCAA CCGGGCGTCG CTGAGTCAGG GTCTCCCCGA
351  AGCCTACCGC GTGCACCGAG CGCTGCTCCT GCTGACGCCG ACGGCCCGCC
401  CCTGGGACAT CACTAGGCCC CTGAAGCGTG CGCTCAGCCT CCGGGGACCC
451  CGTGCTCCCG CATTACGCCT GCGCCTGACG CCGCCTCCGG ACCTGGCTAT
501  GCTGCCCTCT GGCGGCACGC AGCTGGAACT GCGCTTACGG GTAGCCGCCG
551  GCAGGGGGCG CCGAAGCGCG CATGCGCACC AAGAGACTC GTGCCCACTG
601  GGTCCAGGGC GCTGCTGTCA CTTGGAGACT GTGCAGGCAA CTCTTGAAGA
651  CTTGGGCTGG AGCGACTGGG TGCTGTCCCC GCGCCAGCTG CAGCTGAGCA
701  TGTGCGTGGG CGAGTGTCCC CACCTGTATC GCTCCGCGAA CACGCATGCG
751  CAGATCAAAG CACGCCTGCA TGGCCTGCAG CCTGACAAGG TGCCTGCCCC
801  GTGCTGTGTC CCCTCCAGCT ACACCCCGGT GGTTCTTATG CACAGGACAG
851  ACAGTGGTGT GTCACTGCAG ACTTATGATG ACCTGGTGGC CCGGGGCTGC
901  CACTGCGCT           (SEQ ID NO: 4)
```

FIGURE 4

|     |            |            |            |            |            |
| --- | ---------- | ---------- | ---------- | ---------- | ---------- |
| 1   | mgrgllrqlw | plhivlwtri | astipphvqk | svnndmivtd | nngavkfpql |
| 51  | ckfcdvrfst | cdnqkscmsn | csitsicekp | qevcvavwrk | ndenitletv |
| 101 | chdpklpyhd | filedaaspk | cimkekkkpg | etffmcscss | decndniifs |
| 151 | eeyntsnpdl | llvifqvtgi | sllpplgvai | sviiifycyr | vnrqqklsst |
| 201 | wetgktrklm | efsehcaiil | eddrsdisst | canninhnte | llpieldtlv |
| 251 | gkgrfaevyk | aklkqntseq | fetvavkifp | yeeyaswkte | kdifsdinlk |
| 301 | henilqflta | eerktelgkq | ywlitafhak | gnlqeyltrh | viswedlrkl |
| 351 | gsslargiah | lhsdhtpcgr | pkmpivhrdl | kssnilvknd | ltcclcdfgl |
| 401 | slrldptlsv | ddlansgqvg | tarymapevl | esrmnlenve | sfkqtdvysm |
| 451 | alvlwemtsr | cnavgevkdy | eppfgskvre | hpcvesmkdn | vlrdrgrpei |
| 501 | psfwlnhqgi | qmvcetltec | wdhdpearlt | aqcvaerfse | lehldrlsgr |
| 551 | scseekiped | gslnttk    |            | (SEQ ID NO: 5) | |

FIGURE 5

```
  1  mgrgllrglw plhivlwtri astipphvqk sdvemeaqkd eiicpscnrt
 51  ahplrhinnd mivtdnngav kfpqlckfcd vrfstcdnqk scmsncsits
101  icekpqevcv avwrkndeni tletvchdpk lpyhdfiled aaspkcimke
151  kkkpgetffm cscssdecnd niifseeynt snpdlllvif qvtgisllpp
201  lgvaisviii fycyrvnrqq klsstwetgk trklmefseh caiileddrs
251  disstcanni nhntellpie ldtlvgkgrf aevykaklkq ntseqfetva
301  vkifpyeeya swktekdifs dinlkhenil qfltaeerkt elgkqywlit
351  afhakgnlqe yltrhviswe dlrklgssla rgiahlhsdh tpcgrpkmpi
401  vhrdlkssni lvkndltccl cdfglslrld ptlsvddlan sgqvgtarym
451  apevlesrmn lenvesfkqt dvysmalvlw emtsrcnavg evkdyeppfg
501  skvrehpcve smkdnvlrdr grpeipsfwl nhqgiqmvce tltecwdhdp
551  earltaqcva erfselehld rlsgrscsee kipedgslnt tk
     (SEQ ID NO: 6)
```

FIGURE 6

```
                          Native Leader Sequence                    Splice Insertion (25 aa)

1         10        20         30                                    35
Native TβRII short        MGRGLLRGLWPLHIVLWTRIAS TIPPHVQKS------------------------VNNDMIV...

30                                    35
TβRII_short(23-X)                                          TIPPHVQKS------------------------VNNDMIV...

30                          35
TβRII_short(29-X)                                                    QKS------------------------VNNDMIV...

35
TβRII_short(35-X)                                                                                DMIV...

1         10        20         30        40        50        60
Native TβRII long         MGRGLLRGLWPLHIVLWTRIAS TIPPHVQKSDVEMEAQKDEIICPSCNRTAHPLRHINNDMIV...

30        40        50        60
TβRII_long(23-X)                                           TIPPHVQKSDVEMEAQKDEIICPSCNRTAHPLRHINNDMIV...

30        40        50        60
TβRII_long(29-X)                                                     QKSDVEMEAQKDEIICPSCNRTAHPLRHINNDMIV...

60
TβRII_long(60-X)                                                                                 DMIV...
```

FIGURE 7

TRANSFORMING GROWTH FACTOR BETA RECEPTOR II FUSION POLYPEPTIDES

RELATED APPLICATIONS

This application is a continuation of U.S. patent application Ser. No. 14/465,182 (now abandoned), filed Aug. 21, 2014, which claims the benefit of priority to U.S. Provisional Application Ser. No. 61/906,849, filed Nov. 20, 2013, 61/906,270, filed Nov. 19, 2013, and 61/868,713, filed Aug. 22, 2013. The specifications of each of the foregoing applications are hereby incorporated by reference in their entirety.

SEQUENCE LISTING

The instant application contains a Sequence Listing which has been submitted via EFS-Web and is hereby incorporated by reference in its entirety. Said ASCII copy, created on Feb. 16, 2016, is named PHPH071102_Seq.txt, and is 138,755 bytes in size.

BACKGROUND OF THE INVENTION

Members of the transforming growth factor-beta (TGFβ) superfamily are pleiotropic cytokines involved in essential cellular functions such as proliferation, differentiation, apoptosis, motility, extracellular matrix production, tissue remodeling, angiogenesis, immune response, cell adhesion, and also play a key role in pathophysiology of disease states as different as chronic inflammatory conditions and cancer. Members of the TGFβ superfamily have been classified into major family groupings, which include TGFβs, bone morphogenetic proteins (BMP), osteogenic proteins (OP), growth and differentiation factors (GDF), inhibins/activins, mullerian inhibitory substances (MIS) and glial derived neurotrophic factors (GDNF).

TGFβ superfamily members transduce their signals across the plasma membrane by inducing the formation of heteromeric complexes of specific type I and type II serine/threonine kinase receptors, which in turn activate a particular subset of SMAD proteins (some inhibitory and some excitatory). The SMAD molecule compounds relay the signals into the nucleus where they direct transcriptional responses in concert with other proteins.

Dysfunctional TGFβ superfamily signaling has been linked to several clinical disorders including cancer, fibrosis, bone diseases, diabetic nephropathy, as well as chronic vascular diseases such as atherosclerosis.

Thus, it is an object of the present disclosure to provide compositions and methods for modulating TGFβ superfamily signaling.

SUMMARY OF THE INVENTION

In part, the disclosure provides TβRII polypeptides and the use of such TβRII polypeptides as selective antagonists for GDF15, TGFβ1 or TGFβ3. As described herein, polypeptides comprising part or all of the TβRII extracellular domain (ECD), with or without additional mutations, bind to and/or inhibit GDF15, TGFβ1 or TGFβ3 with varying affinities. Thus, in certain aspects, the disclosure provides TβRII polypeptides for use in selectively inhibiting TGFβ superfamily associated disorders.

In certain aspects, the disclosure provides polypeptides comprising mutations and/or truncations in the extracellular domain of TβRII. In certain aspects, the disclosure provides a TβRII fusion polypeptide comprising a first amino acid sequence from the extracellular domain of TβRII and a heterologous amino acid sequence, wherein the first amino acid sequence comprises or consists of an amino acid sequence at least 80%, at least 85%, at least 90%, at least 95%, at least 96%, at least 97%, at least 98%, at least 99% identical or identical to a) a sequence beginning at any of positions 23 to 35 of SEQ ID NO: 5 and ending at any of positions 153 to 159 of SEQ ID NO: 5 or b) a sequence beginning at any of positions 23 to 60 of SEQ ID NO: 6 and ending at any of positions 178 to 184 of SEQ ID NO: 6.

In certain aspects the disclosure provides polypeptides comprising a wild-type or altered and/or truncated extracellular domain of TβRII fused to at least a portion of the Fc domain of a human IgG2. Thus in certain aspects, the disclosure provides a TβRII fusion polypeptide comprising a first amino acid sequence from the extracellular domain of TβRII and a heterologous amino acid sequence, wherein the first amino acid sequence comprises or consists of an amino acid sequence at least 80%, at least 85%, at least 90%, at least 95%, at least 96%, at least 97%, at least 98%, at least 99% identical or identical to a) a sequence beginning at any of positions 23 to 35 of SEQ ID NO: 5 and ending at any of positions 153 to 159 of SEQ ID NO: 5 or b) a sequence beginning at any of positions 23 to 60 of SEQ ID NO: 6 and ending at any of positions 178 to 184 of SEQ ID NO: 6, and wherein the polypeptide comprises a second polypeptide sequence that comprises at least a constant domain of a human IgG2 and may optionally comprise or consist of an amino acid sequence that is at least 80%, at least 85%, at least 90%, at least 95%, at least 96%, at least 97%, at least 98%, at least 99% identical to SEQ ID NO: 19, and wherein an linker is optionally positioned between the first polypeptide and the second polypeptide. An example of the is provided as SEQ ID NO:50 and is encoded by the nucleic acid sequence of SEQ ID NO:51. In certain embodiments, the disclosure provides polypeptides with an amino acid sequence that comprises or consists of an amino acid sequence that is at least 80%, 85%, 90%, 95%, 96%, 97%, 98%, 99% or 100% identical to the amino acid sequence of SEQ ID NO:50. In certain embodiments, the disclosure provides polypeptides that are encoded by a nucleic acid sequence that comprises or consists of a nucleic acid sequence that is at least 80%, 85%, 90%, 95%, 96%, 97%, 98%, 99% or 100% identical to the nucleic acid sequence of SEQ ID NO:51.

In some embodiments, the first amino acid sequence comprises or consists of the sequence beginning at position 23 of SEQ ID NO: 5 and ending at position 159 of SEQ ID NO: 5. In some embodiments, the first amino acid sequence comprises or consists of the sequence beginning at position 29 of SEQ ID NO: 5 and ending at position 159 of SEQ ID NO: 5. In some embodiments, the first amino acid sequence comprises or consists of the sequence beginning at position 35 of SEQ ID NO: 5 and ending at position 159 of SEQ ID NO: 5. In some embodiments, the first amino acid sequence comprises or consists of the sequence beginning at position 23 of SEQ ID NO: 5 and ending at position 153 of SEQ ID NO: 5. In some embodiments, the first amino acid sequence comprises or consists of the sequence beginning at position 29 of SEQ ID NO: 5 and ending at position 153 of SEQ ID NO: 5. In some embodiments, the first amino acid sequence comprises or consists of the sequence beginning at position 35 of SEQ ID NO: 5 and ending at position 153 of SEQ ID NO: 5.

In some embodiments, the first amino acid sequence comprises or consists of the sequence beginning at position 23 of SEQ ID NO: 6 and ending at positions 184 of SEQ ID NO: 6. In some embodiments, the first amino acid sequence comprises or consists of the sequence beginning at position 29 of SEQ ID NO: 6 and ending at position 184 of SEQ ID NO: 6. In some embodiments, the first amino acid sequence comprises or consists of the sequence beginning at position 23 of SEQ ID NO: 6 and ending at position 178 of SEQ ID NO: 6. In some embodiments, the first amino acid sequence comprises or consists of the sequence beginning at position 29 of SEQ ID NO: 6 and ending at position 178 of SEQ ID NO: 6.

In some embodiments, the first amino acid sequence comprises or consists of a sequence that has a D at the position corresponding to position 36 of SEQ ID NO: 47 and/or a K at the position corresponding to position 76 of SEQ ID NO: 47.

In certain aspects, the disclosure provides a TβRII fusion polypeptide comprising a first amino acid sequence at least 80%, at least 85%, at least 90%, at least 95%, at least 96%, at least 97%, at least 98%, at least 99% identical or identical to the sequence of SEQ ID NO: 7 or SEQ ID NO: 13, or active fragment thereof, and a second heterologous portion, wherein the first amino acid sequence has a D at the position corresponding to position 36 of SEQ ID NO: 47 and/or a K at the position corresponding to position 76 of SEQ ID NO: 47.

In some embodiments, the first amino acid sequence comprises an N-terminal truncation of 1-12 amino acids corresponding to amino acids 1-12 of SEQ ID NO: 7 or 1-37 amino acids corresponding to amino acids 1-37 of SEQ ID NO: 13. In some embodiments, the first amino acid sequence comprises an N-terminal truncation of 6 amino acids corresponding to amino acids 1-6 of SEQ ID NO: 7 or SEQ ID NO: 13. In some embodiments, the first amino acid sequence comprises an N-terminal truncation of 12 amino acids corresponding to amino acids 1-12 of SEQ ID NO: 7 or 37 amino acids corresponding to amino acids 1-37 of SEQ ID NO: 13. In some embodiments, the first amino acid sequence comprises a C-terminal truncation of 1-6 amino acids corresponding to amino acids 137-132 of SEQ ID NO: 7 or amino acids 162-157 of SEQ ID NO: 13. In some embodiments, the first amino acid sequence comprises a C-terminal truncation of 6 amino acids corresponding to amino acids 132-137 of SEQ ID NO: 7 or amino acids 157-162 of SEQ ID NO: 13. In some embodiments, the first amino acid sequence comprises an insertion corresponding to SEQ ID NO: 18 between the residues corresponding to positions 117 and 118 of SEQ ID NO: 47.

In some embodiments, the heterologous portion comprises one or more polypeptide portions that enhance one or more of: in vivo stability, in vivo half life, uptake/administration, tissue localization or distribution, formation of protein complexes, and/or purification. In some embodiments, the heterologous portion comprises a polypeptide portion selected from: an immunoglobulin Fc domain and a serum albumin. In a further embodiment, the immunoglobulin Fc domain is joined to the TβRII polypeptide by a linker.

In some embodiments, the polypeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. In some embodiments, the polypeptide is glycosylated.

In certain aspects, the disclosure provides a TβRII fusion polypeptide comprising a first amino acid sequence consisting of a portion of the extracellular domain of TβRII that comprises an amino acid sequence that is at least 80%, at least 85%, at least 90%, or at least 95% identical to an amino acid sequence selected from SEQ ID NOs: 7-17 and 47-49, and a second heterologous portion. In certain aspects, the disclosure provides a TβRII fusion polypeptide comprising a first amino acid sequence consisting of a portion of the extracellular domain of TβRII that comprises an amino acid sequence that is at least 96% identical to an amino acid sequence selected from SEQ ID NOs: 7-17 and 47-49, and a second heterologous portion. In certain aspects, the disclosure provides a TβRII fusion polypeptide comprising a first amino acid sequence consisting of a portion of the extracellular domain of TβRII that comprises an amino acid sequence that is at least 97% identical to an amino acid sequence selected from SEQ ID NOs: 7-17 and 47-49, and a second heterologous portion. In certain aspects, the disclosure provides a TβRII fusion polypeptide comprising a first amino acid sequence consisting of a portion of the extracellular domain of TβRII that comprises an amino acid sequence that is at least 98% identical to an amino acid sequence selected from SEQ ID NOs: 7-17 and 47-49, and a second heterologous portion. In certain aspects, the disclosure provides a TβRII fusion polypeptide comprising a first amino acid sequence consisting of a portion of the extracellular domain of TβRII that comprises an amino acid sequence that is at least 99% identical to an amino acid sequence selected from SEQ ID NOs: 7-17 and 47-49, and a second heterologous portion. In certain aspects, the disclosure provides a TβRII fusion polypeptide comprising a first amino acid sequence consisting of a portion of the extracellular domain of TβRII that comprises an amino acid sequence is an amino acid sequence selected from SEQ ID NOs: 7-17 and 47-49 and a second heterologous portion.

In certain aspects, the disclosure provides a polypeptide comprising or consisting of an amino acid sequence that is at least 80%, at least 85%, at least 90%, or at least 95% identical to an amino acid sequence selected from SEQ ID NOs: 25, 27, 29, 31, 33, 35, 37, 39, 41 and 43 or the portion thereof with the leader sequence removed, e.g., a polypeptide comprising or consisting of an amino acid sequence that is at least 80%, at least 85%, at least 90%, or at least 95% identical to an amino acid sequence selected from SEQ ID NOs: 53, 54, 55, 56, 57, 58, 59, 60, 61, and 62. In certain aspects, the disclosure provides a polypeptide comprising or consisting of an amino acid sequence that is at least 96% identical to an amino acid sequence selected from SEQ ID NOs: 25, 27, 29, 31, 33, 35, 37, 39, 41 and 43 or the portion thereof with the leader sequence removed, e.g., a polypeptide comprising or consisting of an amino acid sequence that is at least 96% identical to an amino acid sequence selected from SEQ ID NOs: 53, 54, 55, 56, 57, 58, 59, 60, 61, and 62. In certain aspects, the disclosure provides a polypeptide comprising or consisting of an amino acid sequence that is at least 97% identical to an amino acid sequence selected from SEQ ID NOs: 25, 27, 29, 31, 33, 35, 37, 39, 41 and 43 or the portion thereof with the leader sequence removed, e.g., a polypeptide comprising or consisting of an amino acid sequence that is at least 97% identical to an amino acid sequence selected from SEQ ID NOs: 53, 54, 55, 56, 57, 58, 59, 60, 61, and 62. In certain aspects, the disclosure provides a polypeptide comprising or consisting of an amino acid sequence that is at least 98% identical to an amino acid sequence selected from SEQ ID NOs: 25, 27, 29, 31, 33, 35, 37, 39, 41 and 43 or the portion thereof with the leader sequence removed, e.g., a polypeptide comprising or consisting of an amino acid sequence that is at least 98% identical to an amino acid sequence selected from SEQ ID NOs: 53, 54, 55, 56, 57, 58, 59, 60, 61, and 62. In certain aspects, the disclosure provides a polypeptide comprising or consisting of an amino acid sequence that is at least 99% identical to an amino acid sequence selected from SEQ ID NOs: 25, 27, 29, 31, 33, 35, 37, 39, 41 and 43 or the portion thereof with the leader sequence removed, e.g., a polypeptide comprising or consisting of an amino acid sequence that is at least 99% identical to an amino acid sequence selected from SEQ ID NOs: 53, 54, 55, 56, 57, 58, 59, 60, 61, and 62. In certain aspects, the disclosure provides a polypeptide comprising or consisting of an amino acid sequence selected from SEQ ID NOs: 25, 27, 29, 31, 33, 35, 37, 39, 41 and 43 or the portion thereof with the leader sequence removed, e.g., a polypeptide comprising or consisting of an amino acid sequence selected from SEQ ID NOs: 53, 54, 55, 56, 57, 58, 59, 60, 61, and 62.

In certain aspects, the disclosure provides a TβRII polypeptide comprising of an amino acid sequence encoded by a nucleic acid that hybridizes under stringent conditions to a complement of a nucleotide sequence selected from SEQ ID NOs: 26, 28, 30, 32, 34, 36, 38, 40, 42 and 44.

In each of the foregoing, the TβRII polypeptide may be selected that it does not include a full-length TβRII ECD. A TβRII polypeptide may be used as a monomeric protein or in a dimerized form. A TβRII polypeptide may also be fused to a second polypeptide portion to provide improved properties, such as increased half-life or greater ease of production or purification. A fusion may be direct or a linker may be inserted between the TβRII polypeptide and any other portion. A linker may be structured or unstructured and may consist of 1, 2, 3, 4, 5, 10, 15, 20, 30, 50 or more amino acids, optionally relatively free of secondary structure.

In some embodiments, a TβRII polypeptide of the disclosure binds human GDF15 with an equilibrium dissociation constant ($K_D$) less than $1\times10^{-8}$M.

In some embodiments, a TβRII polypeptide of the disclosure has a glycosylation pattern characteristic of expression of the polypeptide in CHO cells.

In some embodiments, the disclosure provides a homodimer comprising two TβRII polypeptides of the disclosure.

In some embodiments, the disclosure provides an isolated polynucleotide comprising a coding sequence for the TβRII polypeptides of the disclosure. In some embodiments, the disclosure provides a recombinant polynucleotide comprising a promoter sequence operably linked to the isolated polynucleotide. In some embodiments, the disclosure provides a cell transformed with an isolated polynucleotide or a recombinant polynucleotide of the disclosure. In some embodiments, the cell is a mammalian cell. In some embodiments, the cell is a CHO cell or a human cell. In some embodiments, the cell is an HEK-293 cell.

In certain aspects, the disclosure provides a pharmaceutical preparation comprising the TβRII polypeptides or homodimers of the disclosure and a pharmaceutically acceptable excipient.

In certain aspects, the disclosure provides a method of modulating the response of a cell to a TGFβ superfamily member, the method comprising exposing the cell to a TβRII polypeptide or homodimer of the disclosure.

In certain aspects, the disclosure provides a method of treating a disease or condition associated with a TGFβ superfamily member in a patient in need thereof, the method comprising administering to the patient an effective amount of the TβRII polypeptides or homodimers of the disclosure. In some embodiments, the TGFβ superfamily member is TGFβ1, TGFβ3 or GDF15.

In some embodiments, the disease or condition is a cancer. In some embodiments, the cancer is selected from stomach cancer, intestinal cancer, skin cancer, breast cancer, melanoma, bone cancer and thyroid cancer.

In some embodiments, the disease or condition is a fibrotic or sclerotic disease or disorder. In some embodiments, the fibrotic or sclerotic disease or disorder is selected from scleroderma, atherosclerosis, liver fibrosis, diffuse systemic sclerosis, glomerulonephritis, neural scarring, dermal scarring, radiation-induced fibrosis, hepatic fibrosis, and myelofibrosis.

In some embodiments, the disease or condition is heart disease.

In some embodiments, the disease or condition is selected from hereditary hemorrhagic telangiectasia (HET), Marfan syndrome, Loeys-Dietz syndrome, familial thoracic aortic aneurysm syndrome, arterial tortuosity syndrome, pre-eclampsia, atherosclerosis, restenosis, and hypertrophic cardiomyopathy/congestive heart failure.

In certain aspects, the disclosure provides an antibody, or antigen binding fragment thereof, that binds to GDF15 and blocks the interaction between GDF15 and TβRII.

In certain aspects, the disclosure provides a GDF15 polypeptide comprising the amino acid sequence of SEQ ID NO: 1 or a fragment thereof that binds TβRII, wherein the GDF15 polypeptide is at least 95%, at least 96%, at least 97%, at least 98%, or at least 99% pure, with respect to protein contaminants.

In certain aspects, the disclosure provides a GDF15 polypeptide comprising the amino acid sequence of SEQ ID NO: 1 or a fragment thereof that binds to a TβRII polypeptide of the disclosure, wherein the GDF15 polypeptide is at least 95%, at least 96%, at least 97%, at least 98%, or at least 99% pure, with respect to protein contaminants.

In some embodiments, the GDF15 polypeptide binds TβRII with an equilibrium dissociation constant ($K_D$) of no greater than $10^{-8}$M. In some embodiments, the GDF15 polypeptide binds to a TβRII polypeptide of the disclosure with an equilibrium dissociation constant ($K_D$) of no greater than $10^{-8}$M.

In some embodiments, the GDF15 polypeptide is produced by expression in CHO cells.

In certain aspects, the disclosure provides a method of concentrating or purifying GDF15, comprising contacting a sample containing GDF15 with a TβRII polypeptide of the disclosure.

BRIEF DESCRIPTION OF THE DRAWINGS

FIG. 1 shows the amino acid sequence of native precursor for human GDF15 (NCBI reference seq: NP_004855.2). Solid underline indicates mature GDF15 (residues 197-308), with N-terminus determined by sequencing. Dotted underline denotes leader (residues 1-29).

FIG. 2 shows a nucleotide sequence encoding native precursor for human GDF15. Solid underline indicates the sequence encoding mature GDF15 (nucleotides 589-924), and dotted underline denotes the sequence encoding the leader (nucleotides 1-87). A silent mutation (G456A) used to disrupt a SfoI site in NM_004864.2 is double underlined.

FIG. 3 shows the amino acid sequence of native precursor for murine GDF15 (NP_035949.2). Solid underline indicates mature GDF15 (residues 192-303), with N-terminus determined by sequencing. Dotted underline denotes leader (residues 1-30).

FIG. 4 shows a nucleotide sequence encoding native precursor for murine GDF15 (derived from NM_011819.2). Solid underline indicates the sequence encoding mature GDF15 (nucleotides 574-909), and dotted underline denotes the sequence encoding the leader (nucleotides 1-90).

FIG. 5 shows the amino acid sequence of native precursor for the B (short) isoform of human TGFβ receptor type II (hTβRII) (NP_003233.4). Solid underline indicates the mature extracellular domain (ECD) (residues 23-159), and double underline indicates valine that is replaced in the A (long) isoform. Dotted underline denotes leader (residues 1-22).

FIG. 6 shows the amino acid sequence of native precursor for the A (long) isoform of human TβRII (NP_001020018.1). Solid underline indicates the mature ECD (residues 23-184), and double underline indicates the splice-generated isoleucine substitution. Dotted underline denotes leader (residues 1-22).

FIG. 7 shows N-terminal alignment of hTβRII$_{short}$ truncations (SEQ ID NOS 64-67, respectively, in order of appearance) and their hTβRII$_{long}$ counterparts (SEQ ID NOS 68-69 and 45-46, respectively, in order of appearance). The 25-amino-acid insertion present in hTβRII$_{long}$ truncations is underlined. Note that the splicing process causes the valine flanking the insertion site in the short isoform to be replaced by an isoleucine in the long isoform. Boxed sequence denotes leader.

DETAILED DESCRIPTION OF THE INVENTION

1. Overview

Proteins described herein are the human forms, unless otherwise specified. NCBI references for the proteins are as follows: human TβRII isoform A (hTβRII$_{long}$), NP_001020018.1; human TβRII isoform B (hTβRII$_{short}$), NP_003233.4; human GDF15, NP_004855.2; murine GDF15, NP_035949.2. Sequences of native TβRII and GDF15 proteins from human and mouse are set forth in FIGS. 1-6.

The TGFβ superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. By manipulating the activity of a member of the TGFβ family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al., Nat Genet. 1997, 17(1):71-4. Similarly, in humans, inactive alleles of GDF8 are associated with increased muscle mass and, reportedly, exceptional strength. Schuelke et al., N Engl J Med 2004, 350: 2682-8.

TGFβ signals are mediated by heteromeric complexes of type I (e.g. TβRI) and type II (e.g. TβRII) serine/threonine kinase receptors, which phosphorylate and activate downstream SMAD proteins upon ligand stimulation (Massague, 2000, Nat. Rev. Mol. Cell Biol. 1:169-178). These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling; and type II receptors are required for binding ligands and for expression of type I receptors. Type I and II receptors form a stable complex after ligand binding, resulting in phosphorylation of type I receptors by type II receptors. TGFβ has three mammalian isoforms, TGFβ1, TGFβ2 and TGFβ3, each with distinct functions in vivo. The binding of TGFβs to TβRII is a crucial step in initiating activation of the TGFβ signaling pathway, leading to phosphorylation of SMAD2, and translocation of the activated SMAD2/SMAD4 complex to the nucleus to modulate gene expression.

Growth differentiation factor 15 (GDF15) is a member of the TGFβ family. Like other ligands in the TGFβ superfamily, which contain a characteristic cysteine knot motif, mature GDF15 is synthesized with a larger prodomain (Harrison et al., Growth Factors 29:174, 2011; Shi et al., Nature 474:343, 2011) that is removed through cleavage by a furin-like protease at the canonical RXXR site to generate mature dimeric GDF15. GDF15 has been described in the literature as macrophage inhibitory cytokine-1 (MIC-1), placental bone morphogenic protein (PLAB), placental transforming growth factor beta (PTGFβ), prostate derived factor (PDF), and non-steroidal anti-inflammatory activated gene-1 (NAG-1) reflecting the different functions that have been implied for this protein. GDF15 has been linked to several physiologic and pathologic conditions. For example, GDF15 is highly expressed in the placenta, and is necessary for the maintenance of pregnancy. GDF15 concentration is also notably increased in the serum of patients with prostate, colorectal, or pancreatic cancer, as well as glioma. GDF15 has not been shown biochemically to bind or interact directly with any receptor. The present disclosure relates in part to the discovery that the TGFβ type II receptor, TβRII, binds to GDF15 with high affinity and is a functional receptor for GDF15. TβRII fusion polypeptides, and other polypeptides containing a ligand-binding portion of TβRII are demonstrated herein to inhibit GDF15-induced gene activation. The potent inhibition of GDF15 signaling provides evidence that TβRII is a functional type II receptor for GDF15, opening a new avenue for therapeutic interventions in this signaling pathway. Therefore, in part, the disclosure identifies a physiological, high-affinity receptor for GDF15 polypeptides.

Surprisingly, soluble TβRII polypeptides are shown herein to have highly specific, high-affinity binding for GDF15. TβRII is the known type II receptor for TGFβ and binds with high affinity to TGFβ1 and TGFβ3. Human TβRII occurs naturally in at least two isoforms—A (long) and B (short)—generated by alternative splicing in the extracellular domain (ECD) (FIGS. 6 and 5 and SEQ ID NOS: 6 and 5). The long isoform has a 25-amino-acid insertion and the splicing process causes the valine flanking the insertion site in the short isoform to be replaced by an isoleucine in the long isoform. Soluble receptor ectodomains can function as scavengers or ligand traps to inhibit ligand-receptor interactions. Ligand traps such as soluble TβRII-Fc fusion proteins incorporating the native TβRII extracellular domain (ectodomain) will function as pan-inhibitors against TβRII ligands, including, TGFβ1, TGFβ3 and based on the findings disclosed herein, GDF15. While in some therapeutic settings this broader spectrum of ligand-binding and signal inhibition may be advantageous, in other settings a more selective molecule may be superior. It is highly desirable for ligand traps such as TβRII ectodomain polypeptides to exhibit selective ligand-binding profiles. The present disclosure relates to the surprising discovery that polypeptides comprising a truncated portion of the extracellular domain of TβRII and/or mutations within the extracellular domain have differential inhibitory effects on cell signaling by GDF15, TGFβ1 or TGFβ3. In part, the disclosure provides ligand traps, generated by a series of mutations and/or truncations in the extracellular domain of TβRII, that exhibit varying ligand-binding profiles distinct from that of the native TβRII extracellular domain. The variant TβRII polypeptides disclosed herein provide advantageous properties relative to the native full-length extracellular domain, and may be used to selectively inhibit pathways mediated by the different TβRII ligands in vivo.

Thus, in certain aspects, the disclosure provides TβRII polypeptides as antagonists of GDF15, TGFβ1 or TGFβ3 for use in treating various GDF15-, TGFβ1- or TGFβ3-associated disorders. While not wishing to be bound to any particular mechanism of action, it is expected that such polypeptides act by binding to GDF15, TGFβ1 or TGFβ3 and inhibiting the ability of these ligands to form ternary signaling complexes.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

2. TβRII Polypeptides

Naturally occurring TβRII proteins are transmembrane proteins, with a portion of the protein positioned outside the cell (the extracellular portion) and a portion of the protein positioned inside the cell (the intracellular portion). Aspects of the present disclosure encompass variant TβRII polypeptides comprising mutations within the extracellular domain and/or truncated portions of the extracellular domain of TβRII. As described above, human TβRII occurs naturally in at least two isoforms—A (long) and B (short)—generated by alternative splicing in the extracellular domain (ECD) (FIGS. 6 and 5 and SEQ ID NOS: 6 and 5). SEQ ID NO: 7, which corresponds to residues 23-159 of SEQ ID NO: 5, depicts the native full-length extracellular domain of the short isoform of TβRII. SEQ ID NO: 13, which corresponds to residues 23-184 of SEQ ID NO: 6, depicts the native full-length extracellular domain of the long isoform of TβRII. Unless noted otherwise, amino acid position numbering with regard to variants based on the TβRII short and long isoforms refers to the corresponding position in the native precursors, SEQ ID NO: 5 and SEQ ID NO:6, respectively.

In certain embodiments, the disclosure provides variant TβRII polypeptides. A TβRII polypeptide of the disclosure may bind to and inhibit the function of a TGFβ superfamily member, such as but not limited to, GDF15, TGFβ1 or TGFβ3. TβRII polypeptides may include a polypeptide consisting of, or comprising, an amino acid sequence at least 80% identical, and optionally at least 85%, 90%, 95%, 96%, 97%, 98%, 99%, or 100% identical to a truncated ECD domain of a naturally occurring TβRII polypeptide, whose C-terminus occurs at any of amino acids 153-159 of SEQ ID NO: 5. TβRII polypeptides may include a polypeptide consisting of, or comprising, an amino acid sequence at least 80% identical, and optionally at least 85%, 90%, 95%, 96%, 97%, 98%, 99%, or 100% identical to a truncated ECD domain of a naturally occurring TβRII polypeptide, whose C-terminus occurs at any of amino acids 178-184 of SEQ ID NO: 6. Optionally, a TβRII polypeptide does not include more than 5 consecutive amino acids, or more than 10, 20, 30, 40, 50, 52, 60, 70, 80, 90, 100, 150 or 200 or more consecutive amino acids from a sequence consisting of amino acids 160-567 of SEQ ID NO: 5 or from a sequence consisting of amino acids 185-592 of SEQ ID NO: 6. The unprocessed TβRII polypeptide may either include or exclude any signal sequence, as well as any sequence N-terminal to the signal sequence. As elaborated herein, the N-terminus of the mature (processed) TβRII polypeptide may occur at any of amino acids 23-35 of SEQ ID NO: 5 or 23-60 of SEQ ID NO: 6. Examples of mature TβRII polypeptides include, but are not limited to, amino acids 23-159 of SEQ ID NO: 5 (set forth in SEQ ID NO: 7), amino acids 29-159 of SEQ ID NO: 5 (set forth in SEQ ID NO: 9), amino acids 35-159 of SEQ ID NO: 5 (set forth in SEQ ID NO: 10), amino acids 23-153 of SEQ ID NO: 5 (set forth in SEQ ID NO: 11), amino acids 29-153 of SEQ ID NO: 5 (set forth in SEQ ID NO: 48), amino acids 35-153 of SEQ ID NO: 5 (set forth in SEQ ID NO: 47), amino acids 23-184 of SEQ ID NO: 6 (set forth in SEQ ID NO: 13), amino acids 29-184 of SEQ ID NO: 6 (set forth in SEQ ID NO: 15), amino acids 60-184 of SEQ ID NO:6 (set forth in SEQ ID NO: 10), amino acids 23-178 of SEQ ID NO: 6 (set forth in SEQ ID NO: 16), amino acids 29-178 of SEQ ID NO: 6 (set forth in SEQ ID NO: 49), and amino acids 60-178 of SEQ ID NO: 6 (set forth in SEQ ID NO: 47). Likewise, a TβRII polypeptide may comprise a polypeptide that is encoded by nucleotides 73-465 of SEQ ID NO: 30, nucleotides 73-447 of SEQ ID NO: 34, nucleotides 73-465 of SEQ ID NO: 38, nucleotides 91-465 of SEQ ID NO: 38, or nucleotides 109-465 of SEQ ID NO: 38, or silent variants thereof or nucleic acids that hybridize to the complement thereof under stringent hybridization conditions (generally, such conditions are known in the art but may, for example, involve hybridization in 50% v/v formamide, 5×SSC, 2% w/v blocking agent, 0.1% N-lauroylsarcosine, and 0.3% SDS at 65° C. overnight and washing in, for example, 5×SSC at about 65° C.). It will be understood by one of skill in the art that corresponding variants based on the long isoform of TβRII will include nucleotide sequences encoding the 25-amino acid insertion along with a conservative Val-Ile substitution at the flanking position C-terminal to the insertion. The TβRII polypeptides accordingly may include isolated extracellular portions of TβRII polypeptides, including both the short and the long isoforms, variants thereof (including variants that comprise, for example, no more than 2, 3, 4, 5, 10, 15, 20, 25, 30, or 35 amino acid substitutions in the sequence corresponding to amino acids 23-159 of SEQ ID NO: 5 or amino acids 23-184 of SEQ ID NO: 6), fragments thereof, and fusion proteins comprising any of the foregoing, but in each case preferably any of the foregoing TβRII polypeptides will retain substantial affinity for at least one of GDF15, TGFβ1 or TGFβ3. Generally, a TβRII polypeptide will be designed to be soluble in aqueous solutions at biologically relevant temperatures, pH levels, and osmolarity.

In some embodiments, the variant TβRII polypeptides of the disclosure comprise one or more mutations in the extracellular domain that confer an altered ligand binding profile. A TβRII polypeptide may include one, two, five or more alterations in the amino acid sequence relative to the corresponding portion of a naturally occurring TβRII polypeptide. In some embodiments, the mutation results in a substitution, insertion, or deletion at the position corresponding to position 70 of SEQ ID NO: 5. In some embodiments, the mutation results in a substitution, insertion, or deletion at the position corresponding to position 110 of SEQ ID NO: 5. Examples include, but are not limited to, an N to D substitution or a D to K substitution in the positions corresponding to positions 70 and 110, respectively, of SEQ ID NO: 5. Examples of such variant TβRII polypeptides include, but are not limited to, the sequences set forth in SEQ ID NO: 8, SEQ ID NO:14, SEQ ID NO: 12 and SEQ ID NO: 17. A TβRII polypeptide may comprise a polypeptide or portion thereof that is encoded by nucleotides 73-483 of SEQ ID NO: 26, nucleotides 73-465 of SEQ ID NO: 42 or silent variants thereof or nucleic acids that hybridize to the complement thereof under stringent hybridization conditions.

In some embodiments, the variant TβRII polypeptides of the disclosure further comprise an insertion of 36 amino acids (SEQ ID NO: 18) between the pair of glutamate residues (positions 151 and 152 of SEQ ID NO: 5, or positions 176 and 177 of SEQ ID NO: 6) located near the C-terminus of the human TβRII ECD, as occurs naturally in the human TβRII isoform C (Konrad et al., BMC Genomics 8:318, 2007).

The disclosure further demonstrates that TβRII polypeptides can be modified to selectively antagonize TβRII ligands. Data presented here show that Fc fusion proteins comprising shorter N-terminally and C-terminally truncated variants of TβRII polypeptides display differential inhibitory effects on cellular signaling mediated by GDF15, TGFβ1 and TGFβ3. Specifically, N-terminally truncated variants beginning at amino acids 29 or 35 of SEQ ID NO: 5 and carrying, respectively, a 6- or 12-amino acid N-terminal truncation of the extracellular domain, were found to inhibit GDF15 most potently, TGFβ3 least potently and TGFβ1 to an intermediate degree, compared to the full length extracellular domain of the short isoform of TβRII. C-terminally truncated variants, ending at amino acid 153 of SEQ ID NO: 5 and carrying a 6-amino acid C-terminal truncation of the extracellular domain had no substantial effect on ligand binding and may therefore be used interchangeably with full length versions. An N to D substitution at the position corresponding to position 70 of SEQ ID NO: 5, was found to inhibit TGFβ3 potently, have intermediate effect on GDF15 and negligible effect on TGFβ1. The N70 residue represents a potential glycosylation site. Further, an Fc fusion protein comprising a D to K substitution at the position corresponding to position 110 of SEQ ID NO: 5, was found to inhibit GDF15 most potently, TGFβ1 least potently and TGFβ3 to an intermediate degree compared to compared to the full length extracellular domain of the short isoform of TβRII. The region around position 110 has not been associated with selectivity for the known TβRII ligands TGFβ1, TGFβ2 and TGFβ3. Thus, unexpectedly, TβRII polypeptides that contain mutations in the ECD, such as but not limited to, N70D and D110K (the numbering of the residues corresponds to that of SEQ ID NO: 5) and/or begin between amino acids 29 and 35 and/or terminate between amino acid 153 and amino acid 159 are all expected to be active and exhibit widely different inhibitory potencies towards the different ligands. Any of these truncated variant forms may be desirable to use, depending on the clinical or experimental setting.

In certain embodiments, a TβRII polypeptide binds to GDF15, and the TβRII polypeptide does not show substantial binding to TGFβ1 or TGFβ3. In certain embodiments, a TβRII polypeptide binds to TGFβ1, and the TβRII polypeptide does not show substantial binding to GDF15 or TGFβ3. In certain embodiments, a TβRII polypeptide binds to TGFβ3, and the TβRII polypeptide does not show substantial binding to GDF15 or TGFβ1. Binding may be assessed using purified proteins in solution or in a surface plasmon resonance system, such as a Biacore™ system.

In certain embodiments, a TβRII polypeptide inhibits GDF15 cellular signaling, and the TβRII polypeptide has an intermediate or limited inhibitory effect on TGFβ1 or TGFβ3. In certain embodiments, a TβRII polypeptide inhibits TGFβ1 cellular signaling, and the TβRII polypeptide has an intermediate or limited inhibitory effect on GDF15 or TGFβ3. In certain embodiments, a TβRII polypeptide inhibits TGFβ3 cellular signaling, and the TβRII polypeptide has an intermediate or limited inhibitory effect on GDF15 or TGFβ1. Inhibitory effect on cell signaling can be assayed by methods known in the art.

Taken together, an active portion of a TβRII polypeptide may comprise amino acid sequences 23-153, 23-154, 23-155, 23-156, 23-157, or 23-158 of SEQ ID NO: 5, as well as variants of these sequences starting at any of amino acids 24-35 of SEQ ID NO: 5. Similarly, an active portion of a TβRII polypeptide may comprise amino acid sequences 23-178, 23-179, 23-180, 23-181, 23-182, or 23-183 of SEQ ID NO: 6, as well as variants of these sequences starting at any of amino acids 24-60 of SEQ ID NO: 6. Exemplary TβRII polypeptides comprise amino acid sequences 29-159, 35-159, 23-153, 29-153 and 35-153 of SEQ ID NO: 5 or amino acid sequences 29-184, 60-184, 23-178, 29-178 and 60-178 of SEQ ID NO: 6. Variants within these ranges are also contemplated, particularly those having at least 80%, 85%, 90%, 95%, or 99% identity to the corresponding portion of SEQ ID NO: 5 or SEQ ID NO: 6. A TβRII polypeptide may be selected that does not include the sequence consisting of amino acids 160-567 of SEQ ID NO:5 or amino acids 185-592 of SEQ ID NO:6.

As described above, the disclosure provides TβRII polypeptides sharing a specified degree of sequence identity or similarity to a naturally occurring TβRII polypeptide. To determine the percent identity of two amino acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The amino acid residues at corresponding amino acid positions are then compared. When a position in the first sequence is occupied by the same amino acid residue as the corresponding position in the second sequence, then the molecules are identical at that position (as used herein amino acid “identity” is equivalent to amino acid “homology”). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

In one embodiment, the percent identity between two amino acid sequences is determined using the Needleman and Wunsch (J Mol. Biol. (48):444-453 (1970)) algorithm which has been incorporated into the GAP program in the GCG software package. In a specific embodiment, the following parameters are used in the GAP program: either a Blosum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (Devereux, J., et al., Nucleic Acids Res. 12(1):387 (1984)). Exemplary parameters include using a NWSgapdna.CMP matrix and a gap weight of 40, 50, 60, 70, or 80 and a length weight of 1, 2, 3, 4, 5, or 6. Unless otherwise specified, percent identity between two amino acid sequences is to be determined using the GAP program using a Blosum 62 matrix, a GAP weight of 10 and a length weight of 3, and if such algorithm cannot compute the desired percent identity, a suitable alternative disclosed herein should be selected.

In another embodiment, the percent identity between two amino acid sequences is determined using the algorithm of E. Myers and W. Miller (CABIOS, 4:11-17 (1989)) which has been incorporated into the ALIGN program (version 2.0), using a PAM120 weight residue table, a gap length penalty of 12 and a gap penalty of 4.

Another embodiment for determining the best overall alignment between two amino acid sequences can be determined using the FASTDB computer program based on the algorithm of Brutlag et al. (*Comp. App. Biosci.*, 6:237-245 (1990)). In a sequence alignment the query and subject sequences are both amino acid sequences. The result of said global sequence alignment is presented in terms of percent identity. In one embodiment, amino acid sequence identity is performed using the FASTDB computer program based on the algorithm of Brutlag et al. (*Comp. App. Biosci.*, 6:237-245 (1990)). In a specific embodiment, parameters employed to calculate percent identity and similarity of an amino acid alignment comprise: Matrix=PAM 150, k-tuple=2, Mismatch Penalty=1, Joining Penalty=20, Randomization Group Length=0, Cutoff Score=1, Gap Penalty=5 and Gap Size Penalty=0.05.

TβRII polypeptides may additionally include any of various leader sequences at the N-terminus. Such a sequence would allow the peptides to be expressed and targeted to the secretion pathway in a eukaryotic system. See, e.g., Ernst et al., U.S. Pat. No. 5,082,783 (1992). Alternatively, a native TβRII signal sequence may be used to effect extrusion from the cell. Possible leader sequences include native leaders, tissue plasminogen activator (TPA) and honeybee mellitin (SEQ ID NOs. 22-24, respectively). Examples of TβRII-Fc fusion proteins incorporating a TPA leader sequence include SEQ ID NOs: 25, 27, 29, 31, 33, 35, 37, 39, 41, and 43. Processing of signal peptides may vary depending on the leader sequence chosen, the cell type used and culture conditions, among other variables, and therefore actual N-terminal start sites for mature TβRII polypeptides may shift by 1, 2, 3, 4 or 5 amino acids in either the N-terminal or C-terminal direction. Examples of TβRII-Fc fusion proteins include SEQ ID NOs: 25, 27, 29, 31, 33, 35, 37, 39, 41, 43, 53, 54, 55, 56, 57, 58, 59, 60, 61, and 62, as shown herein with the TβRII polypeptide portion underlined (see Examples). It will be understood by one of skill in the art that corresponding variants based on the long isoform of TβRII will include the 25-amino acid insertion along with a conservative Val-Ile substitution at the flanking position C-terminal to the insertion.

In certain embodiments, the present disclosure contemplates specific mutations of the TβRII polypeptides so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (or asparagine-X-serine) (where "X" is any amino acid) which is specifically recognized by appropriate cellular glycosylation enzymes. The alteration may also be made by the addition of, or substitution by, one or more serine or threonine residues to the sequence of the wild-type TβRII polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a TβRII polypeptide is by chemical or enzymatic coupling of glycosides to the TβRII polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on a TβRII polypeptide may be accomplished chemically and/or enzymatically. Chemical deglycosylation may involve, for example, exposure of the TβRII polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on TβRII polypeptides can be achieved by the use of a variety of endo- and exo-glycosidases as described by Thotakura et al. (1987) Meth. Enzymol. 138:350. The sequence of a TβRII polypeptide may be adjusted, as appropriate, depending on the type of expression system used, as mammalian, yeast, insect and plant cells may all introduce differing glycosylation patterns that can be affected by the amino acid sequence of the peptide. In general, TβRII polypeptides for use in humans will be expressed in a mammalian cell line that provides proper glycosylation, such as HEK293 or CHO cell lines, although other mammalian expression cell lines, yeast cell lines with engineered glycosylation enzymes, and insect cells are expected to be useful as well.

This disclosure further contemplates a method of generating mutants, particularly sets of combinatorial mutants of a TβRII polypeptide, as well as truncation mutants; pools of combinatorial mutants are especially useful for identifying functional variant sequences. The purpose of screening such combinatorial libraries may be to generate, for example, TβRII polypeptide variants which can act as either agonists or antagonist, or alternatively, which possess novel activities all together. A variety of screening assays are provided below, and such assays may be used to evaluate variants. For example, a TβRII polypeptide variant may be screened for ability to bind to a TβRII ligand, to prevent binding of a TβRII ligand to a TβRII polypeptide or to interfere with signaling caused by a TβRII ligand. The activity of a TβRII polypeptide or its variants may also be tested in a cell-based or in vivo assay, particularly any of the assays disclosed in the Examples.

Combinatorially-derived variants can be generated which have a selective or generally increased potency relative to a TβRII polypeptide comprising an extracellular domain of a naturally occurring TβRII polypeptide. Likewise, mutagenesis can give rise to variants which have serum half-lives dramatically different than the corresponding wild-type TβRII polypeptide. For example, the altered protein can be rendered either more stable or less stable to proteolytic degradation or other processes which result in destruction of, or otherwise elimination or inactivation of, a native TβRII polypeptide. Such variants, and the genes which encode them, can be utilized to alter TβRII polypeptide levels by modulating the half-life of the TβRII polypeptides. For instance, a short half-life can give rise to more transient biological effects and can allow tighter control of recombinant TβRII polypeptide levels within the patient. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential TβRII polypeptide sequences. For instance, a mixture of synthetic oligonucleotides can be enzymatically ligated into gene sequences such that the degenerate set of potential TβRII polypeptide nucleotide sequences are expressible as individual polypeptides, or alternatively, as a set of larger fusion proteins (e.g., for phage display).

There are many ways by which the library of potential TβRII polypeptide variants can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, TβRII polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of TβRII polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of TβRII polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include TβRII ligand binding assays and ligand-mediated cell signaling assays.

In certain embodiments, the TβRII polypeptides of the disclosure may further comprise post-translational modifications in addition to any that are naturally present in the TβRII polypeptides. Such modifications include, but are not limited to, acetylation, carboxylation, glycosylation, phosphorylation, lipidation, pegylation (polyethylene glycol) and acylation. As a result, the modified TβRII polypeptides may contain non-amino acid elements, such as polyethylene glycols, lipids, mono- or poly-saccharides, and phosphates. Effects of such non-amino acid elements on the functionality of a TβRII polypeptide may be tested as described herein for other TβRII polypeptide variants. When a TβRII polypeptide is produced in cells by cleaving a nascent form of the TβRII polypeptide, post-translational processing may also be important for correct folding and/or function of the protein. Different cells (such as CHO, HeLa, MDCK, 293, WI38, NIH-3T3 or HEK-293) have specific cellular machinery and characteristic mechanisms for such post-translational activities and may be chosen to ensure the correct modification and processing of the TβRII polypeptides.

In certain aspects, functional variants or modified forms of the TβRII polypeptides include fusion proteins having at least a portion of the TβRII polypeptides and one or more fusion domains. Well-known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$) (SEQ ID NO: 63) fusion partners. As another example, a fusion domain may be selected so as to facilitate detection of the TβRII polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, a TβRII polypeptide is fused with a domain that stabilizes the TβRII polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains.

As specific examples, the present disclosure provides fusion proteins comprising variants of TβRII polypeptides fused to one of three Fc domain sequences (e.g., SEQ ID NOs: 19, 20, and 21). Optionally, the Fc domain has one or more mutations at residues such as Asp-265, Lys-322, and Asn-434 (numbered in accordance with the corresponding full-length IgG). In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wild-type Fc domain.

It is understood that different elements of the fusion proteins may be arranged in any manner that is consistent with the desired functionality. For example, a TβRII polypeptide may be placed C-terminal to a heterologous domain, or, alternatively, a heterologous domain may be placed C-terminal to a TβRII polypeptide. The TβRII polypeptide domain and the heterologous domain need not be adjacent in a fusion protein, and additional domains or amino acid sequences may be included C- or N-terminal to either domain or between the domains.

As used herein, the term "immunoglobulin Fc domain" or simply "Fc" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain.

In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant region is discussed in detail in U.S. Pat. Nos. 5,541,087 and 5,726,044. The choice of particular immunoglobulin heavy chain constant region sequences and subclasses to achieve a particular result is considered to be within the level of skill in the art. The portion of the DNA construct encoding the immunoglobulin Fc region preferably comprises at least a portion of a hinge domain, and preferably at least a portion of a $CH_3$ domain of Fc gamma or the homologous domains in any of IgA, IgD, IgE, or IgM.

Furthermore, it is contemplated that substitution or deletion of amino acids within the immunoglobulin heavy chain constant regions may be useful in the practice of the methods and compositions disclosed herein. One example would be to introduce amino acid substitutions in the upper CH2 region to create an Fc variant with reduced affinity for Fc receptors (Cole et al. (1997) J. Immunol. 159:3613).

In certain embodiments, the present disclosure makes available isolated and/or purified forms of the TβRII polypeptides, which are isolated from, or otherwise substantially free of (e.g., at least 80%, 90%, 95%, 96%, 97%, 98%, or 99% free of), other proteins and/or other TβRII polypeptide species. TβRII polypeptides will generally be produced by expression from recombinant nucleic acids.

In certain embodiments, the disclosure includes nucleic acids encoding soluble TβRII polypeptides comprising the coding sequence for an extracellular portion of a TβRII protein. In further embodiments, this disclosure also pertains to a host cell comprising such nucleic acids. The host cell may be any prokaryotic or eukaryotic cell. For example, a polypeptide of the present disclosure may be expressed in bacterial cells such as E. coli, insect cells (e.g., using a baculovirus expression system), yeast, or mammalian cells. Other suitable host cells are known to those skilled in the art. Accordingly, some embodiments of the present disclosure further pertain to methods of producing the TβRII polypeptides.

3. Nucleic Acids Encoding TβRII Polypeptides

In certain aspects, the disclosure provides isolated and/or recombinant nucleic acids encoding any of the TβRII polypeptides, including fragments, functional variants and fusion proteins disclosed herein. SEQ ID NO: 26, 28, 30, 32, 34, 36, 38, 40, 42, and 44 encode variants of TβRII extracellular domain fused to an IgG2 Fc or an N-terminally truncated IgG1 Fc domain. The subject nucleic acids may be single-stranded or double stranded. Such nucleic acids may be DNA or RNA molecules. These nucleic acids may be used, for example, in methods for making TβRII polypeptides or as direct therapeutic agents (e.g., in an antisense, RNAi or gene therapy approach).

In certain aspects, the subject nucleic acids encoding TβRII polypeptides are further understood to include nucleic acids that are variants of SEQ ID NOs: 26, 28, 30, 32, 34, 36, 38, 40, 42, and 44. Variant nucleotide sequences include sequences that differ by one or more nucleotide substitutions, additions or deletions, such as allelic variants.

In certain embodiments, the disclosure provides isolated or recombinant nucleic acid sequences that are at least 80%, 85%, 90%, 95%, 96%, 97%, 98%, 99% or 100% identical to SEQ ID NOs: 26, 28, 30, 32, 34, 36, 38, 40, 42, and 44. One of ordinary skill in the art will appreciate that nucleic acid sequences complementary to SEQ ID NOs: 26, 28, 30, 32, 34, 36, 38, 40, 42, and 44, and variants of SEQ ID NOs: 26, 28, 30, 32, 34, 36, 38, 40, 42, and 44 are also within the scope of this disclosure. In further embodiments, the nucleic acid sequences of the disclosure can be isolated, recombinant, and/or fused with a heterologous nucleotide sequence, or in a DNA library.

In other embodiments, nucleic acids of the disclosure also include nucleotide sequences that hybridize under highly stringent conditions to the nucleotide sequences designated in SEQ ID NOs: 26, 28, 30, 32, 34, 36, 38, 40, 42, and 44 complement sequences of SEQ ID NOs: 26, 28, 30, 32, 34, 36, 38, 40, 42, and 44, or fragments thereof. As discussed above, one of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In some embodiments, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 26, 28, 30, 32, 34, 36, 38, 40, 42, and 44 due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

It will be appreciated by one of skill in the art that corresponding variants based on the long isoform of TβRII will include nucleotide sequences encoding the 25-amino acid insertion along with a conservative Val-Ile substitution at the flanking position C-terminal to the insertion. It will also be appreciated that corresponding variants based on either the long (A) or short (B) isoforms of TβRII will include variant nucleotide sequences comprising an insertion of 108 nucleotides, encoding a 36-amino-acid insertion (SEQ ID NO: 18), at the same location described for naturally occurring TβRII isoform C (see Exemplification).

In certain embodiments, the recombinant nucleic acids of the disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects disclosed herein, the subject nucleic acid is provided in an expression vector comprising a nucleotide sequence encoding a TβRII polypeptide and operably linked to at least one regulatory sequence. Regulatory sequences are art-recognized and are selected to direct expression of the TβRII polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a TβRII polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid included in the disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant TβRII polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual,* 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In certain embodiments, a vector will be designed for production of the subject TβRII polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). In a preferred embodiment, a vector will be designed for production of the subject TβRII polypeptides in HEK-293 cells. As will be apparent, the subject gene constructs can be used to cause expression of the subject TβRII polypeptides in cells propagated in culture, e.g., to produce proteins, including fusion proteins or variant proteins, for purification.

This disclosure also pertains to a host cell transfected with a recombinant gene including a coding sequence (e.g., SEQ ID NOs: 26, 28, 30, 32, 34, 36, 38, 40, 42, or 44) for one or more of the subject TβRII polypeptides. The host cell may be any prokaryotic or eukaryotic cell. For example, a TβRII polypeptide disclosed herein may be expressed in bacterial cells such as *E. coli,* insect cells (e.g., using a baculovirus expression system), yeast, or mammalian cells. Other suitable host cells are known to those skilled in the art.

Accordingly, the present disclosure further pertains to methods of producing the subject TβRII polypeptides. For example, a host cell transfected with an expression vector encoding a TβRII polypeptide can be cultured under appropriate conditions to allow expression of the TβRII polypeptide to occur. The TβRII polypeptide may be secreted and isolated from a mixture of cells and medium containing the TβRII polypeptide. Alternatively, the TβRII polypeptide may be retained cytoplasmically or in a membrane fraction and the cells harvested, lysed and the protein isolated. A cell culture includes host cells, and media. Suitable media for cell culture are well known in the art. The subject TβRII polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the TβRII polypeptides and affinity purification with an agent that binds to a domain fused to the TβRII polypeptide (e.g., a protein A column may be used to purify an TβRII-Fc fusion). In a preferred embodiment, the TβRII polypeptide is a fusion protein containing a domain which facilitates its purification. As an example, purification may be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

In another embodiment, a fusion gene coding for a purification leader sequence, such as a poly-(His)/enterokinase cleavage site sequence at the N-terminus of the desired portion of the recombinant TβRII polypeptide, can allow purification of the expressed fusion protein by affinity chromatography using a $Ni^{2+}$ metal resin. The purification leader sequence can then be subsequently removed by treatment with enterokinase to provide the purified TβRII polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology,* eds. Ausubel et al., John Wiley & Sons: 1992).

Examples of categories of nucleic acid compounds that are antagonists of TβRII, TGFβ1, TGFβ3 and GDF15 include antisense nucleic acids, RNAi constructs and catalytic nucleic acid constructs. A nucleic acid compound may be single or double stranded. A double stranded compound may also include regions of overhang or non-complementarity, where one or the other of the strands is single-stranded. A single-stranded compound may include regions of self-complementarity, meaning that the compound forms a so-called "hairpin" or "stem-loop" structure, with a region of double helical structure. A nucleic acid compound may comprise a nucleotide sequence that is complementary to a region consisting of no more than 1000, no more than 500, no more than 250, no more than 100 or no more than 50, 35, 30, 25, 22, 20 or 18 nucleotides of the full-length TβRII nucleic acid sequence or ligand nucleic acid sequence. The region of complementarity will preferably be at least 8 nucleotides, and optionally at least 10 or at least 15 nucleotides, such as between 15 and 25 nucleotides. A region of complementarity may fall within an intron, a coding sequence, or a noncoding sequence of the target transcript, such as the coding sequence portion. Generally, a nucleic acid compound will have a length of about 8 to about 500 nucleotides or base pairs in length, such as about 14 to about 50 nucleotides. A nucleic acid may be a DNA (particularly for use as an antisense), RNA, or RNA:DNA hybrid. Any one strand may include a mixture of DNA and RNA, as well as modified forms that cannot readily be classified as either DNA or RNA. Likewise, a double-stranded compound may be DNA:DNA, DNA:RNA or RNA:RNA, and any one strand may also include a mixture of DNA and RNA, as well as modified forms that cannot readily be classified as either DNA or RNA. A nucleic acid compound may include any of a variety of modifications, including one or modifications to the backbone (the sugar-phosphate portion in a natural nucleic acid, including internucleotide linkages) or the base portion (the purine or pyrimidine portion of a natural nucleic acid). An antisense nucleic acid compound will preferably have a length of about 15 to about 30 nucleotides and will often contain one or more modifications to improve characteristics such as stability in the serum, in a cell or in a place where the compound is likely to be delivered, such as the stomach in the case of orally delivered compounds and the lung for inhaled compounds. In the case of an RNAi construct, the strand complementary to the target transcript will generally be RNA or modifications thereof. The other strand may be RNA, DNA, or any other variation. The duplex portion of double-stranded or single-stranded "hairpin" RNAi construct will preferably have a length of 18 to 40 nucleotides in length and optionally about 21 to 23 nucleotides in length, so long as it serves as a Dicer substrate. Catalytic or enzymatic nucleic acids may be ribozymes or DNA enzymes and may also contain modified forms. Nucleic acid compounds may inhibit expression of the target by about 50%, 75%, 90%, or more when contacted with cells under physiological conditions and at a concentration where a nonsense or sense control has little or no effect. Preferred concentrations for testing the effect of nucleic acid compounds are 1, 5 and 10 micromolar. Nucleic acid compounds may also be tested for effects on, for example, angiogenesis.

4. Alterations in Fc-fusion Proteins

The application further provides TβRII-Fc fusion proteins with engineered or variant Fc regions. Such antibodies and Fc fusion proteins may be useful, for example, in modulating effector functions, such as, antigen-dependent cytotoxicity (ADCC) and complement-dependent cytotoxicity (CDC). Additionally, the modifications may improve the stability of the antibodies and Fc fusion proteins. Amino acid sequence variants of the antibodies and Fc fusion proteins are prepared by introducing appropriate nucleotide changes into the DNA, or by peptide synthesis. Such variants include, for example, deletions from, and/or insertions into and/or substitutions of, residues within the amino acid sequences of the antibodies and Fc fusion proteins disclosed herein. Any combination of deletion, insertion, and substitution is made to arrive at the final construct, provided that the final construct possesses the desired characteristics. The amino acid changes also may alter post-translational processes of the antibodies and Fc fusion proteins, such as changing the number or position of glycosylation sites.

Antibodies and Fc fusion proteins with reduced effector function may be produced by introducing changes in the amino acid sequence, including, but are not limited to, the Ala-Ala mutation described by Bluestone et al. (see WO 94/28027 and WO 98/47531; also see Xu et al. 2000 Cell Immunol 200; 16-26). Thus, in certain embodiments, antibodies and Fc fusion proteins of the disclosure with mutations within the constant region including the Ala-Ala mutation may be used to reduce or abolish effector function. According to these embodiments, antibodies and Fc fusion proteins may comprise a mutation to an alanine at position 234 or a mutation to an alanine at position 235, or a combination thereof. In one embodiment, the antibody or Fc fusion protein comprises an IgG4 framework, wherein the Ala-Ala mutation would describe a mutation(s) from phenylalanine to alanine at position 234 and/or a mutation from leucine to alanine at position 235. In another embodiment, the antibody or Fc fusion protein comprises an IgG1 framework, wherein the Ala-Ala mutation would describe a mutation(s) from leucine to alanine at position 234 and/or a mutation from leucine to alanine at position 235. The antibody or Fc fusion protein may alternatively or additionally carry other mutations, including the point mutation K322A in the CH2 domain (Hezareh et al. 2001 J Virol. 75: 12161-8).

In particular embodiments, the antibody or Fc fusion protein may be modified to either enhance or inhibit complement dependent cytotoxicity (CDC). Modulated CDC activity may be achieved by introducing one or more amino acid substitutions, insertions, or deletions in an Fc region (see, e.g., U.S. Pat. No. 6,194,551). Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See Caron et al., J. Exp Med. 176:1191-1195 (1992) and Shopes, B. J. Immunol. 148:2918-2922 (1992), WO99/51642, Duncan & Winter Nature 322: 738-40 (1988); U.S. Pat. Nos. 5,648,260; 5,624,821; and WO94/29351.

5. GDF15-TβRII Signaling

The present disclosure relates in part to the discovery that the TGFβ type II receptor (TβRII) binds to GDF15 with high affinity. Heretofore, GDF15 has not been shown biochemically to bind or interact directly with a receptor. Inadequate or inappropriate ligand purification could be a potential reason for the inactivity of commercially available GDF15. Exemplary GDF15 polypeptides demonstrating a TβRII binding activity and methods of making and purifying such polypeptides are disclosed herein. Sequences of native precursor GDF15 proteins and nucleotides from human and mouse are set forth in FIGS. 1-4. Mature human GDF15 extends from residues 197 to 308 of SEQ ID NO: 1. Similarly, mature mouse GDF15 extends from residues 192 to 303 of SEQ ID NO: 3. In certain embodiments, the present disclosure makes available isolated and/or purified forms of the GDF15 polypeptides or fragments thereof, which are isolated from, or otherwise substantially free of (e.g., at least 80%, 90%, 95%, 96%, 97%, 98%, or 99% free of), other proteins and/or other GDF15 polypeptide species. The GDF15 polypeptides of the disclosure bind to TβRII with high affinity. Binding may be assessed using purified proteins in solution or in a surface plasmon resonance system, such as a Biacore™ system. The GDF15 polypeptides will have an affinity (a dissociation constant) of about $10^{-6}$, $10^{-7}$, $10^{-8}$, $10^{-9}$M or less for TβRII polypeptides. Preferably, the GDF15 polypeptides of the disclosure are isolated and purified according to methods described herein. GDF15 polypeptides will generally be produced by expression from recombinant nucleic acids.

GDF15 polypeptides may include a polypeptide consisting of, or comprising, an amino acid sequence at least 80% identical, and optionally at least 85%, 90%, 95%, 96%, 97%, 98%, 99%, or 100% identical to the GDF15 polypeptide of SEQ ID NO: 1 or SEQ ID NO: 3, or a functional fragment thereof. GDF15 polypeptides may include a polypeptide consisting of, or comprising, an amino acid sequence at least 80% identical, and optionally at least 85%, 90%, 95%, 96%, 97%, 98%, 99%, or 100% identical to the GDF15 polypeptide comprising residues 197 to 308 of SEQ ID NO: 1 or residues 192 to 303 of SEQ ID NO: 3, or a functional fragment thereof. The unprocessed GDF15 polypeptide may either include or exclude any signal sequence, as well as any sequence N-terminal to the signal sequence. A GDF15 polypeptide may include variants of SEQ ID NO: 1 or SEQ ID NO: 3, or portions thereof, corresponding to 197 to 308 of SEQ ID NO: 1 or residues 192 to 303 of SEQ ID NO: 3, respectively (including variants that comprise, for example, no more than 2, 3, 4, 5, 10, 15, 20, 25, 30, or 35 amino acid substitutions in the sequence of SEQ ID NO: 1 or SEQ ID NO: 3), fragments thereof, and fusion proteins comprising any of the foregoing, but in each case preferably any of the foregoing GDF15 polypeptides will possess substantial affinity for a TβRII polypeptide.

In certain embodiments, the GDF15 polypeptides of the disclosure may further comprise post-translational modifications in addition to any that are naturally present in the GDF15 polypeptides. Such modifications include, but are not limited to, acetylation, carboxylation, glycosylation, phosphorylation, lipidation, pegylation (polyethylene glycol) and acylation. As a result, the modified GDF15 polypeptides may contain non-amino acid elements, such as polyethylene glycols, lipids, mono- or poly-saccharides, and phosphates. Effects of such non-amino acid elements on the functionality of a GDF15 polypeptide may be tested as described herein for other GDF15 polypeptides. When a GDF15 polypeptide is produced in cells by cleaving a nascent form of the GDF15 polypeptide, post-translational processing may also be important for correct folding and/or function of the protein. Different cells (such as CHO, HeLa, MDCK, 293, WI38, NIH-3T3 or HEK-293) have specific cellular machinery and characteristic mechanisms for such post-translational activities and may be chosen to ensure the correct modification and processing of the GDF15 polypeptides.

In certain embodiments, the disclosure includes nucleic acids encoding precursor and mature GDF15 polypeptides. In further embodiments, this disclosure also pertains to a host cell comprising such nucleic acids. The host cell may be any prokaryotic or eukaryotic cell. For example, a polypeptide of the present disclosure may be expressed in bacterial cells such as E. coli, insect cells (e.g., using a baculovirus expression system), yeast, or mammalian cells. Other suitable host cells are known to those skilled in the art. Accordingly, some embodiments of the present disclosure further pertain to methods of producing the GDF15 polypeptides.

In certain aspects, the disclosure provides isolated and/or recombinant nucleic acids encoding any of the GDF15 polypeptides, including fragments, functional variants and fusion proteins disclosed herein. The subject nucleic acids may be single-stranded or double-stranded. Such nucleic acids may be DNA or RNA molecules. These nucleic acids may be used, for example, in methods for making GDF15 polypeptides or as direct therapeutic agents (e.g., in an antisense, RNAi or gene therapy approach).

In certain aspects, the subject nucleic acids encoding GDF15 polypeptides are further understood to include nucleic acids that are variants of SEQ ID NO: 1 or SEQ ID NO: 3. Variant nucleotide sequences include sequences that differ by one or more nucleotide substitutions, additions or deletions, such as allelic variants.

In certain embodiments, the disclosure provides isolated or recombinant nucleic acid sequences that are at least 80%, 85%, 90%, 95%, 96%, 97%, 98%, 99% or 100% identical to SEQ ID NO: 1 or SEQ ID NO: 3. One of ordinary skill in the art will appreciate that nucleic acid sequences complementary to SEQ ID NO: 1 or SEQ ID NO: 3 and variants of SEQ ID NO: 1 or SEQ ID NO: 3 are also within the scope of this disclosure. In further embodiments, the nucleic acid sequences of the disclosure can be isolated, recombinant, and/or fused with a heterologous nucleotide sequence, or in a DNA library.

In other embodiments, nucleic acids of the disclosure also include nucleotide sequences that hybridize under highly stringent conditions to the nucleotide sequences designated in SEQ ID NO: 1 or SEQ ID NO: 3, complement sequences of SEQ ID NO: 1 or SEQ ID NO: 3, or fragments thereof. As discussed above, one of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In some embodiments, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NO: 1 or SEQ ID NO: 3 due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant nucleic acids of the disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects disclosed herein, the subject nucleic acid is provided in an expression vector comprising a nucleotide sequence encoding a GDF15 polypeptide and operably linked to at least one regulatory sequence. Regulatory sequences are art-recognized and are selected to direct expression of the GDF15 polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a GDF15 polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid included in the disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant GDF15 polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual,* 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject TβRII polypeptides in CHO cells, such as a Pcmv-Script vector (Stratagene, La Jolla, Calif.), pcDNA4 vectors (Invitrogen, Carlsbad, Calif.), pCI-neo vectors (Promega, Madison, Wis.) and UCOE™-derived vectors (Millipore). As will be apparent, the subject gene constructs can be used to cause expression of the subject GDF15 polypeptides in cells propagated in culture, e.g., to produce proteins, including fusion proteins or variant proteins, for purification.

This disclosure also pertains to a host cell transfected with a recombinant gene including a coding sequence (e.g., SEQ ID NO: 1 or SEQ ID NO:3) for one or more of the subject GDF15 polypeptides. The host cell may be any prokaryotic or eukaryotic cell. For example, a GDF15 polypeptide disclosed herein may be expressed in bacterial cells such as *E. coli,* insect cells (e.g., using a baculovirus expression system), yeast, or mammalian cells. Other suitable host cells are known to those skilled in the art. In a preferred embodiment, a GDF15 polypeptide disclosed herein is expressed in CHO cells.

Accordingly, the present disclosure further pertains to methods of producing the subject GDF15 polypeptides. For example, a host cell transfected with an expression vector encoding a GDF15 polypeptide can be cultured under appropriate conditions to allow expression of the GDF15 polypeptide to occur. The GDF15 polypeptide may be secreted and isolated from a mixture of cells and medium containing the GDF15 polypeptide. Alternatively, the TβRII polypeptide may be retained cytoplasmically or in a membrane fraction and the cells harvested, lysed and the protein isolated. A cell culture includes host cells and media. Suitable media for cell culture are well known in the art. The subject GDF15 polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the GDF15 polypeptides and affinity purification with an agent that binds to a domain fused to the GDF15 polypeptide (e.g., a protein A column may be used to purify an GDF15-Fc fusion). In a preferred embodiment, the GDF15 polypeptide is a fusion protein containing a domain which facilitates its purification. As an example, purification may be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

In a preferred embodiment, the subject GDF15 polypeptides are purified from culture media using a series of cation-exchange column chromatography steps. Examples of the material used for the cation exchange column can be resins having substituents such as carboxymethyl (CM), sulfoethyl (SE), sulfopropyl (SP), phosphate (P) and sulfonate (S). Examples of the material used for the cation exchange column chromatography include SP Sepharose™ Fast Flow, Q Sepharose™ Fast Flow, DEAE Sepharose™ Fast Flow, Capto™ S, Capto™ DEAE (GE Healthcare), S HyperCel™ (Pall), TOYOPEARL GigaCap S-650 (TOSOH) or weak cation exchangers such as carboxymethyl. SP Sepharose™ Fast Flow and Q Sepharose™ Fast Flow are preferred.

To begin purification, parameters of the conditioned media from host cells stably expressing a GDF15 polypeptide, such as pH, ionic strength, and temperature may be adjusted if necessary. In some embodiments, a chromatography column is flushed and equilibrated with one or more solutions prior to contact with a polypeptide containing supernatant. Such solutions can include, for example, a buffer (e.g., Tris, MES, HEPES, histidine, phosphate or sodium acetate, e.g., between 1-500 mM, 25-100 mM, 15-30 mM or 20 mM), and/or salt (e.g., NaCl, NaPO$_4$ sodium acetate, or CaCl$_2$, e.g., between 0-2 M, 1-2 M or 500 mM-1M). The pH of an equilibration solution generally ranges from 3.5-10 (e.g., between pH 3.5-6, 4.0-5.5, 4.5-4.8 or 4.7). After contacting a column with a polypeptide containing fluid, the bound column can be washed. Wash solutions can include a buffer (e.g., Tris, MES, HEPES, histidine, phosphate, or sodium acetate, e.g., between 1-500 mM, 25-100 mM, 15-30 mM or 20 mM), and/or salt (e.g., NaCl, NaPO$_4$, sodium acetate, or CaCl$_2$, e.g., between 0-2 M, 1-2 M, 100 mM-1M or 100 mM-500 mM), and/or an additive (e.g. guanidine, urea, sucrose, arginine, or an arginine derivative), and/or a solvent (e.g., ethanol, acetonitrile, or polyethylene glycol). Wash solutions generally have a pH between 3.5 and 10 (e.g., a pH between 4.5-8.0). Polypeptides can be eluted from a column using a step or gradient change in pH, salt type, salt concentration, solvent type, solvent concentration, displacer type, displacer concentration, or a combination thereof. In general, to elute a polypeptide from a column, the medium is contacted with an elution buffer. In some embodiments, an elution buffer elution buffer contains a buffer (e.g., HEPES or Tris, e.g., 10-100 mM, 25-75 mM or 50 mM) and/or contains a salt (e.g., NaCl or CaCl$_2$, e.g., 0-2 M, e.g., 10-100 mM). In some embodiments, an elution buffer may contain glycine, acetic acid, or citric acid (e.g., 20-250 mM, or 150 mM). An elution buffer may also contain acetic acid (e.g., 20 mM to about 50 mM), an additive (e.g. guanidine, urea, or sucrose, e.g., 1-10 M, 2-8 M or 6 M), and/or a solvent (e.g., ethanol, acetonitrile, polyethylene glycol, e.g., 1-10% solvent, e.g., 5% solvent). The pH of the elution buffer may range from about 5.0 to about 10.0. In some embodiments, pH can be changed (e.g., gradually) to produce a gradient elution. In some embodiments, the pH of the elution buffer is about 8.0. In some embodiments, a series of column chromatography steps are performed.

The data presented herein demonstrates that TβRII polypeptides act as antagonists of GDF15 signaling. Although soluble TβRII polypeptides, and particularly TβRII-Fc, are preferred antagonists, other types of GDF15 antagonists are expected to be useful, including anti-GDF15 antibodies, anti-TβRII antibodies, antisense, RNAi or ribozyme nucleic acids that inhibit the production of GDF15 or TβRII and other inhibitors of GDF15 or TβRII, particularly those that disrupt GDF15-TβRII binding.

An antibody that is specifically reactive with a GDF15 polypeptide and which either binds to GDF15 polypeptide so as to compete with its binding to TβRII polypeptide (binding competitively) or otherwise inhibits GDF15-mediated signaling may be used as an antagonist of GDF15 polypeptide activities. Likewise, an antibody that is specifically reactive with a TβRII polypeptide and which disrupts GDF15 binding may be used as an antagonist.

By using immunogens derived from a GDF15 polypeptide or a TβRII polypeptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the GDF15 polypeptide, an antigenic fragment which is capable of eliciting an antibody response, or a fusion protein. Techniques for conferring immunogenicity on a protein or peptide include conjugation to carriers or other techniques well known in the art. An immunogenic portion of a GDF15 or TβRII polypeptide can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation of a GDF15 polypeptide, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with a GDF15 polypeptide and monoclonal antibodies isolated from a culture comprising such hybridoma cells.

The term "antibody" as used herein is intended to include fragments thereof which are also specifically reactive with a subject polypeptide. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific, single-chain, chimeric, humanized and fully human molecules having affinity for an TβRII or GDF15 polypeptide conferred by at least one CDR region of the antibody. An antibody may further comprise a label attached thereto and able to be detected (e.g., the label can be a radioisotope, fluorescent compound, enzyme or enzyme co-factor).

In certain embodiments, the antibody is a recombinant antibody, which term encompasses any antibody generated in part by techniques of molecular biology, including CDR-grafted or chimeric antibodies, human or other antibodies assembled from library-selected antibody domains, single chain antibodies and single domain antibodies (e.g., human $V_H$ proteins or camelid $V_{HH}$ proteins). In certain embodiments, an antibody of the invention is a monoclonal antibody, and in certain embodiments, the invention makes available methods for generating novel antibodies. For example, a method for generating a monoclonal antibody that binds specifically to a GDF15 polypeptide or TβRII polypeptide may comprise administering to a mouse an amount of an immunogenic composition comprising the antigen polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the antigen. Once obtained, a hybridoma can be propagated in a cell culture, optionally in culture conditions where the hybridoma-derived cells produce the monoclonal antibody that binds specifically to the antigen. The monoclonal antibody may be purified from the cell culture.

The adjective "specifically reactive with" as used in reference to an antibody is intended to mean, as is generally understood in the art, that the antibody is sufficiently selective between the antigen of interest (e.g., a GDF15 polypeptide) and other antigens that are not of interest that the antibody is useful for, at minimum, detecting the presence of the antigen of interest in a particular type of biological sample. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less. Given the high affinity between GDF15 and TβRII, it is expected that a neutralizing anti-GDF15 or anti-TβRII antibody would generally have a dissociation constant of $10^{-9}$ or less.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore™ binding assay, Biacore AB, Uppsala, Sweden), sandwich assays (e.g., the paramagnetic bead system of IGEN International, Inc., Gaithersburg, Md.), western blots, immunoprecipitation assays, and immunohistochemistry.

Examples of categories of nucleic acid compounds that are GDF15 or TβRII antagonists include antisense nucleic acids, RNAi constructs and catalytic nucleic acid constructs. A nucleic acid compound may be single- or double-stranded. A double-stranded compound may also include regions of overhang or non-complementarity, where one or the other of the strands is single-stranded. A single-stranded compound may include regions of self-complementarity, meaning that the compound forms a so-called "hairpin" or "stem-loop" structure, with a region of double helical structure. A nucleic acid compound may comprise a nucleotide sequence that is complementary to a region consisting of no more than 1000, no more than 500, no more than 250, no more than 100 or no more than 50, 35, 30, 25, 22, 20 or 18 nucleotides of the full-length GDF15 nucleic acid sequence or TβRII nucleic acid sequence. The region of complementarity will preferably be at least 8 nucleotides, and optionally at least 10 or at least 15 nucleotides, such as between 15 and 25 nucleotides. A region of complementarity may fall within an intron, a coding sequence or a noncoding sequence of the target transcript, such as the coding sequence portion. Generally, a nucleic acid compound will have a length of about 8 to about 500 nucleotides or base pairs in length, such as about 14 to about 50 nucleotides. A nucleic acid may be a DNA (particularly for use as an antisense), RNA or RNA:DNA hybrid. Any one strand may include a mixture of DNA and RNA, as well as modified forms that cannot readily be classified as either DNA or RNA. Likewise, a double-stranded compound may be DNA:DNA, DNA:RNA or RNA:RNA, and any one strand may also include a mixture of DNA and RNA, as well as modified forms that cannot readily be classified as either DNA or RNA. A nucleic acid compound may include any of a variety of modifications, including one or modifications to the backbone (the sugar-phosphate portion in a natural nucleic acid, including internucleotide linkages) or the base portion (the purine or pyrimidine portion of a natural nucleic acid). An antisense nucleic acid compound will preferably have a length of about 15 to about 30 nucleotides and will often contain one or more modifications to improve characteristics such as stability in the serum, in a cell or in a place where the compound is likely to be delivered, such as the stomach in the case of orally delivered compounds and the lung for inhaled compounds. In the case of an RNAi construct, the strand complementary to the target transcript will generally be RNA or modifications thereof. The other strand may be RNA, DNA or any other variation. The duplex portion of double-stranded or single-stranded "hairpin" RNAi construct will preferably have a length of 18 to 40 nucleotides in length and optionally about 21 to 23 nucleotides in length, so long as it serves as a Dicer substrate. Catalytic or enzymatic nucleic acids may be ribozymes or DNA enzymes and may also contain modified forms. Nucleic acid compounds may inhibit expression of the target by about 50%, 75%, 90% or more when contacted with cells under physiological conditions and at a concentration where a nonsense or sense control has little or no effect. Preferred concentrations for testing the effect of nucleic acid compounds are 1, 5 and 10 micromolar.

6. Screening Assays

In certain aspects, the present invention relates to the use of TβRII polypeptides (e.g., soluble TβRII polypeptides) and GDF15 polypeptides to identify compounds (agents) which are agonist or antagonists of the GDF15-TβRII signaling pathway. Compounds identified through this screening can be tested to assess their ability to modulate GDF15 signaling activity in vitro. Optionally, these compounds can further be tested in animal models to assess their ability to modulate tissue growth in vivo.

There are numerous approaches to screening for therapeutic agents for modulating tissue growth by targeting GDF15 and TβRII polypeptides. In certain embodiments, high-throughput screening of compounds can be carried out to identify agents that perturb GDF15 or TβRII-mediated cell signaling. In certain embodiments, the assay is carried out to screen and identify compounds that specifically inhibit or reduce binding of a TβRII polypeptide to GDF15. Alternatively, the assay can be used to identify compounds that enhance binding of a TβRII polypeptide to GDF15. In a further embodiment, the compounds can be identified by their ability to interact with a GDF15 or TβRII polypeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatable crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between a TβRII polypeptide and GDF15.

Merely to illustrate, in an exemplary screening assay of the present invention, the compound of interest is contacted with an isolated and purified TβRII polypeptide which is ordinarily capable of binding to GDF15. To the mixture of the compound and TβRII polypeptide is then added a composition containing a TβRII ligand. Detection and quantification of TβRII/GDF15 complexes provides a means for determining the compound's efficacy at inhibiting (or potentiating) complex formation between the TβRII polypeptide and GDF15. The efficacy of the compound can be assessed by generating dose response curves from data obtained using various concentrations of the test compound. Moreover, a control assay can also be performed to provide a baseline for comparison. For example, in a control assay, isolated and a purified GDF15 is added to a composition containing the TβRII polypeptide, and the formation of TβRII/GDF15 complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the TβRII polypeptide and GDF15 may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled TβRII polypeptide or GDF15, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between a TβRII polypeptide and its binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments of the invention.

Moreover, the present invention contemplates the use of an interaction trap assay, also known as the "two hybrid assay," for identifying agents that disrupt or potentiate interaction between a TβRII polypeptide and its binding protein. See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present invention contemplates the use of reverse two hybrid systems to identify compounds (e.g., small molecules or peptides) that dissociate interactions between a TβRII polypeptide and its binding protein. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, the subject compounds are identified by their ability to interact with a TβRII or GDF15 polypeptide of the invention. The interaction between the compound and the TβRII or GDF15 polypeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to a GDF15 or TβRII polypeptide. This may include a solid-phase or fluid-phase binding event. Alternatively, the gene encoding a GDF15 or TβRII polypeptide can be transfected with a reporter system (e.g., β-galactosidase, luciferase, or green fluorescent protein) into a cell and screened against the library preferably by a high-throughput screening or with individual members of the library. Other mechanism-based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

In certain aspects, the present invention provides methods and agents for modulating (stimulating or inhibiting) GDF15-mediated cell signaling. Therefore, any compound identified can be tested in whole cells or tissues, in vitro or in vivo, to confirm their ability to modulate GDF15 signaling. Various methods known in the art can be utilized for this purpose.

7. Exemplary Therapeutic Uses

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes amelioration or elimination of the condition once it has been established. In either case, prevention or treatment may be discerned in the diagnosis provided by a physician and the intended result of administration of the therapeutic agent.

The disclosure provides methods of treating or preventing a disease or condition associated with a TGFβ superfamily member by administering to a subject an effective amount of a TβRII polypeptide, including a TβRII-Fc fusion protein or nucleic acid antagonists (e.g., antisense or siRNA) of the foregoing, hereafter collectively referred to as "therapeutic agents". In some embodiments the disease or condition is associated with dysregulated GDF15, TGFβ1 or TGFβ3 signaling. Also provided are methods and compositions for treating certain cardiovascular or vascular disorders. In addition, the disclosure provides methods and compositions for treating or preventing cancer. In addition, the disclosure provides methods and compositions for treating or preventing fibrotic disorders and conditions.

In particular, polypeptide therapeutic agents of the present disclosure are useful for treating or preventing chronic vascular or cardiovascular diseases. Exemplary disorders of this kind include, but are not limited to, heart disease (including myocardial disease, myocardial infarct, angina pectoris, and heart valve disease); renal disease (including chronic glomerular inflammation, diabetic renal failure, and lupus-related renal inflammation); disorders associated with atherosclerosis or other types of arteriosclerosis (including stroke, cerebral hemorrhage, subarachnoid hemorrhage, angina pectoris, and renal arteriosclerosis); thrombotic disorders (including cerebral thrombosis, thrombotic intestinal necrosis); complications of diabetes (including diabetes-related retinal disease, cataracts, diabetes-related renal disease, diabetes-related neuropathology, diabetes-related gangrene, and diabetes-related chronic infection); vascular inflammatory disorders (systemic lupus erythematosus, joint rheumatism, joint arterial inflammation, large-cell arterial inflammation, Kawasaki disease, Takayasu arteritis, Churg-Strauss syndrome, and Henoch-Schoenlein purpura); diabetic vasculopathies; and cardiac disorders such as congenital heart disease, cardiomyopathy (e.g., dilated, hypertrophic, restrictive cardiomyopathy), and congestive heart failure. Exemplary disorders further include, but are not limited to, hereditary hemorrhagic telangiectasia (HHT), Marfan syndrome, Loeys-Dietz syndrome, familial thoracic aortic aneurysm syndrome, arterial tortuosity syndrome, pre-eclampsia, and restenosis.

The TβRII polypeptide can be administered to the subject alone, or in combination with one or more agents or therapeutic modalities, e.g., therapeutic agents, which are useful for treating TGFβ associated cardiovascular disorders and/or conditions. In certain embodiments, the second agent or therapeutic modality is chosen from one or more of: angioplasty, beta blockers, anti-hypertensives, cardiotonics, anti-thrombotics, vasodilators, hormone antagonists, endothelin antagonists, calcium channel blockers, phosphodiesterase inhibitors, angiotensin type 2 antagonists and/or cytokine blockers/inhibitors In particular, polypeptide therapeutic agents of the present disclosure are useful for treating or preventing a cancer (tumor). The terms "cancer" and "cancerous" refer to or describe, the physiological condition in mammals that is typically characterized by unregulated cell growth/proliferation. Examples of cancer, or neoplastic disorders, include but are not limited to, carcinoma, lymphoma, blastoma, sarcoma, and leukemia. More particular examples of such cancers include squamous cell cancer, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, prostate cancer, vulval cancer, thyroid cancer, hepatic carcinoma, stomach cancer, intestinal cancer, skin cancer, bone cancer, gastric cancer, melanoma, and various types of head and neck cancer, including squamous cell head and neck cancer. Other examples of neoplastic disorders and related conditions include esophageal carcinomas, thecomas, arrhenoblastomas, endometrial hyperplasia, endometriosis, fibrosarcomas, choriocarcinoma, nasopharyngeal carcinoma, laryngeal carcinomas, hepatoblastoma, Kaposi's sarcoma, skin carcinomas, hemangioma, cavernous hemangioma, hemangioblastoma, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, Wilm's tumor, renal cell carcinoma, prostate carcinoma, abnormal vascular proliferation associated with phakomatoses, and Meigs' syndrome. A cancer that is particularly amenable to treatment with the therapeutic agents described herein may be characterized by one or more of the following: the cancer has elevated TβRII levels detectable in the tumor or the serum, increased GDF15, TGFβ1 or TGFβ3 expression levels or biological activity, is metastatic or at risk of becoming metastatic, or any combination thereof.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject methods of the disclosure can be used alone. Alternatively, the subject methods may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present disclosure recognizes that the effectiveness of conventional cancer therapies (e.g., chemotherapy, radiation therapy, phototherapy, immunotherapy, and surgery) can be enhanced through the use of a subject polypeptide therapeutic agent.

A wide array of conventional compounds have been shown to have anti-neoplastic or anti-cancer activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a therapeutic agent disclosed herein is administered in combination with another conventional anti-neoplastic agent, either concomitantly or sequentially, such therapeutic agent may enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

According to the present disclosure, the polypeptide therapeutic agents described herein may be used in combination with other compositions and procedures for the treatment of diseases. For example, a tumor may be treated conventionally with surgery, radiation or chemotherapy combined with the TβRII polypeptide, and then the TβRII polypeptide may be subsequently administered to the patient to extend the dormancy of micrometastases and to stabilize any residual primary tumor.

In certain aspects of the invention, other therapeutic agents useful for combination tumor therapy with a TβRII polypeptide include other cancer therapies: e.g., surgery, cytotoxic agents, radiological treatments involving irradiation or administration of radioactive substances, chemotherapeutic agents, anti-hormonal agents, growth inhibitory agents, anti-neoplastic compositions, and treatment with anti-cancer agents listed herein and known in the art, or combinations thereof.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxy-doxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chlorambucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY1 17018, onapristone, and FARESTON® toremifene; anti-progesterones; estrogen receptor down-regulators (ERDs); agents that function to suppress or shut down the ovaries, for example, luteinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, ARO-MASIN® exemestane, formestane, fadrozole, RIVIS OR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROC AL® etidronate, NE-58095, ZOMET A® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LUR-TOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

In still other embodiments, TβRII polypeptides may be useful in the treatment or prevention of fibrosis. As used herein, the term "fibrosis" refers to the aberrant formation or development of excess fibrous connective tissue by cells in an organ or tissue. Although processes related to fibrosis can occur as part of normal tissue formation or repair, dysregulation of these processes can lead to altered cellular composition and excess connective tissue deposition that progressively impairs to tissue or organ function. The formation of fibrous tissue can result from a reparative or reactive process. Fibrotic disorders or conditions include, but are not limited to, fibroproliferative disorders associated with vascular diseases, such as cardiac disease, cerebral disease, and peripheral vascular disease, as well as tissues and organ systems including the heart, skin, kidney, peritoneum, gut, and liver (as disclosed in, e.g., Wynn, 2004, Nat Rev 4:583-594, incorporated herein by reference). Exemplary disorders that can be treated include, but are not limited to, renal fibrosis, including nephropathies associated with injury/fibrosis, e.g., chronic nephropathies associated with diabetes (e.g., diabetic nephropathy), lupus, scleroderma, glomerular nephritis, focal segmental glomerular sclerosis, and IgA nephropathy; gut fibrosis, e.g., scleroderma, and radiation-induced gut fibrosis; liver fibrosis, e.g., cirrhosis, alcohol-induced liver fibrosis, biliary duct injury, primary biliary cirrhosis, infection or viral-induced liver fibrosis, congenital hepatic fibrosis and autoimmune hepatitis; and other fibrotic conditions, such as cystic fibrosis, endomyocardial fibrosis, mediastinal fibrosis, sarcoidosis, scleroderma, spinal cord injury/fibrosis, myelofibrosis, vascular restenosis, atherosclerosis, injection fibrosis (which can occur as a complication of intramuscular injections, especially in children), endomyocardial fibrosis, retroperitoneal fibrosis, and nephrogenic systemic fibrosis.

As used herein, the terms "fibrotic disorder", "fibrotic condition," and "fibrotic disease," are used interchangeably to refer to a disorder, condition or disease characterized by fibrosis. Examples of fibrotic disorders include, but are not limited to sclerotic disorders (e.g., scleroderma, atherosclerosis, diffuse systemic sclerosis), vascular fibrosis, pancreatic fibrosis, liver fibrosis (e.g., cirrhosis), renal fibrosis, musculoskeletal fibrosis, cardiac fibrosis (e.g., endomyocardial fibrosis, idiopathic myocardiopathy), skin fibrosis (e.g., scleroderma, post-traumatic, operative cutaneous scarring, keloids and cutaneous keloid formation), eye fibrosis (e.g., glaucoma, sclerosis of the eyes, conjunctival and corneal scarring, and pterygium), myelofibrosis, progressive systemic sclerosis (PSS), chronic graft-versus-host disease, Peyronie's disease, post-cystoscopic urethral stenosis, idiopathic and pharmacologically induced retroperitoneal fibrosis, mediastinal fibrosis, proliferative fibrosis, neoplastic fibrosis, Dupuytren's disease, strictures, neural scarring, dermal scarring and radiation induced fibrosis.

As used herein, inhibition of the fibrotic response of a cell, includes, but is not limited to the inhibition of the fibrotic response of one or more cells within the liver (or liver tissue); one or more cells within the kidney (or renal tissue); one or more cells within muscle tissue; one or more cells within the heart (or cardiac tissue); one or more cells within the pancreas; one or more cells within the skin; one or more cells within the bone, one or more cells within the vasculature, one or more stem cells, or one or more cells within the eye.

The present invention contemplates the use of TβRII polypeptides in combination with one or more other therapeutic modalities. Thus, in addition to the use of TβRII polypeptides, one may also administer to the subject one or more "standard" therapies for treating fibrotic disorders. For example, the TβRII polypeptides can be administered in combination with (i.e., together with) cytotoxins, immunosuppressive agents, radiotoxic agents, and/or therapeutic antibodies. Particular co-therapeutics contemplated by the present invention include, but are not limited to, steroids (e.g., corticosteroids, such as Prednisone), immune-suppressing and/or anti-inflammatory agents (e.g., gamma-interferon, cyclophosphamide, azathioprine, methotrexate, penicillamine, cyclosporine, colchicine, antithymocyte globulin, mycophenolate mofetil, and hydroxychloroquine), cytotoxic drugs, calcium channel blockers (e.g., nifedipine), angiotensin converting enzyme inhibitors (ACE) inhibitors, para-aminobenzoic acid (PABA), dimethyl sulfoxide, transforming growth factor beta (TGFβ) inhibitors, interleukin-5 (IL-5) inhibitors, and pan caspase inhibitors.

Additional anti-fibrotic agents that may be used in combination with TβRII polypeptides include, but are not limited to, lectins (as described in, for example, U.S. Pat. No. 7,026,283, the entire contents of which is incorporated herein by reference), as well as the anti-fibrotic agents described by Wynn et al (2007, J Clin Invest 117:524-529, the entire contents of which is incorporated herein by reference). For example, additional anti-fibrotic agents and therapies include, but are not limited to, various anti-inflammatory/immunosuppressive/cytotoxic drugs (including colchicine, azathioprine, cyclophosphamide, prednisone, thalidomide, pentoxifylline and theophylline), TGFβ signaling modifiers (including relaxin, SMAD7, HGF, and BMP7, as well as TGFβ1, TβRI, TβRII, EGR-I, and CTGF inhibitors), cytokine and cytokine receptor antagonists (inhibitors of IL-1β, IL-5, IL-6, IL-13, IL-21, IL-4R, IL-13Rα1, GM-CSF, TNF-α, oncostatin M, WISP-I, and PDGFs), cytokines and chemokines (IFN-γ, IFN-α/β, IL-12, IL-10, HGF, CXCL10, and CXCL11), chemokine antagonists (inhibitors of CXCL1, CXCL2, CXCL12, CCL2, CCL3, CCL6, CCL17, and CCL18), chemokine receptor antagonists (inhibitors of CCR2, CCR3, CCR5, CCR7, CXCR2, and CXCR4), TLR antagonists (inhibitors of TLR3, TLR4, and TLR9), angiogenesis antagonists (VEGF-specific antibodies and adenosine deaminase replacement therapy), antihypertensive drugs (beta blockers and inhibitors of ANG 11, ACE, and aldosterone), vasoactive substances (ET-1 receptor antagonists and bosetan), inhibitors of the enzymes that synthesize and process collagen (inhibitors of prolyl hydroxylase), B cell antagonists (rituximab), integrin/adhesion molecule antagonists (molecules that block α1β1 and αvβ6 integrins, as well as inhibitors of integrin-linked kinase, and antibodies specific for ICAM-I and VCAM-I), proapoptotic drugs that target myofibroblasts, MMP inhibitors (inhibitors of MMP2, MMP9, and MMP12), and TIMP inhibitors (antibodies specific for TIMP-1).

The TβRII polypeptide and the co-therapeutic agent or co-therapy can be administered in the same formulation or separately. In the case of separate administration, the TβRII polypeptide can be administered before, after, or concurrently with the co-therapeutic or co-therapy. One agent may precede or follow administration of the other agent by intervals ranging from minutes to weeks. In embodiments where two or more different kinds of therapeutic agents are applied separately to a subject, one would generally ensure that a significant period of time did not expire between the time of each delivery, such that these different kinds of agents would still be able to exert an advantageously combined effect on the target tissues or cells.

8. Pharmaceutical Compositions

The therapeutic agents described herein (e.g., TβRII polypeptides) may be formulated into pharmaceutical compositions. Pharmaceutical compositions for use in accordance with the present disclosure may be formulated in conventional manner using one or more physiologically acceptable carriers or excipients. Such formulations will generally be substantially pyrogen-free, in compliance with most regulatory requirements.

In certain embodiments, the therapeutic method of the disclosure includes administering the composition systemically, or locally as an implant or device. When administered, the therapeutic composition for use in this disclosure is in a pyrogen-free, physiologically acceptable form. Therapeutically useful agents other than the TβRII signaling antagonists which may also optionally be included in the composition as described above, may be administered simultaneously or sequentially with the subject compounds (e.g., TβRII polypeptides) in the methods disclosed herein.

Typically, protein therapeutic agents disclosed herein will be administered parentally, and particularly intravenously or subcutaneously. Pharmaceutical compositions suitable for parenteral administration may comprise one or more TβRII polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions and formulations may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration Further, the composition may be encapsulated or injected in a form for delivery to a target tissue site. In certain embodiments, compositions of the present invention may include a matrix capable of delivering one or more therapeutic compounds (e.g., TβRII polypeptides) to a target tissue site, providing a structure for the developing tissue and optimally capable of being resorbed into the body. For example, the matrix may provide slow release of the TβRII polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., TβRII polypeptides). The various factors include, but are not limited to, the patient's age, sex, and diet, the severity disease, time of administration, and other clinical factors. Optionally, the dosage may vary with the type of matrix used in the reconstitution and the types of compounds in the composition. The addition of other known growth factors to the final composition, may also affect the dosage. Progress can be monitored by periodic assessment of bone growth and/or repair, for example, X-rays (including DEXA), histomorphometric determinations, and tetracycline labeling.

In certain embodiments, the present invention also provides gene therapy for the in vivo production of TβRII polypeptides. Such therapy would achieve its therapeutic effect by introduction of the TβRII polynucleotide sequences into cells or tissues having the disorders as listed above. Delivery of TβRII polynucleotide sequences can be achieved using a recombinant expression vector such as a chimeric virus or a colloidal dispersion system. Preferred for therapeutic delivery of TβRII polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the TβRII polynucleotide. In a preferred embodiment, the vector is targeted to bone or cartilage.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for TβRII polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and di stearoylphosphatidylcholine. The targeting of liposomes is also possible based on, for example, organ-specificity, cell-specificity, and organelle-specificity and is known in the art.

The disclosure provides formulations that may be varied to include acids and bases to adjust the pH; and buffering agents to keep the pH within a narrow range.

EXEMPLIFICATION

The invention now being generally described, it will be more readily understood by reference to the following examples, which are included merely for purposes of illustration of certain embodiments of the present invention, and are not intended to limit the invention.

Example 1

Generation of Bioactive GDF15

GDF15 (also known as macrophage-inhibitory cytokine-1) has not been shown biochemically to bind or interact directly with any receptor. Applicants first tried without success to identify a native receptor with high-affinity binding to GDF15 using commercially available human GDF15 (R&D Systems) produced in mammalian CHO cells. Like other ligands in the TGFβ superfamily, which contain a characteristic cysteine knot motif, mature GDF15 is synthesized with a larger prodomain (Harrison et al., Growth Factors 29:174, 2011; Shi et al., Nature 474:343, 2011) that is removed through cleavage by a furin-like protease at the canonical RXXR site to generate mature dimeric GDF15. Since inadequate or inappropriate ligand purification could be a potential reason for inactivity of commercially available GDF15, Applicants tested different purification procedures for GDF15.

Stable Expression of GDF15 in CHO Cells

Applicants used CHO cells to express human GDF15 (hGDF15) and murine GDF15 (mGDF15) for further studies. The amino acid sequence of native precursor for hGDF15 is shown in FIG. 1, and a corresponding nucleotide sequence (with a silent, single nucleotide substitution compared to the native sequence) is shown in FIG. 2. The native amino acid and nucleotide sequences for mGDF15 precursor are shown in FIGS. 3 and 4, respectively. For expression in CHO cells, UCOE™-based constructs encoding human or murine GDF15 precursor were stably transfected into a CHO-PACE cell line. Clones were selected in methotrexate levels of 10 nM, 20 nM, and 50 nM, and any clones that formed colonies (one or two per methotrexate concentration) were then pooled. No gene amplification was performed since it is difficult to amplify UCOE™ pools while maintaining stability of expression. Instead of dilution cloning, high-expressing pools were identified and used for generating hGDF15 and mGDF15.

Purification of Human GDF15

To begin purification, conditioned media from CHO cells stably expressing hGDF15 was adjusted to pH 4.7 with acetic acid. After incubation of media for 10 min at ambient temperature, precipitate was removed by centrifugation. Supernatant was filtered with a 0.8 μm disposable filter. An SP Sepharose™ Fast Flow column (GE Healthcare) was equilibrated with buffers A (20 mM sodium acetate, pH 4.7) and B (20 mM sodium acetate, 1M NaCl, pH 4.7). Loading was performed at 100 cm/hr. The column was washed with 20% B (200 mM NaCl) until no more protein eluted from the column and then washed back to 0% B to remove any residual salt. Protein was eluted with 50 mM Tris, 6M urea, pH 8.0 (Tris+urea pool) until no more protein eluted from the column, followed by elution with 50 mM Tris, 6M urea, 1M NaCl, pH 8.0 (Tris+urea+salt pool). Each pool was dialyzed in 50 mM 4-morpholineethanesulfonic acid (MES, pH 6.5) overnight at 4° C.

GDF15 found in the Tris+urea+salt pool was degraded based on Western blot analysis, so this pool was discarded. The Tris+urea pool was loaded on a Q Sepharose™ Fast Flow column (GE Healthcare) previously equilibrated with buffers A (50 mM MES, pH 6.5) and B (50 mM MES, 1M NaCl, pH 6.5). The flow-through was collected, and the column was washed with 10% B (100 mM NaCl), followed by a 10-50% B gradient (100-500 mM NaCl) over five column volumes at 120 cm/hr. After evaluation of the flow-through and wash fractions by Western blot, protein was found mainly in the flow-through. The flow-through was injected on a reverse-phase preparative C4 column (Vydac) attached to a HPLC, with buffers A (water/0.1% TFA) and B (acetonitrile/0.1% TFA). A 25-40% B gradient over 1 h at 4.5 mL/min produced the best resolution. Collected fractions were evaluated by SDS-PAGE gel (Sypro Ruby) and Western blot to select those for concentration in a centrifugal evaporator.

Purification of Murine GDF15

The pH of the conditioned media was adjusted to pH 4.7 with acetic acid. After incubation of media for 10 min at ambient temperature, precipitate was removed by centrifugation. Supernatant was filtered with a 0.8 μm disposable filter. An SP Sepharose™ Fast Flow column (GE Healthcare) was equilibrated with buffers A (20 mM sodium acetate, pH 4.7) and B (20 mM sodium acetate, 1M NaCl, pH 4.7). Loading was performed at 100-150 cm/hr, and the column was washed with buffer A until no more protein eluted from the column. A wash was performed at 60% B (600 mM NaCl) for 3-4 column volumes, followed by elution with 100% B (1M NaCl) for 3-4 column volumes. Elution continued with 50 mM Tris, 6M urea, pH 8.0, to remove any protein still bound to the resin.

Non-reduced samples of SP-column fractions were analyzed by Western blot. Although most protein was found in the Tris-eluted fractions, previous experiments have indicated that mGDF15 found in these fractions is essentially inactive, so it was not used for further purification. Instead, purification was continued with protein found in the 100% B elution (salt-elution pool). This pool was injected on a reverse-phase preparative C4 column (Vydac) attached to a HPLC. Buffer A was water/0.1% TFA and buffer B was acetonitrile/0.1% TFA. Protein was eluted with a 25-40% B gradient over 1 h at 4.5 mL/min. After evaluation of the reverse-phase column fractions by SDS-PAGE gel (Sypro Ruby) and Western blot, the fractions containing pure mGDF15 were pooled and concentrated in a centrifugal evaporator.

The identities of hGDF15 and mGDF15 were each confirmed by N-terminal sequencing. Both types of purified GDF15 stimulated SMAD2/3 phosphorylation in two different cell lines, thereby providing confirmation of ligand activity.

Example 2

Identification of a TGFβ Superfamily Receptor with High-affinity Binding to GDF15

Once active GDF15 protein was obtained, receptor-Fc fusion proteins comprising TGFβ superfamily receptors were screened for binding to human or murine GDF15 that was generated and purified as described in Example 1. These fusion proteins incorporated an IgG1 Fc domain and were either purchased from R&D Systems or generated in-house. Among the five type II receptors (TGFβ receptor type II, activin receptor type IIA, activin receptor type IIB, BMP receptor type II, and MIS receptor type II), only TGFβ receptor type II (TβRII) exhibited detectable binding to GDF15 ($k_a$=2.92×10$^5$ M$^{-1}$s$^{-1}$; $k_d$=0.001 s$^{-1}$), as determined by surface plasmon resonance with captured receptor-Fc fusion proteins. hGDF15 bound to captured hTβRII-Fc at 37° C. with an equilibrium dissociation constant ($K_D$) of 9.56 nM. None of the seven type I receptors (ALK1, ALK2, ALK3, ALK4, ALK5, ALK6, and ALK7) displayed detectable binding to GDF15 (mGDF15 at 20 nM or 200 nM).

Human TβRII occurs naturally in at least two isoforms—A (long) and B (short)—generated by alternative splicing in the extracellular domain (ECD) (FIGS. 5, 6). The hTβRII-hG1Fc fusion protein (R&D Systems) used for the screening described above incorporates the wild-type TβRII$_{short}$ isoform. In a follow-up analysis, the affinity of mGDF15 binding to a fusion protein incorporating the wild-type TβRII$_{long}$ isoform (R&D Systems) was found by surface plasmon resonance to be very similar to that of the fusion protein incorporating the TβRII$_{short}$ isoform ($K_D$s at 37° C. were 2.7 nM and 4.8 nM, respectively). Having observed general equivalence of these short and long isoforms with regard to GDF15 binding, Applicants then generated a receptor-Fc fusion protein consisting of the wild-type ECD of hTβRII$_{short}$ (SEQ ID NO: 7) fused at its C-terminus with a human IgG2 Fc domain via a minimal linker. Unless noted otherwise, amino acid position numbering with regard to variants based on the TβRII short and long isoforms refers to the corresponding position in the native precursors, SEQ ID NO: 5 and SEQ ID NO: 6, respectively.

Given the high-affinity binding of TβRII to GDF15, we tested whether TβRII could be used as an inhibitor of GDF15. The fusion protein hTβRII$_{short}$(23-159)-hG2Fc was tested in A549 cells transfected with a reporter gene containing a CAGA-12 promoter construct and was found to inhibit hGDF15-induced gene activation in such cells with an IC$_{50}$ of 0.15-0.5 nM. Potent inhibition of GDF15 signaling by the hTβRII$_{short}$ ECD provides additional evidence that TβRII is the high-affinity receptor for GDF15. Even though GDF15 exhibited no detectable binding to ALK5 under cell-free conditions, suppression of endogenous ALK5 mRNA by siRNA methodology markedly reduced mGDF15-mediated signaling in A549 cells (a human pulmonary epithelial cell line) compared to control treatment. In contrast, suppression of other type I receptors (ALK2, ALK3, ALK4, and ALK7) by siRNA methodology failed to alter GDF15-mediated signaling in A549 cells. This result indicates that the GDF15 ternary signaling complex includes ALK5 (TGFβ receptor type I) as its type I receptor and thus provides corroborating evidence for TβRII as a functional type II receptor for GDF15.

Example 3

Generation of Receptor Fusion Protein Variants

TβRII ECD Variants

Since TβRII also binds with high affinity to TGFβ1 and TGFβ3, native TβRII-Fc fusion protein affects signaling of these ligands as well as GDF15. While in some therapeutic settings this broader spectrum of ligand binding may be advantageous, in other settings a more selective molecule may be superior. Therefore, Applicants sought polypeptides with enhanced or reduced selectivity for GDF15 by generating fusion proteins comprising variants of human TβRII ECD. The wild-type hTβRII$_{short}$ (23-159) sequence shown below (SEQ ID NO: 7) served as the basis for five receptor ECD variants listed below (SEQ ID NO: 8-12). A wild type hTβRII$_{short}$ (23-159) was fused to an Fc portion of IgG2 to generate a novel, base Fc fusion construct. See SEQ ID Nos. 50, 51 and 52, below.

```
                                                         (SEQ ID NO: 7)
        1    TIPPHVQKSV NNDMIVTDNN GAVKFPQLCK FCDVRFSTCD NQKSCMSNCS

51   ITSICEKPQE VCVAVWRKND ENITLETVCH DPKLPYHDFI LEDAASPKCI

101  MKEKKKPGET FFMCSCSSDE CNDNIIFSEE YNTSNPD
```

(1) The hTβRII$_{short}$ (23-159/D110K) amino acid sequence shown below (SEQ ID NO: 8), in which the substituted residue is underlined.

```
                                                         (SEQ ID NO: 8)
        1    TIPPHVQKSV NNDMIVTDNN GAVKFPQLCK FCDVRFSTCD NQKSCMSNCS

51   ITSICEKPQE VCVAVWRKND ENITLETVCH DPKLPYHKFI LEDAASPKCI

101  MKEKKKPGET FFMCSCSSDE CNDNIIFSEE YNTSNPD
```

(2) The N-terminally truncated hTβRII$_{short}$ (29-159) amino acid sequence shown below (SEQ ID NO: 9).

```
                                                         (SEQ ID NO: 9)
        1    QKSVNNDMIV TDNNGAVKFP QLCKFCDVRF STCDNQKSCM SNCSITSICE

51   KPQEVCVAVW RKNDENITLE TVCHDPKLPY HDFILEDAAS PKCIMKEKKK

101  PGETFFMCSC SSDECNDNII FSEEYNTSNP D
```

(3) The N-terminally truncated hTβRII$_{short}$ (35-159) amino acid sequence shown below (SEQ ID NO: 10).

```
                                                    (SEQ ID NO: 10)
  1    DMIVTDNNGA VKFPQLCKFC DVRFSTCDNQ KSCMSNCSIT SICEKPQEVC

51    VAVWRKNDEN ITLETVCHDP KLPYHDFILE DAASPKCIMK EKKKPGETFF

101    MCSCSSDECN DNIIFSEEYN TSNPD
```

(4) The C-terminally truncated hTβRII$_{short}$ (23-153) amino acid sequence shown below (SEQ ID NO: 11).

```
                                                    (SEQ ID NO: 11)
  1    TIPPHVQKSV NNDMIVTDNN GAVKFPQLCK FCDVRFSTCD NQKSCMSNCS

51    ITSICEKPQE VCVAVWRKND ENITLETVCH DPKLPYHDFI LEDAASPKCI

101    MKEKKKPGET FFMCSCSSDE CNDNIIFSEE Y
```

(5) The C-terminally truncated hTβRII$_{short}$ (23-153/N70D) amino acid sequence shown below (SEQ ID NO: 12), in which the substituted residue is underlined.

```
                                                    (SEQ ID NO: 12)
  1    TIPPHVQKSV NNDMIVTDNN GAVKFPQLCK FCDVRFSTCD NQKSCMSDCS

51    ITSICEKPQE VCVAVWRKND ENITLETVCH DPKLPYHDFI LEDAASPKCI

101    MKEKKKPGET FFMCSCSSDE CNDNIIFSEE Y
```

Applicants also envision five corresponding variants (SEQ ID NO: 14-17) based on the wild-type hTβRII$_{long}$ (23-184) sequence shown below (SEQ ID NO: 13), in which the 25 amino-acid insertion is underlined. Note that splicing results in a conservative amino acid substitution (Val→Ile) at the flanking position C-terminal to the insertion. Sequence relationships among several hTβRII$_{short}$ variants and their hTβRII$_{long}$ counterparts are indicated in FIG. 7.

```
                                                    (SEQ ID NO: 13)
  1    TIPPHVQKSD VEMEAQKDEI ICPSCNRTAH PLRHINNDMI VTDNNGAVKF

51    PQLCKFCDVR FSTCDNQKSC MSNCSITSIC EKPQEVCVAV WRKNDENITL

101    ETVCHDPKLP YHDFILEDAA SPKCIMKEKK KPGETFFMCS CSSDECNDNI

151    IFSEEYNTSN PD
```

(1) The hTβRII$_{long}$ (23-184/D135K) amino acid sequence shown below (SEQ ID NO: 14), in which the substituted residue is double underlined.

```
                                                    (SEQ ID NO: 14)
  1    TIPPHVQKSD VEMEAQKDEI ICPSCNRTAH PLRHINNDMI VTDNNGAVKF

51    PQLCKFCDVR FSTCDNQKSC MSNCSITSIC EKPQEVCVAV WRKNDENITL

101    ETVCHDPKLP YHKFILEDAA SPKCIMKEKK KPGETFFMCS CSSDECNDNI

151    IFSEEYNTSN PD
```

(2) The N-terminally truncated hTβRII$_{long}$ (29-184) amino acid sequence shown below (SEQ ID NO: 15).

```
                                                    (SEQ ID NO: 15)
  1    QKSDVEMEAQ KDEIICPSCN RTAHPLRHIN NDMIVTDNNG AVKFPQLCKF

51    CDVRFSTCDN QKSCMSNCSI TSICEKPQEV CVAVWRKNDE NITLETVCHD

101    PKLPYHDFIL EDAASPKCIM KEKKKPGETF FMCSCSSDEC NDNIIFSEEY

151    NTSNPD
```

(3) The N-terminally truncated hTβRII$_{long}$ (60-184) amino acid sequence shown below (same as SEQ ID NO: 10).

```
                                               (same as SEQ ID NO: 10)
  1    DMIVTDNNGA VKFPQLCKFC DVRFSTCDNQ KSCMSNCSIT SICEKPQEVC

51    VAVWRKNDEN ITLETVCHDP KLPYHDFILE DAASPKCIMK EKKKPGETFF

101    MCSCSSDECN DNIIFSEEYN TSNPD
```

(4) The C-terminally truncated hTβRII$_{long}$ (23-178) amino acid sequence shown below (SEQ ID NO: 16).

```
                                                       (SEQ ID NO: 16)
  1    TIPPHVQKSD VEMEAQKDEI ICPSCNRTAH PLRHINNDMI VTDNNGAVKF

51    PQLCKFCDVR FSTCDNQKSC MSNCSITSIC EKPQEVCVAV WRKNDENITL

101    ETVCHDPKLP YHDFILEDAA SPKCIMKEKK KPGETFFMCS CSSDECNDNI

151    IFSEEY
```

(5) The C-terminally truncated hTβRII$_{long}$ (23-178/N95D) amino acid sequence shown below (SEQ ID NO: 17), in which the substituted residue is double underlined.

```
                                                       (SEQ ID NO: 17)
  1    TIPPHVQKSD VEMEAQKDEI ICPSCNRTAH PLRHINNDMI VTDNNGAVKF

51    PQLCKFCDVR FSTCDNQKSC MSDCSITSIC EKPQEVCVAV WRKNDENITL

101    ETVCHDPKLP YHDFILEDAA SPKCIMKEKK KPGETFFMCS CSSDECNDNI

151    IFSEEY
```

Additional TβRII ECD variants include:
(A) The N- and C-terminally truncated hTβRII$_{short}$ (35-153) or hTβRII$_{long}$ (60-178) amino acid sequence shown below (SEQ ID NO: 47).

```
                                                       (SEQ ID NO: 47)
  1    DMIVTDNNGA VKFPQLCKFC DVRFSTCDNQ KSCMSNCSIT SICEKPQEVC

51    VAVWRKNDEN ITLETVCHDP KLPYHDFILE DAASPKCIMK EKKKPGETFF

101    MCSCSSDECN DNIIFSEEY
```

(B) The N- and C-terminally truncated hTβRII$_{short}$ (29-153) amino acid sequence shown below (SEQ ID NO: 48).

```
                                                       (SEQ ID NO: 48)
  1    QKSVNNDMIV TDNNGAVKFP QLCKFCDVRF STCDNQKSCM SNCSITSICE

51    KPQEVCVAVW RKNDENITLE TVCHDPKLPY HDFILEDAAS PKCIMKEKKK

101    PGETFFMCSC SSDECNDNII FSEEY
```

(C) The N- and C-terminally truncated hTβRII$_{long}$ (29-178) amino acid sequence shown below (SEQ ID NO: 49).

```
                                                       (SEQ ID NO: 49)
  1    QKSDVEMEAQ KDEIICPSCN RTAHPLRHIN NDMIVTDNNG AVKFPQLCKF

51    CDVRFSTCDN QKSCMSNCSI TSICEKPQEV CVAVWRKNDE NITLETVCHD

101    PKLPYHDFIL EDAASPKCIM KEKKKPGETF FMCSCSSDEC NDNIIFSEEY
```

Any of the above variants (SEQ ID NO: 8-12, 14-17, and 47-49) could incorporate an insertion of 36 amino acids (SEQ ID NO: 18) between the pair of glutamate residues (positions 151 and 152 of SEQ ID NO: 5, or positions 176 and 177 of SEQ ID NO: 6) located near the C-terminus of the hTβRII ECD, as occurs naturally in the hTβRII isoform C (Konrad et al., BMC Genomics 8:318, 2007).

GRCKIRHIGS NNRLQRSTCQ NTGWESAHVM KTPGFR (SEQ ID NO: 18)

As an example, the paired glutamate residues flanking the optional insertion site are denoted below (underlined) for the hTβRII$_{short}$ (29-159) variant (SEQ ID NO: 9).

```
                                                    (SEQ ID NO: 9)
  1 QKSVNNDMIV TDNNGAVKFP QLCKFCDVRF STCDNQKSCM SNCSITSICE

51 KPQEVCVAVW RKNDENITLE TVCHDPKLPY HDFILEDAAS PKCIMKEKKK

101 PGETFFMCSC SSDECNDNII FSEEYNTSNP D
```

Fc Domain Variants hTβRII-hFc fusion proteins were generated in which five hTβRII$_{short}$ variants described above were each fused at their C-terminus (via a minimal linker) to a human IgG2 Fc domain, which has the following amino acid sequence (SEQ ID NO: 19):

```
                                                   (SEQ ID NO: 19)
  1 VECPPCPAPP VAGPSVFLFP PKPKDTLMIS RTPEVTCVVV DVSHEDPEVQ

51 FNWYVDGVEV HNAKTKPREE QFNSTFRVVS VLTVVHQDWL NGKEYKCKVS

101 NKGLPAPIEK TISKTKGQPR EPQVYTLPPS REEMTKNQVS LTCLVKGFYP

151 SDIAVEWESN GQPENNYKTT PPMLDSDGSF FLYSKLTVDK SRWQQGNVFS

201 CSVMHEALHN HYTQKSLSLS PGK
```

Applicants envision hTβRII-hFc fusion proteins comprising alternative Fc domains, including full-length human IgG1 Fc (hG1Fc) (SEQ ID NO: 20, below) and N-terminally truncated human IgG1 Fc (hG1Fc$_{short}$) (SEQ ID NO: 21, below). Optionally, a polypeptide unrelated to an Fc domain could be attached in place of the Fc domain.

```
                                                        (SEQ ID NO: 20)
  1    GGPKSCDKTH TCPPCPAPEL LGGPSVFLFP PKPKDTLMIS RTPEVTCVVV

51    DVSHEDPEVK FNWYVDGVEV HNAKTKPREE QYNSTYRVVS VLTVLHQDWL

101    NGKEYKCKVS NKALPAPIEK TISKAKGQPR EPQVYTLPPS REEMTKNQVS

151    LTCLVKGFYP SDIAVEWESN GQPENNYKTT PPVLDSDGSF FLYSKLTVDK

201    SRWQQGNVFS CSVMHEALHN HYTQKSLSLS PGK (SEQ ID NO: 21)
  1    THTCPPCPAP ELLGGPSVFL FPPKPKDTLM ISRTPEVTCV VVDVSHEDPE

51    VKFNWYVDGV EVHNAKTKPR EEQYNSTYRV VSVLTVLHQD WLNGKEYKCK

101    VSNKALPAPI EKTISKAKGQ PREPQVYTLP PSREEMTKNQ VSLTCLVKGF

151    YPSDIAVEWE SNGQPENNYK TTPPVLDSDG SFFLYSKLTV DKSRWQQGNV

201    FSCSVMHEAL HNHYTQKSLS LSPGK
```

Leader Sequence Variants

The following three leader sequences were considered:

```
(1) Native:
                                        (SEQ ID NO: 22)
MGRGLLRGLWPLHIVLWTRIAS (2) Tissue plasminogen activator (TPA):
                                        (SEQ ID NO: 23)
MDAMKRGLCCVLLLCGAVFVSP (3) Honey bee melittin (HBML):
                                        (SEQ ID NO: 24)
MKFLVNVALVFMVVYISYIYA
```

Expression of hTβRII-hFc Fusion Proteins

The selected hTβRII-hFc protein variants incorporate the TPA leader and have the unprocessed amino-acid sequences shown in SEQ ID NOs: 25, 29, 33, 37, and 41 (see Example 5). Corresponding nucleotide sequences for these variants are SEQ ID NOs: 26, 30, 34, 38, and 42. Selected hTβRII-hFc variants, each with a G2Fc domain (SEQ ID NO: 19), were expressed in HEK-293 cells and purified from conditioned media by filtration and protein A chromatography. Purity of samples for reporter gene assays was evaluated by SDS-PAGE and Western blot analysis.

Applicants envision additional hTβRII-hFc protein variants with the unprocessed amino-acid sequences shown in SEQ ID NOs: 27, 31, 35, 39, and 43, and corresponding nucleotide sequences shown in SEQ ID NOs: 28, 32, 36, 40, and 44.

The amino acid sequence of the wild-type short construct hTβRII$_{short}$ (23-159)-hG2Fc (SEQ ID NO: 50) is shown below.

```
                                              (SEQ ID NO: 50)
TIPPHVQKSV NNDMIVTDNN GAVKFPQLCK FCDVRFSTCD

NQKSCMSNCS ITSICEKPQE VCVAVWRKND ENITLETVCH

DPKLPYHDFI LEDAASPKCI MKEKKKPGET FFMCSCSSDE
```

```
-continued
CNDNIIFSEE YNTSNPDTGG GVECPPCPAP PVAGPSVFLF

PPKPKDTLMI SRTPEVTCVV VDVSHEDPEV QFNWYVDGVE

VHNAKTKPRE EQFNSTFRVV SVLTVVHQDW LNGKEYKCKV

SNKGLPAPIE KTISKTKGQP REPQVYTLPP SREEMTKNQV

SLTCLVKGFY PSDIAVEWES NGQPENNYKT TPPMLDSDGS

FFLYSKLTVD KSRWQQGNVF SCSVMHEALH NHYTQKSLSL SPGK
```

This protein was expressed from a construct including a TPA leader sequence, as shown below (SEQ ID NO:52). Dotted underline denotes leader, and solid underline denotes linker.

```
                                              (SEQ ID NO: 52)
  1 MDAMKRGLCC VLLLCGAVFV SPGATIPPHV QKSVNNDMIV TDNNGAVKFP

51 QLCKFCDVRF STCDNQKSCM SNCSITSICE KPQEVCVAVW RKNDENITLE

101 TVCHDPKLPY HDFILEDAAS PKCIMKEKKK PGETFFMCSC SSDECNDNII

151 FSEEYNTSNP DTGGGVECPP CPAPPVAGPS VFLFPPKPKD TLMISRTPEV

201 TCVVVDVSHE DPEVQFNWYV DGVEVHNAKT KPREEQFNST FRVVSVLTVV

251 HQDWLNGKEY KCKVSNKGLP APIEKTISKT KGQPREPQVY TLPPSREEMT

301 KNQVSLTCLV KGFYPSDIAV EWESNGQPEN NYKTTPPMLD SDGSFFLYSK

351 LTVDKSRWQQ GNVFSCSVMH EALHNHYTQK SLSLSPGK
```

The nucleic acid sequence encoding SEQ ID NO:52 is shown below:

```
                                              (SEQ ID NO: 51)
  1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 TTAATAACGA CATGATAGTC ACTGACAACA ACGGTGCAGT CAAGTTTCCA

151 CAACTGTGTA AATTTTGTGA TGTGAGATTT TCCACCTGTG ACAACCAGAA

201 ATCCTGCATG AGCAACTGCA GCATCACCTC CATCTGTGAG AAGCCACAGG

251 AAGTCTGTGT GGCTGTATGG AGAAAGAATG ACGAGAACAT AACACTAGAG

301 ACAGTTTGCC ATGACCCCAA GCTCCCCTAC CATGACTTTA TTCTGGAAGA

351 TGCTGCTTCT CCAAAGTGCA TTATGAAGGA AAAAAAAAAG CCTGGTGAGA

401 CTTTCTTCAT GTGTTCCTGT AGCTCTGATG AGTGCAATGA CAACATCATC

451 TTCTCAGAAG AATATAACAC CAGCAATCCT GACACCGGTG GTGGAGTCGA

501 GTGCCCACCG TGCCCAGCAC CACCTGTGGC AGGACCGTCA GTCTTCCTCT

551 TCCCCCCAAA ACCCAAGGAC ACCCTCATGA TCTCCCGGAC CCCTGAGGTC

601 ACGTGCGTGG TGGTGGACGT GAGCCACGAA GACCCCGAGG TCCAGTTCAA

651 CTGGTACGTG GACGGCGTGG AGGTGCATAA TGCCAAGACA AAGCCACGGG

701 AGGAGCAGTT CAACAGCACG TTCCGTGTGG TCAGCGTCCT CACCGTCGTG

751 CACCAGGACT GGCTGAACGG CAAGGAGTAC AAGTGCAAGG TCTCCAACAA

801 AGGCCTCCCA GCCCCCATCG AGAAAACCAT CTCCAAAACC AAAGGGCAGC

851 CCCGAGAACC ACAGGTGTAC ACCCTGCCCC CATCCCGGGA GGAGATGACC

901 AAGAACCAGG TCAGCCTGAC CTGCCTGGTC AAAGGCTTCT ACCCCAGCGA
```

```
 951 CATCGCCGTG GAGTGGGAGA GCAATGGGCA GCCGGAGAAC AACTACAAGA

1001 CCACACCTCC CATGCTGGAC TCCGACGGCT CCTTCTTCCT CTACAGCAAG

1051 CTCACCGTGG ACAAGAGCAG GTGGCAGCAG GGGAACGTCT TCTCATGCTC

1101 CGTGATGCAT GAGGCTCTGC ACAACCACTA CACGCAGAAG AGCCTCTCCC

1151 TGTCTCCGGG TAAA
```

Example 4

Differential Ligand Inhibition by Receptor Fusion Protein Variants in Cell-based Assay A reporter gene assay in A549 cells was used to determine the ability of hTβRII-hFc variants to inhibit activity of GDF15, TGFβ1, TGFβ2, and TGFβ3. This assay is based on a human lung carcinoma cell line transfected with a pGL3 (CAGA)12 reporter plasmid (Dennler et al, 1998, EMBO 17: 3091-3100) as well as a *Renilla* reporter plasmid (pRL-CMV) to control for transfection efficiency. The CAGA motif is present in the promoters of TGFβ-responsive genes (for example, PAI-1), so this vector is of general use for factors signaling through SMAD2 and SMAD3.

On the first day of the assay, A549 cells (ATCC®: CCL-185™) were distributed in 48-well plates at $6.5 \times 10^4$ cells per well. On the second day, a solution containing 10 µg pGL3(CAGA)12, 100 ng pRLCMV, 30 µl X-tremeGENE 9 (Roche Applied Science), and 970 µl OptiMEM (Invitrogen) was preincubated for 30 min, then added to Eagle's minimum essential medium (EMEM, ATCC®) supplemented with 0.1% BSA, which was applied to the plated cells (500 µl/well) for incubation overnight at room temperature. On the third day, medium was removed, and cells were incubated overnight at 37° C. with a mixture of ligands and inhibitors prepared as described below.

Serial dilutions of test articles were made in a 48-well plate in a 200 µl volume of assay buffer (EMEM+0.1% BSA). An equal volume of assay buffer containing the test ligand was added to obtain a final ligand concentration equal to the EC50 determined previously. Human GDF15 and murine GDF15 were generated in-house (see above), while human TGFβ1, human TGFβ2, and human TGFβ3 were obtained from PeproTech. Test solutions were incubated at 37° C. for 30 minutes, then 250 µl of the mixture was added to all wells. Each concentration of test article was determined in duplicate. After incubation with test solutions overnight, cells were rinsed with phosphate-buffered saline, then lysed with passive lysis buffer (Promega E1941) and stored overnight at −70° C. On the fourth and final day, plates were warmed to room temperature with gentle shaking. Cell lysates were transferred in duplicate to a chemiluminescence plate (96-well) and analyzed in a luminometer with reagents from a Dual-Luciferase Reporter Assay system (Promega E1980) to determine normalized luciferase activity.

This assay was used to screen receptor fusion protein variants for potential inhibitory effects on cell signaling by TβRII ligands. Consistent with previous reports concerning wild-type TβRII$_{short}$Fc and TβRII$_{long}$-Fc (del Re et al., J Biol Chem 279:22765, 2004), none of the variants tested were able to inhibit TGFβ2, even at high concentrations. However, hTβRII-hFc variants unexpectedly showed differential inhibition of cellular signaling mediated by GDF15, TGFβ1, and TGFβ3. Compared with wild-type TβRII$_{short}$ (23-159)-G2Fc, the TβRII$_{short}$ (23-159/D110K)-G2Fc variant exhibited potent inhibition of GDF15 but loss of inhibition of TGFβ1 and greatly reduced inhibition (~50 fold) of TGFβ3 (see table below). Position 110 is located in the "hook" region of TβRII (Radaev et al., J Biol Chem 285: 14806, 2010) but has not been suggested to confer selectivity among the recognized TβRII ligands TGFβ1, TGFβ2, and TGFβ3. Thus, this variant displays a profile of differential ligand inhibition in which GDF15 is inhibited most potently, TGFβ1 least potently, and TGFβ3 to an intermediate degree.

|  |  | IC$_{50}$ (nM) | | |
| --- | --- | --- | --- | --- |
|  | Construct | mGDF15 (35 ng/ml) | hTGFβ1 (640 pg/ml) | hTGFβ3 (270 pg/ml) |
| Full-length wild-type ECD | TβRII$_{short}$(23-159)-G2Fc | ~0.12 | 1.73 | 0.14 |
| Full-length ECD with D110K substitution | TβRII$_{short}$(23-159/D110K)-G2Fc | ~0.7 | ND (>73.6) | ~6.9 |

ND, not determined

In a second experiment, potencies of variants with N-terminally truncated TβRII ECD were compared with that of full-length wild-type TβRII ECD. As shown in the table below, TβRII$_{short}$ (29-159)-G2Fc and TβRII$_{short}$ (35-159)-G2Fc displayed a greatly diminished ability to inhibit TGFβ3 but an undiminished (N'Δ6) or only slightly diminished (N'Δ12) ability to inhibit GDF15 compared to TβRII$_{short}$ (23-159)-G2Fc (wild-type). Effects of N-terminal truncation on inhibition of TGFβ1 compared to wild-type were intermediate in magnitude. Thus, these two variants exhibit a profile of differential ligand inhibition in which GDF15 is inhibited most potently, TGFβ3 least potently, and TGFβ1 to an intermediate degree.

|  |  | IC$_{50}$ (nM) | | |
| --- | --- | --- | --- | --- |
|  | Construct | hGDF15 (70 or 112 ng/ml) | hTGFβ1 (640 pg/ml) | hTGFβ3 (270 pg/ml) |
| Full-length wild-type ECD | TβRII$_{short}$(23-159)-G2Fc | 0.14-0.53 | 0.52 | 0.37 |
| N'Δ6 ECD | TβRII$_{short}$(29-159)-G2Fc | 0.40 | 2.05 | ND (>7.5) |
| N'Δ12 ECD | TβRII$_{short}$(35-159)-G2Fc | 0.92 | 2.51 | ND (>7.5) |

ND, not determined

In a third experiment, we determined the effect on potency of a N70D substitution in a C-terminally truncated TβRII ECD. This aspartate residue represents a potential glycosylation site. As shown in the table below, $T\beta RII_{short}$ (23-153/N70D)-G2Fc displayed greatly diminished ability to inhibit TGFβ1 and virtually undiminished ability to inhibit TGFβ3 compared to $T\beta RII_{short}$ (23-153)-G2Fc. Effects of N70D substitution on inhibition of GDF15 compared to both $T\beta RII_{short}$ (23-153)-G2Fc and wild-type were intermediate in magnitude. Thus, the C-terminally truncated variant with N70D substitution exhibits a profile of differential ligand inhibition in which TGFβ3 is inhibited most potently, TGFβ1 least potently, and GDF15 to an intermediate degree.

| | Construct | $IC_{50}$ (nM) hGDF15 (70 ng/ml) | hTGFβ1 (640 pg/ml) | hTGFβ3 (270 pg/ml) |
|---|---|---|---|---|
| Full-length wild-type ECD | $T\beta RII_{short}$(23-159)-G2Fc | 0.14 | ND | ND |
| C'Δ6 ECD | $T\beta RII_{short}$(23-153)-G2Fc | 0.18 | 2.62 | 0.14 |
| C'Δ6 ECD with N70D substitution | $T\beta RII_{short}$(23-153/N70D)-G2Fc | 2.42 | 17.7 | 0.28 |

Together, these results demonstrate that Applicants have generated truncations and mutations of the TβRII ECD that exhibit widely different ligand binding profiles. Notably, this demonstration reveals that properly expressed and purified GDF15 interacts directly with TβRII and can be differentially inhibited by fusion proteins comprising variants of the TβRII ECD. Activity profiles of these variants can be summarized in the following table.

Summary of Ligand Selectivity

| | Construct | Degree of Ligand Inhibition: Potent | Moderate | Negligible |
|---|---|---|---|---|
| Full-length wild-type ECD | $T\beta RII_{short}$(23-159)-G2Fc | GDF15 TGFβ1 TGFβ3 | — | TGFβ2 |
| Full-length ECD with D110K substitution | $T\beta RII_{short}$(23-159/D110K)-G2Fc | GDF15 | TGFβ3 | TGFβ1 TGFβ2 |
| N'Δ6 ECD | $T\beta RII_{short}$(29-159)-G2Fc | GDF15 | TGFβ1 | TGFβ2 TGFβ3 |
| N'Δ12 ECD | $T\beta RII_{short}$(35-159)-G2Fc | GDF15 | TGFβ1 | TGFβ2 TGFβ3 |
| C'Δ6 ECD with N70D substitution | $T\beta RII_{short}$(23-153/N70D)-G2Fc | TGFβ3 | GDF15 | TGFβ1 TGFβ2 |

We predict that the TβRII$_{long}$ ECD counterparts of these TβRII$_{short}$ ECD variants will exhibit similar ligand selectivity. In addition, a C'Δ6 truncated ECD (such as SEQ ID NOs: 11 and 16 for the TβRII$_{short}$ and TβRII$_{long}$ isoforms, respectively) can be used as a base sequence for TβRII$_{short}$ or TβRII$_{long}$ in which to introduce mutations and N-terminal truncations.

Example 5

Exemplary hTβRII-hFc Nucleic Acids and Proteins

This example summarizes nucleic acid constructs that can be used to express TβRII constructs in HEK-293 or CHO cells, according to the methods provided herein in order to provide the proteins isolated from cell culture. In each case the mature protein isolated from cell culture will have the leader sequence (dotted underline in each sequence below) removed.

Item 1 shows the amino acid sequence of hTβRII$_{short}$ (23-159/D110K)-hG2Fc (SEQ ID NO: 25). Double underline indicates D110K substitution. Dotted underline denotes leader, and solid underline denotes linker.

```
                                                          (SEQ ID NO: 25)
  1 MDAMKRGLCC VLLLCGAVFV SPGATIPPHV QKSVNNDMIV TDNNGAVKFP

51 QLCKFCDVRF STCDNQKSCM SNCSITSICE KPQEVCVAVW RKNDENITLE

101 TVCHDPKLPY HKFILEDAAS PKCIMKEKKK PGETFFMCSC SSDECNDNII

151 FSEEYNTSNP DTGGGVECPP CPAPPVAGPS VFLFPPKPKD TLMISRTPEV

201 TCVVVDVSHE DPEVQFNWYV DGVEVHNAKT KPREEQFNST FRVVSVLTVV

251 HQDWLNGKEY KCKVSNKGLP APIEKTISKT KGQPREPQVY TLPPSREEMT

301 KNQVSLTCLV KGFYPSDIAV EWESNGQPEN NYKTTPPMLD SDGSFFLYSK

351 LTVDKSRWQQ GNVFSCSVMH EALHNHYTQK SLSLSPGK
```

Item 2 shows a nucleotide sequence encoding hTβRII$_{short}$ (23-159/D110K)-hG2Fc (SEQ ID NO: 26). Double underline indicates D110K substitution. Dotted underline denotes leader, and solid underline denotes linker.

```
                                                          (SEQ ID NO: 26)
  1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 TTAATAACGA CATGATAGTC ACTGACAACA ACGGTGCAGT CAAGTTTCCA

151 CAACTGTGTA AATTTTGTGA TGTGAGATTT TCCACCTGTG ACAACCAGAA

201 ATCCTGCATG AGCAACTGCA GCATCACCTC CATCTGTGAG AAGCCACAGG

251 AAGTCTGTGT GGCTGTATGG AGAAAGAATG ACGAGAACAT AACACTAGAG

301 ACAGTTTGCC ATGACCCCAA GCTCCCCTAC CATAAGTTTA TTCTGGAAGA

351 TGCTGCTTCT CCAAAGTGCA TTATGAAGGA AAAAAAAAAG CCTGGTGAGA

401 CTTTCTTCAT GTGTTCCTGT AGCTCTGATG AGTGCAATGA CAACATCATC

451 TTCTCAGAAG AATATAACAC CAGCAATCCT GACACCGGTG GTGGAGTCGA

501 GTGCCCACCG TGCCCAGCAC CACCTGTGGC AGGACCGTCA GTCTTCCTCT

551 TCCCCCCAAA ACCCAAGGAC ACCCTCATGA TCTCCCGGAC CCCTGAGGTC

601 ACGTGCGTGG TGGTGGACGT GAGCCACGAA GACCCCGAGG TCCAGTTCAA

651 CTGGTACGTG GACGGCGTGG AGGTGCATAA TGCCAAGACA AAGCCACGGG

701 AGGAGCAGTT CAACAGCACG TTCCGTGTGG TCAGCGTCCT CACCGTCGTG

751 CACCAGGACT GGCTGAACGG CAAGGAGTAC AAGTGCAAGG TCTCCAACAA

801 AGGCCTCCCA GCCCCCATCG AGAAAACCAT CTCCAAAACC AAAGGGCAGC

851 CCCGAGAACC ACAGGTGTAC ACCCTGCCCC CATCCCGGGA GGAGATGACC

901 AAGAACCAGG TCAGCCTGAC CTGCCTGGTC AAAGGCTTCT ACCCCAGCGA
```

-continued
```
 951 CATCGCCGTG GAGTGGGAGA GCAATGGGCA GCCGGAGAAC AACTACAAGA

1001 CCACACCTCC CATGCTGGAC TCCGACGGCT CCTTCTTCCT CTACAGCAAG

1051 CTCACCGTGG ACAAGAGCAG GTGGCAGCAG GGGAACGTCT TCTCATGCTC

1101 CGTGATGCAT GAGGCTCTGC ACAACCACTA CACGCAGAAG AGCCTCTCCC

1151 TGTCTCCGGG TAAA
```

Item 3 shows the amino acid sequence of hTβRII$_{short}$ (23-159/D110K)-hG1Fc$_{short}$ (SEQ ID NO: 27). Double underline indicates D110K substitution. Dotted underline denotes leader, and solid underline denotes linker.

```
                                                  (SEQ ID NO: 27)
  1 MDAMKRGLCC VLLLCGAVFV SPGATIPPHV QKSVNNDMIV TDNNGAVKFP

51 QLCKFCDVRF STCDNQKSCM SNCSITSICE KPQEVCVAVW RKNDENITLE

101 TVCHDPKLPY HKFILEDAAS PKCIMKEKKK PGETFFMCSC SSDECNDNII

151 FSEEYNTSNP DTGGGTHTCP CPAPELLGG PSVFLFPPKP KDTLMISRTP

201 EVTCVVVDVS HEDPEVKFNW YVDGVEVHNA KTKPREEQYN STYRVVSVLT

251 VLHQDWLNGK EYKCKVSNKA LPAPIEKTIS KAKGQPREPQ VYTLPPSREE

301 MTKNQVSLTC LVKGFYPSDI AVEWESNGQP ENNYKTTPPV LDSDGSFFLY

351 SKLTVDKSRW QQGNVFSCSV MHEALHNHYT QKSLSLSPGK
```

Item 4 shows a nucleotide sequence encoding hTβRII$_{short}$ (23-159/D110K)-hG1Fc$_{short}$ (SEQ ID NO: 28). Double underline indicates D110K substitution. Dotted underline denotes leader, and solid underline denotes linker.

```
                                                  (SEQ ID NO: 28)
  1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 TTAATAACGA CATGATAGTC ACTGACAACA ACGGTGCAGT CAAGTTTCCA

151 CAACTGTGTA AATTTTGTGA TGTGAGATTT TCCACCTGTG ACAACCAGAA

201 ATCCTGCATG AGCAACTGCA GCATCACCTC CATCTGTGAG AAGCCACAGG

251 AAGTCTGTGT GGCTGTATGG AGAAAGAATG ACGAGAACAT AACACTAGAG

301 ACAGTTTGCC ATGACCCCAA GCTCCCCTAC CATAAGTTTA TTCTGGAAGA

351 TGCTGCTTCT CCAAAGTGCA TTATGAAGGA AAAAAAAAAG CCTGGTGAGA

401 CTTTCTTCAT GTGTTCCTGT AGCTCTGATG AGTGCAATGA CAACATCATC

451 TTCTCAGAAG AATATAACAC CAGCAATCCT GACACCGGTG GTGGAACTCA

501 CACATGCCCA CCGTGCCCAG CACCTGAACT CCTGGGGGGA CCGTCAGTCT

551 TCCTCTTCCC CCCAAAACCC AAGGACACCC TCATGATCTC CCGGACCCCT

601 GAGGTCACAT GCGTGGTGGT GGACGTGAGC CACGAAGACC CTGAGGTCAA

651 GTTCAACTGG TACGTGGACG GCGTGGAGGT GCATAATGCC AAGACAAAGC

701 CGCGGGAGGA GCAGTACAAC AGCACGTACC GTGTGGTCAG CGTCCTCACC

751 GTCCTGCACC AGGACTGGCT GAATGGCAAG GAGTACAAGT GCAAGGTCTC

801 CAACAAAGCC CTCCCAGCCC CCATCGAGAA AACCATCTCC AAAGCCAAAG

851 GGCAGCCCCG AGAACCACAG GTGTACACCC TGCCCCCATC CCGGGAGGAG
```

-continued
```
 901 ATGACCAAGA ACCAGGTCAG CCTGACCTGC CTGGTCAAAG GCTTCTATCC

951 CAGCGACATC GCCGTGGAGT GGGAGAGCAA TGGGCAGCCG GAGAACAACT

1001 ACAAGACCAC GCCTCCCGTG CTGGACTCCG ACGGCTCCTT CTTCCTCTAT

1051 AGCAAGCTCA CCGTGGACAA GAGCAGGTGG CAGCAGGGGA ACGTCTTCTC

1101 ATGCTCCGTG ATGCATGAGG CTCTGCACAA CCACTACACG CAGAAGAGCC

1151 TCTCCCTGTC CCCGGGTAAA
```

Item 5 shows the amino acid sequence of hTβRII$_{short}$ (29-159)-hG2Fc (SEQ ID NO: 29). Dotted underline denotes leader, and solid underline denotes linker.

```
                                                  (SEQ ID NO: 29)
  1 MDAMKRGLCC VLLLCGAVFV SPGAQKSVNN DMIVTDNNGA VKFPQLCKFC

51 DVRFSTCDNQ KSCMSNCSIT SICEKPQEVC VAVWRKNDEN ITLETVCHDP

101 KLPYHDFILE DAASPKCIMK EKKKPGETFF MCSCSSDECN DNIIFSEEYN

151 TSNPDTGGGV ECPPCPAPPV AGPSVFLFPP KPKDTLMISR TPEVTCVVVD

201 VSHEDPEVQF NWYVDGVEVH NAKTKPREEQ FNSTFRVVSV LTVVHQDWLN

251 GKEYKCKVSN KGLPAPIEKT ISKTKGQPRE PQVYTLPPSR EEMTKNQVSL

301 TCLVKGFYPS DIAVEWESNG QPENNYKTTP PMLDSDGSFF LYSKLTVDKS

351 RWQQGNVFSC SVMHEALHNH YTQKSLSLSP GK
```

Item 6 shows a nucleotide sequence encoding hTβRII$_{short}$ (29-159)-hG2Fc (SEQ ID NO: 30). Dotted underline denotes leader, and solid underline denotes linker.

```
                                                  (SEQ ID NO: 30)
  1 ATGGATGCAA TGAAGAGAGG GCTCTGCTGT GTGCTGCTGC TGTGTGGAGC

51 AGTCTTCGTT TCGCCCGGCG CCCAGAAGTC GGTTAATAAC GACATGATAG

101 TCACTGACAA CAACGGTGCA GTCAAGTTTC CACAACTGTG TAAATTTTGT

151 GATGTGAGAT TTTCCACCTG TGACAACCAG AAATCCTGCA TGAGCAACTG

201 CAGCATCACC TCCATCTGTG AGAAGCCACA GGAAGTCTGT GTGGCTGTAT

251 GGAGAAAGAA TGACGAGAAC ATAACACTAG AGACAGTTTG CCATGACCCC

301 AAGCTCCCCT ACCATGACTT TATTCTGGAA GATGCTGCTT CTCCAAAGTG

351 CATTATGAAG GAAAAAAAAA AGCCTGGTGA GACTTTCTTC ATGTGTTCCT

401 GTAGCTCTGA TGAGTGCAAT GACAACATCA TCTTCTCAGA AGAATATAAC

451 ACCAGCAATC CTGACACCGG TGGTGGAGTC GAGTGCCCAC CGTGCCCAGC

501 ACCACCTGTG GCAGGACCGT CAGTCTTCCT CTTCCCCCCA AAACCCAAGG

551 ACACCCTCAT GATCTCCCGG ACCCCTGAGG TCACGTGCGT GGTGGTGGAC

601 GTGAGCCACG AAGACCCCGA GGTCCAGTTC AACTGGTACG TGGACGGCGT

651 GGAGGTGCAT AATGCCAAGA CAAAGCCACG GGAGGAGCAG TTCAACAGCA

701 CGTTCCGTGT GGTCAGCGTC CTCACCGTCG TGCACCAGGA CTGGCTGAAC

751 GGCAAGGAGT ACAAGTGCAA GGTCTCCAAC AAAGGCCTCC CAGCCCCCAT

801 CGAGAAAACC ATCTCCAAAA CCAAAGGGCA GCCCCGAGAA CCACAGGTGT

851 ACACCCTGCC CCCATCCCGG GAGGAGATGA CCAAGAACCA GGTCAGCCTG

901 ACCTGCCTGG TCAAAGGCTT CTACCCCAGC GACATCGCCG TGGAGTGGGA
```

```
 951 GAGCAATGGG CAGCCGGAGA ACAACTACAA GACCACACCT CCCATGCTGG

1001 ACTCCGACGG CTCCTTCTTC CTCTACAGCA AGCTCACCGT GGACAAGAGC

1051 AGGTGGCAGC AGGGGAACGT CTTCTCATGC TCCGTGATGC ATGAGGCTCT

1101 GCACAACCAC TACACGCAGA AGAGCCTCTC CCTGTCTCCG GGTAAA
```

Item 7 shows the amino acid sequence of hTβRII$_{short}$ (29-159)-hG1Fc$_{short}$ (SEQ ID NO: 31). Dotted underline denotes leader, and solid underline denotes linker.

```
                                                (SEQ ID NO: 31)
  1 MDAMKRGLCC VLLLCGAVFV SPGAQKSVNN DMIVTDNNGA VKFPQLCKFC

51 DVRFSTCDNQ KSCMSNCSIT SICEKPQEVC VAVWRKNDEN ITLETVCHDP

101 KLPYHDFILE DAASPKCIMK EKKKPGETFF MCSCSSDECN DNIIFSEEYN

151 TSNPDTGGGT HTCPPCPAPE LLGGPSVFLF PPKPKDTLMI SRTPEVTCVV

201 VDVSHEDPEV KFNWYVDGVE VHNAKTKPRE EQYNSTYRVV SVLTVLHQDW

251 LNGKEYKCKV SNKALPAPIE KTISKAKGQP REPQVYTLPP SREEMTKNQV

301 SLTCLVKGFY PSDIAVEWES NGQPENNYKT TPPVLDSDGS FFLYSKLTVD

351 KSRWQQGNVF SCSVMHEALH NHYTQKSLSL SPGK
```

Item 8 shows a nucleotide sequence encoding hTβRII$_{short}$ (29-159)-hG1Fc$_{short}$ (SEQ ID NO: 32). Dotted underline denotes leader, and solid underline denotes linker.

```
                                                (SEQ ID NO: 32)
  1 ATGGATGCAA TGAAGAGAGG GCTCTGCTGT GTGCTGCTGC TGTGTGGAGC

51 AGTCTTCGTT TCGCCCGGCG CCCAGAAGTC GGTTAATAAC GACATGATAG

101 TCACTGACAA CAACGGTGCA GTCAAGTTTC CACAACTGTG TAAATTTTGT

151 GATGTGAGAT TTTCCACCTG TGACAACCAG AAATCCTGCA TGAGCAACTG

201 CAGCATCACC TCCATCTGTG AGAAGCCACA GGAAGTCTGT GTGGCTGTAT

251 GGAGAAAGAA TGACGAGAAC ATAACACTAG AGACAGTTTG CCATGACCCC

301 AAGCTCCCCT ACCATGACTT TATTCTGGAA GATGCTGCTT CTCCAAAGTG

351 CATTATGAAG GAAAAAAAAA AGCCTGGTGA GACTTTCTTC ATGTGTTCCT

401 GTAGCTCTGA TGAGTGCAAT GACAACATCA TCTTCTCAGA AGAATATAAC

451 ACCAGCAATC CTGACACCGG TGGTGGAACT CACACATGCC CACCGTGCCC

501 AGCACCTGAA CTCCTGGGGG GACCGTCAGT CTTCCTCTTC CCCCCAAAAC

551 CCAAGGACAC CCTCATGATC TCCCGGACCC CTGAGGTCAC ATGCGTGGTG

601 GTGGACGTGA GCCACGAAGA CCCTGAGGTC AAGTTCAACT GGTACGTGGA

651 CGGCGTGGAG GTGCATAATG CCAAGACAAA GCCGCGGGAG GAGCAGTACA

701 ACAGCACGTA CCGTGTGGTC AGCGTCCTCA CCGTCCTGCA CCAGGACTGG

751 CTGAATGGCA AGGAGTACAA GTGCAAGGTC TCCAACAAAG CCCTCCCAGC

801 CCCCATCGAG AAAACCATCT CCAAAGCCAA AGGGCAGCCC CGAGAACCAC

851 AGGTGTACAC CCTGCCCCCA TCCCGGGAGG AGATGACCAA GAACCAGGTC

901 AGCCTGACCT GCCTGGTCAA AGGCTTCTAT CCCAGCGACA TCGCCGTGGA

951 GTGGGAGAGC AATGGGCAGC CGGAGAACAA CTACAAGACC ACGCCTCCCG

1001 TGCTGGACTC CGACGGCTCC TTCTTCCTCT ATAGCAAGCT CACCGTGGAC
```

-continued

```
1051 AAGAGCAGGT GGCAGCAGGG GAACGTCTTC TCATGCTCCG TGATGCATGA

1101 GGCTCTGCAC AACCACTACA CGCAGAAGAG CCTCTCCCTG TCCCCGGGTA

1151 AA
```

Item 9 shows the amino acid sequence of hTβRII$_{short}$ (35-159)-hG2Fc (SEQ ID NO: 33). Dotted underline denotes leader, and solid underline denotes linker.

```
                                                    (SEQ ID NO: 33)
  1 MDAMKRGLCC VLLLCGAVFV SPGADMIVTD NNGAVKFPQL CKFCDVRFST

51 CDNQKSCMSN CSITSICEKP QEVCVAVWRK NDENITLETV CHDPKLPYHD

101 FILEDAASPK CIMKEKKKPG ETFFMCSCSS DECNDNIIFS EEYNTSNPDT

151 GGGVECPPCP APPVAGPSVF LFPPKPKDTL MISRTPEVTC VVVDVSHEDP

201 EVQFNWYVDG VEVHNAKTKP REEQFNSTFR VVSVLTVVHQ DWLNGKEYKC

251 KVSNKGLPAP IEKTISKTKG QPREPQVYTL PPSREEMTKN QVSLTCLVKG

301 FYPSDIAVEW ESNGQPENNY KTTPPMLDSD GSFFLYSKLT VDKSRWQQGN

351 VFSCSVMHEA LHNHYTQKSL SLSPGK
```

Item 10 shows a nucleotide sequence encoding hTβRII$_{short}$ (35-159)-hG2Fc (SEQ ID NO: 34). Dotted underline denotes leader, and solid underline denotes linker.

```
                                                    (SEQ ID NO: 34)
  1 ATGGATGCAA TGAAGAGAGG GCTCTGCTGT GTGCTGCTGC TGTGTGGAGC

51 AGTCTTCGTT TCGCCCGGCG CCGACATGAT AGTCACTGAC AACAACGGTG

101 CAGTCAAGTT TCCACAACTG TGTAAATTTT GTGATGTGAG ATTTTCCACC

151 TGTGACAACC AGAAATCCTG CATGAGCAAC TGCAGCATCA CCTCCATCTG

201 TGAGAAGCCA CAGGAAGTCT GTGTGGCTGT ATGGAGAAAG AATGACGAGA

251 ACATAACACT AGAGACAGTT TGCCATGACC CAAGCTCCC CTACCATGAC

301 TTTATTCTGG AAGATGCTGC TTCTCCAAAG TGCATTATGA AGGAAAAAAA

351 AAAGCCTGGT GAGACTTTCT TCATGTGTTC CTGTAGCTCT GATGAGTGCA

401 ATGACAACAT CATCTTCTCA GAAGAATATA ACACCAGCAA TCCTGACACC

451 GGTGGTGGAG TCGAGTGCCC ACCGTGCCCA GCACCACCTG TGGCAGGACC

501 GTCAGTCTTC CTCTTCCCCC CAAAACCCAA GGACACCCTC ATGATCTCCC

551 GGACCCCTGA GGTCACGTGC GTGGTGGTGG ACGTGAGCCA CGAAGACCCC

601 GAGGTCCAGT TCAACTGGTA CGTGGACGGC GTGGAGGTGC ATAATGCCAA

651 GACAAAGCCA CGGGAGGAGC AGTTCAACAG CACGTTCCGT GTGGTCAGCG

701 TCCTCACCGT CGTGCACCAG GACTGGCTGA ACGGCAAGGA GTACAAGTGC

751 AAGGTCTCCA ACAAAGGCCT CCCAGCCCCC ATCGAGAAAA CCATCTCCAA

801 AACCAAAGGG CAGCCCCGAG AACCACAGGT GTACACCCTG CCCCCATCCC

851 GGGAGGAGAT GACCAAGAAC CAGGTCAGCC TGACCTGCCT GGTCAAAGGC

901 TTCTACCCCA GCGACATCGC CGTGGAGTGG GAGAGCAATG GGCAGCCGGA

951 GAACAACTAC AAGACCACAC CTCCCATGCT GGACTCCGAC GGCTCCTTCT

1001 TCCTCTACAG CAAGCTCACC GTGGACAAGA GCAGGTGGCA GCAGGGGAAC
```

```
1051 GTCTTCTCAT GCTCCGTGAT GCATGAGGCT CTGCACAACC ACTACACGCA

1101 GAAGAGCCTC TCCCTGTCTC CGGGTAAA
```

Item 11 shows the amino acid sequence of hTβRII$_{short}$ (35-159)-hG1Fc$_{short}$ (SEQ ID NO: 35). Dotted underline denotes leader, and solid underline denotes linker.

```
                                                    (SEQ ID NO: 35)
  1  MDAMKRGLCC VLLLCGAVFV SPGADMIVTD NNGAVKFPQL CKFCDVRFST

51  CDNQKSCMSN CSITSICEKP QEVCVAVWRK NDENITLETV CHDPKLPYHD

101  FILEDAASPK CIMKEKKKPG ETFFMCSCSS DECNDNIIFS EEYNTSNPDT

151  GGGTHTCPPC PAPELLGGPS VFLFPPKPKD TLMISRTPEV TCVVVDVSHE

201  DPEVKFNWYV DGVEVHNAKT KPREEQYNST YRVVSVLTVL HQDWLNGKEY

251  KCKVSNKALP APIEKTISKA KGQPREPQVY TLPPSREEMT KNQVSLTCLV

301  KGFYPSDIAV EWESNGQPEN NYKTTPPVLD SDGSFFLYSK LTVDKSRWQQ

351  GNVFSCSVMH EALHNHYTQK SLSLSPGK
```

Item 12 shows a nucleotide sequence encoding hTβRII$_{short}$ (35-159)-hG1Fc$_{short}$ (SEQ ID NO: 36). Dotted underline denotes leader, and solid underline denotes linker.

```
                                                    (SEQ ID NO: 36)
  1  ATGGATGCAA TGAAGAGAGG GCTCTGCTGT GTGCTGCTGC TGTGTGGAGC

51  AGTCTTCGTT TCGCCCGGCG CCGACATGAT AGTCACTGAC AACAACGGTG

101  CAGTCAAGTT TCCACAACTG TGTAAATTTT GTGATGTGAG ATTTTCCACC

151  TGTGACAACC AGAAATCCTG CATGAGCAAC TGCAGCATCA CCTCCATCTG

201  TGAGAAGCCA CAGGAAGTCT GTGTGGCTGT ATGGAGAAAG AATGACGAGA

251  ACATAACACT AGAGACAGTT TGCCATGACC CCAAGCTCCC CTACCATGAC

301  TTTATTCTGG AAGATGCTGC TTCTCCAAAG TGCATTATGA AGGAAAAAAA

351  AAAGCCTGGT GAGACTTTCT TCATGTGTTC CTGTAGCTCT GATGAGTGCA

401  ATGACAACAT CATCTTCTCA GAAGAATATA ACACCAGCAA TCCTGACACC

451  GGTGGTGGAA CTCACACATG CCCACCGTGC CCAGCACCTG AACTCCTGGG

501  GGGACCGTCA GTCTTCCTCT TCCCCCCAAA ACCCAAGGAC ACCCTCATGA

551  TCTCCCGGAC CCCTGAGGTC ACATGCGTGG TGGTGGACGT GAGCCACGAA

601  GACCCTGAGG TCAAGTTCAA CTGGTACGTG GACGGCGTGG AGGTGCATAA

651  TGCCAAGACA AAGCCGCGGG AGGAGCAGTA CAACAGCACG TACCGTGTGG

701  TCAGCGTCCT CACCGTCCTG CACCAGGACT GGCTGAATGG CAAGGAGTAC

751  AAGTGCAAGG TCTCCAACAA AGCCCTCCCA GCCCCCATCG AGAAAACCAT

801  CTCCAAAGCC AAAGGGCAGC CCCGAGAACC ACAGGTGTAC ACCCTGCCCC

851  CATCCCGGGA GGAGATGACC AAGAACCAGG TCAGCCTGAC CTGCCTGGTC

901  AAAGGCTTCT ATCCCAGCGA CATCGCCGTG GAGTGGGAGA GCAATGGGCA

951  GCCGGAGAAC AACTACAAGA CCACGCCTCC CGTGCTGGAC TCCGACGGCT

1001 CCTTCTTCCT CTATAGCAAG CTCACCGTGG ACAAGAGCAG GTGGCAGCAG

1051 GGGAACGTCT TCTCATGCTC CGTGATGCAT GAGGCTCTGC ACAACCACTA

1101 CACGCAGAAG AGCCTCTCCC TGTCCCCGGG TAAA
```

Item 13 shows the amino acid sequence of hTβRII$_{short}$ (23-153)-hG2Fc (SEQ ID NO: 37). Dotted underline denotes leader, and solid underline denotes linker.

(SEQ ID NO: 37)

```
  1 MDAMKRGLCC VLLLCGAVFV SPGATIPPHV QKSVNNDMIV TDNNGAVKFP

51 QLCKFCDVRF STCDNQKSCM SNCSITSICE KPQEVCVAVW RKNDENITLE

101 TVCHDPKLPY HDFILEDAAS PKCIMKEKKK PGETFFMCSC SSDECNDNII

151 FSEEYTGGGV ECPPCPAPPV AGPSVFLFPP KPKDTLMISR TPEVTCVVVD

201 VSHEDPEVQF NWYVDGVEVH NAKTKPREEQ FNSTFRVVSV LTVVHQDWLN

251 GKEYKCKVSN KGLPAPIEKT ISKTKGQPRE PQVYTLPPSR EEMTKNQVSL

301 TCLVKGFYPS DIAVEWESNG QPENNYKTTP PMLDSDGSFF LYSKLTVDKS

351 RWQQGNVFSC SVMHEALHNH YTQKSLSLSP GK
```

Item 14 shows a nucleotide sequence encoding hTβRII$_{short}$ (23-153)-hG2Fc (SEQ ID NO: 38). Dotted underline denotes leader, and solid underline denotes linker.

(SEQ ID NO: 38)

```
   1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 TTAATAACGA CATGATAGTC ACTGACAACA ACGGTGCAGT CAAGTTTCCA

151 CAACTGTGTA AATTTTGTGA TGTGAGATTT TCCACCTGTG ACAACCAGAA

201 ATCCTGCATG AGCAACTGCA GCATCACCTC CATCTGTGAG AAGCCACAGG

251 AAGTCTGTGT GGCTGTATGG AGAAAGAATG ACGAGAACAT AACACTAGAG

301 ACAGTTTGCC ATGACCCCAA GCTCCCCTAC CATGACTTTA TTCTGGAAGA

351 TGCTGCTTCT CCAAAGTGCA TTATGAAGGA AAAAAAAAAG CCTGGTGAGA

401 CTTTCTTCAT GTGTTCCTGT AGCTCTGATG AGTGCAATGA CAACATCATC

451 TTCTCAGAAG AATATACCGG TGGTGGAGTC GAGTGCCCAC CGTGCCCAGC

501 ACCACCTGTG GCAGGACCGT CAGTCTTCCT CTTCCCCCCA AAACCCAAGG

551 ACACCCTCAT GATCTCCCGG ACCCCTGAGG TCACGTGCGT GGTGGTGGAC

601 GTGAGCCACG AAGACCCCGA GGTCCAGTTC AACTGGTACG TGGACGGCGT

651 GGAGGTGCAT AATGCCAAGA CAAAGCCACG GGAGGAGCAG TTCAACAGCA

701 CGTTCCGTGT GGTCAGCGTC CTCACCGTCG TGCACCAGGA CTGGCTGAAC

751 GGCAAGGAGT ACAAGTGCAA GGTCTCCAAC AAAGGCCTCC CAGCCCCCAT

801 CGAGAAAACC ATCTCCAAAA CCAAAGGGCA GCCCCGAGAA CCACAGGTGT

851 ACACCCTGCC CCCATCCCGG GAGGAGATGA CCAAGAACCA GGTCAGCCTG

901 ACCTGCCTGG TCAAAGGCTT CTACCCCAGC GACATCGCCG TGGAGTGGGA

951 GAGCAATGGG CAGCCGGAGA ACAACTACAA GACCACACCT CCCATGCTGG

1001 ACTCCGACGG CTCCTTCTTC CTCTACAGCA AGCTCACCGT GGACAAGAGC

1051 AGGTGGCAGC AGGGGAACGT CTTCTCATGC TCCGTGATGC ATGAGGCTCT

1101 GCACAACCAC TACACGCAGA AGAGCCTCTC CCTGTCTCCG GGTAAA
```

Item 15 shows the amino acid sequence of hTβRII$_{short}$ (23-153)-hG1Fc$_{short}$ (SEQ ID NO: 39). Dotted underline denotes leader, and solid underline denotes linker.

(SEQ ID NO: 39)

```
  1  MDAMKRGLCC VLLLCGAVFV SPGATIPPHV QKSVNNDMIV TDNNGAVKFP
 51  QLCKFCDVRF STCDNQKSCM SNCSITSICE KPQEVCVAVW RKNDENITLE
101  TVCHDPKLPY HDFILEDAAS PKCIMKEKKK PGETFFMCSC SSDECNDNII
151  FSEEYTGGGT HTCPPCPAPE LLGGPSVFLF PPKPKDTLMI SRTPEVTCVV
201  VDVSHEDPEV KFNWYVDGVE VHNAKTKPRE EQYNSTYRVV SVLTVLHQDW
251  LNGKEYKCKV SNKALPAPIE KTISKAKGQP REPQVYTLPP SREEMTKNQV
301  SLTCLVKGFY PSDIAVEWES NGQPENNYKT TPPVLDSDGS FFLYSKLTVD
351  KSRWQQGNVF SCSVMHEALH NHYTQKSLSL SPGK
```

Item 16 shows a nucleotide sequence encoding hTβRII$_{short}$ (23-153)-hG1Fc$_{short}$ (SEQ ID NO: 40). Dotted underline denotes leader, and solid underline denotes linker.

(SEQ ID NO: 40)

```
   1  ATGGATGCAA TGAAGAGAGG GCTCTGCTGT GTGCTGCTGC TGTGTGGAGC
  51  AGTCTTCGTT TCGCCCGGCG CCACGATCCC ACCGCACGTT CAGAAGTCGG
 101  TTAATAACGA CATGATAGTC ACTGACAACA ACGGTGCAGT CAAGTTTCCA
 151  CAACTGTGTA AATTTTGTGA TGTGAGATTT TCCACCTGTG ACAACCAGAA
 201  ATCCTGCATG AGCAACTGCA GCATCACCTC CATCTGTGAG AAGCCACAGG
 251  AAGTCTGTGT GGCTGTATGG AGAAAGAATG ACGAGAACAT AACACTAGAG
 301  ACAGTTTGCC ATGACCCCAA GCTCCCCTAC CATGACTTTA TTCTGGAAGA
 351  TGCTGCTTCT CCAAAGTGCA TTATGAAGGA AAAAAAAAAG CCTGGTGAGA
 401  CTTTCTTCAT GTGTTCCTGT AGCTCTGATG AGTGCAATGA CAACATCATC
 451  TTCTCAGAAG AATATACCGG TGGTGGAACT CACACATGCC CACCGTGCCC
 501  AGCACCTGAA CTCCTGGGGG GACCGTCAGT CTTCCTCTTC CCCCCAAAAC
 551  CCAAGGACAC CCTCATGATC TCCCGGACCC CTGAGGTCAC ATGCGTGGTG
 601  GTGGACGTGA GCCACGAAGA CCCTGAGGTC AAGTTCAACT GGTACGTGGA
 651  CGGCGTGGAG GTGCATAATG CCAAGACAAA GCCGCGGGAG GAGCAGTACA
 701  ACAGCACGTA CCGTGTGGTC AGCGTCCTCA CCGTCCTGCA CCAGGACTGG
 751  CTGAATGGCA AGGAGTACAA GTGCAAGGTC TCCAACAAAG CCCTCCCAGC
 801  CCCCATCGAG AAAACCATCT CCAAAGCCAA AGGGCAGCCC CGAGAACCAC
 851  AGGTGTACAC CCTGCCCCCA TCCCGGGAGG AGATGACCAA GAACCAGGTC
 901  AGCCTGACCT GCCTGGTCAA AGGCTTCTAT CCCAGCGACA TCGCCGTGGA
 951  GTGGGAGAGC AATGGGCAGC CGGAGAACAA CTACAAGACC ACGCCTCCCG
1001  TGCTGGACTC CGACGGCTCC TTCTTCCTCT ATAGCAAGCT CACCGTGGAC
1051  AAGAGCAGGT GGCAGCAGGG GAACGTCTTC TCATGCTCCG TGATGCATGA
1101  GGCTCTGCAC AACCACTACA CGCAGAAGAG CCTCTCCCTG TCCCCGGGTA
1151  AA
```

Item 17 shows the amino acid sequence of hTβRII$_{short}$ (23-153/N70D)-hG2Fc (SEQ ID NO: 41). Double underline indicates N70D substitution. Dotted underline denotes leader, and solid underline denotes linker.

(SEQ ID NO: 41)

```
  1  MDAMKRGLCC VLLLCGAVFV SPGATIPPHV QKSVNNDMIV TDNNGAVKFP
 51  QLCKFCDVRF STCDNQKSCM SDCSITSICE KPQEVCVAVW RKNDENITLE
101  TVCHDPKLPY HDFILEDAAS PKCIMKEKKK PGETFFMCSC SSDECNDNII
151  FSEEYTGGGV ECPPCPAPPV AGPSVFLFPP KPKDTLMISR TPEVTCVVVD
201  VSHEDPEVQF NWYVDGVEVH NAKTKPREEQ FNSTFRVVSV LTVVHQDWLN
251  GKEYKCKVSN KGLPAPIEKT ISKTKGQPRE PQVYTLPPSR EEMTKNQVSL
301  TCLVKGFYPS DIAVEWESNG QPENNYKTTP PMLDSDGSFF LYSKLTVDKS
351  RWQQGNVFSC SVMHEALHNH YTQKSLSLSP GK
```

Item 18 shows a nucleotide sequence encoding hTβRII$_{short}$ (23-153/N70D)-hG2Fc (SEQ ID NO: 42). Double underline indicates N70D substitution. Dotted underline denotes leader, and solid underline denotes linker.

(SEQ ID NO: 42)

```
   1  ATGGATGCAA TGAAGAGAGG GCTCTGCTGT GTGCTGCTGC TGTGTGGAGC
  51  AGTCTTCGTT TCGCCCGGCG CCACGATCCC ACCGCACGTT CAGAAGTCGG
 101  TTAATAACGA CATGATAGTC ACTGACAACA ACGGTGCAGT CAAGTTTCCA
 151  CAACTGTGTA AATTTTGTGA TGTGAGATTT TCCACCTGTG ACAACCAGAA
 201  ATCCTGCATG AGCGACTGCA GCATCACCTC CATCTGTGAG AAGCCACAGG
 251  AAGTCTGTGT GGCTGTATGG AGAAAGAATG ACGAGAACAT AACACTAGAG
 301  ACAGTTTGCC ATGACCCCAA GCTCCCCTAC CATGACTTTA TTCTGGAAGA
 351  TGCTGCTTCT CCAAAGTGCA TTATGAAGGA AAAAAAAAAG CCTGGTGAGA
 401  CTTTCTTCAT GTGTTCCTGT AGCTCTGATG AGTGCAATGA CAACATCATC
 451  TTCTCAGAAG AATATACCGG TGGTGGAGTC GAGTGCCCAC CGTGCCCAGC
 501  ACCACCTGTG GCAGGACCGT CAGTCTTCCT CTTCCCCCCA AAACCCAAGG
 551  ACACCCTCAT GATCTCCCGG ACCCCTGAGG TCACGTGCGT GGTGGTGGAC
 601  GTGAGCCACG AAGACCCCGA GGTCCAGTTC AACTGGTACG TGGACGGCGT
 651  GGAGGTGCAT AATGCCAAGA CAAAGCCACG GGAGGAGCAG TTCAACAGCA
 701  CGTTCCGTGT GGTCAGCGTC CTCACCGTCG TGCACCAGGA CTGGCTGAAC
 751  GGCAAGGAGT ACAAGTGCAA GGTCTCCAAC AAAGGCCTCC CAGCCCCCAT
 801  CGAGAAAACC ATCTCCAAAA CCAAAGGGCA GCCCCGAGAA CCACAGGTGT
 851  ACACCCTGCC CCCATCCCGG GAGGAGATGA CCAAGAACCA GGTCAGCCTG
 901  ACCTGCCTGG TCAAAGGCTT CTACCCCAGC GACATCGCCG TGGAGTGGGA
 951  GAGCAATGGG CAGCCGGAGA ACAACTACAA GACCACACCT CCCATGCTGG
1001  ACTCCGACGG CTCCTTCTTC CTCTACAGCA AGCTCACCGT GGACAAGAGC
1051  AGGTGGCAGC AGGGGAACGT CTTCTCATGC TCCGTGATGC ATGAGGCTCT
1101  GCACAACCAC TACACGCAGA AGAGCCTCTC CCTGTCTCCG GGTAAA
```

Item 19 shows the amino acid sequence of hTβRII$_{short}$ (23-153/N70D)-hG1Fc$_{short}$ (SEQ ID NO: 43). Double underline indicates N70D substitution. Dotted underline denotes leader, and solid underline denotes linker.

(SEQ ID NO: 43)

```
  1  MDAMKRGLCC VLLLCGAVFV SPGATIPPHV QKSVNNDMIV TDNNGAVKFP
 51  QLCKFCDVRF STCDNQKSCM SDCSITSICE KPQEVCVAVW RKNDENITLE
101  TVCHDPKLPY HDFILEDAAS PKCIMKEKKK PGETFFMCSC SSDECNDNII
151  FSEEYTGGGT HTCPPCPAPE LLGGPSVFLF PPKPKDTLMI SRTPEVTCVV
201  VDVSHEDPEV KFNWYVDGVE VHNAKTKPRE EQYNSTYRVV SVLTVLHQDW
251  LNGKEYKCKV SNKALPAPIE KTISKAKGQP REPQVYTLPP SREEMTKNQV
301  SLTCLVKGFY PSDIAVEWES NGQPENNYKT TPPVLDSDGS FFLYSKLTVD
351  KSRWQQGNVF SCSVMHEALH NHYTQKSLSL SPGK
```

Item 20 shows a nucleotide sequence encoding hTβRII$_{short}$ (23-153/N70D)-hG1Fc$_{short}$ (SEQ ID NO: 44). Double underline indicates N70D substitution. Dotted underline denotes leader, and solid underline denotes linker.

(SEQ ID NO: 44)

```
   1  ATGGATGCAA TGAAGAGAGG GCTCTGCTGT GTGCTGCTGC TGTGTGGAGC
  51  AGTCTTCGTT TCGCCCGGCG CCACGATCCC ACCGCACGTT CAGAAGTCGG
 101  TTAATAACGA CATGATAGTC ACTGACAACA ACGGTGCAGT CAAGTTTCCA
 151  CAACTGTGTA AATTTTGTGA TGTGAGATTT TCCACCTGTG ACAACCAGAA
 201  ATCCTGCATG AGCGACTGCA GCATCACCTC CATCTGTGAG AAGCCACAGG
 251  AAGTCTGTGT GGCTGTATGG AGAAAGAATG ACGAGAACAT AACACTAGAG
 301  ACAGTTTGCC ATGACCCCAA GCTCCCCTAC CATGACTTTA TTCTGGAAGA
 351  TGCTGCTTCT CCAAAGTGCA TTATGAAGGA AAAAAAAAAG CCTGGTGAGA
 401  CTTTCTTCAT GTGTTCCTGT AGCTCTGATG AGTGCAATGA CAACATCATC
 451  TTCTCAGAAG AATATACCGG TGGTGGAACT CACACATGCC CACCGTGCCC
 501  AGCACCTGAA CTCCTGGGGG GACCGTCAGT CTTCCTCTTC CCCCCAAAAC
 551  CCAAGGACAC CCTCATGATC TCCCGGACCC TGAGGTCAC ATGCGTGGTG
 601  GTGGACGTGA GCCACGAAGA CCCTGAGGTC AAGTTCAACT GGTACGTGGA
 651  CGGCGTGGAG GTGCATAATG CCAAGACAAA GCCGCGGGAG GAGCAGTACA
 701  ACAGCACGTA CCGTGTGGTC AGCGTCCTCA CCGTCCTGCA CCAGGACTGG
 751  CTGAATGGCA AGGAGTACAA GTGCAAGGTC TCCAACAAAG CCCTCCCAGC
 801  CCCCATCGAG AAAACCATCT CCAAAGCCAA AGGGCAGCCC CGAGAACCAC
 851  AGGTGTACAC CCTGCCCCCA TCCCGGGAGG AGATGACCAA GAACCAGGTC
 901  AGCCTGACCT GCCTGGTCAA AGGCTTCTAT CCCAGCGACA TCGCCGTGGA
 951  GTGGGAGAGC AATGGGCAGC CGGAGAACAA CTACAAGACC ACGCCTCCCG
1001  TGCTGGACTC CGACGGCTCC TTCTTCCTCT ATAGCAAGCT CACCGTGGAC
1051  AAGAGCAGGT GGCAGCAGGG GAACGTCTTC TCATGCTCCG TGATGCATGA
1101  GGCTCTGCAC AACCACTACA CGCAGAAGAG CCTCTCCCTG TCCCCGGGTA
1151  AA
```

Item 21 shows the mature amino acid sequence (i.e., without the leader sequence) of hTβRII_short (23-159/D110K)-hG2Fc (SEQ ID NO: 53). Double underline indicates D110K substitution. Single underline denotes linker.

(SEQ ID NO: 53)
```
TIPPHV QKSVNNDMIV TDNNGAVKFP
QLCKFCDVRF STCDNQKSCM SNCSITSICE KPQEVCVAVW
RKNDENITLE TVCHDPKLPY HKFILEDAAS PKCIMKEKKK
PGETFFMCSC SSDECNDNII FSEEYNTSNP DTGGGVECPP
CPAPPVAGPS VFLFPPKPKD TLMISRTPEV TCVVVDVSHE
DPEVQFNWYV DGVEVHNAKT KPREEQFNST FRVVSVLTVV
HQDWLNGKEY KCKVSNKGLP APIEKTISKT KGQPREPQVY
TLPPSREEMT KNQVSLTCLV KGFYPSDIAV EWESNGQPEN
NYKTTPPMLD SDGSFFLYSK LTVDKSRWQQ GNVFSCSVMH
EALHNHYTQK SLSLSPGK
```

Item 22 shows the mature amino acid sequence (i.e., without the leader sequence) of hTβRII_short (23-159/D110K)-hG1Fc_short (SEQ ID NO: 54). Double underline indicates D110K substitution. Single underline denotes linker.

(SEQ ID NO: 54)
```
TIPPHV QKSVNNDMIV TDNNGAVKFP
QLCKFCDVRF STCDNQKSCM SNCSITSICE KPQEVCVAVW
RKNDENITLE TVCHDPKLPY HKFILEDAAS PKCIMKEKKK
PGETFFMCSC SSDECNDNII FSEEYNTSNP DTGGGTHTCP
PCPAPELLGG PSVFLFPPKP KDTLMISRTP EVTCVVVDVS
HEDPEVKFNW YVDGVEVHNA KTKPREEQYN STYRVVSVLT
VLHQDWLNGK EYKCKVSNKA LPAPIEKTIS KAKGQPREPQ
VYTLPPSREE MTKNQVSLTC LVKGFYPSDI AVEWESNGQP
ENNYKTTPPV LDSDGSFFLY SKLTVDKSRW QQGNVFSCSV
MHEALHNHYT QKSLSLSPGK
```

Item 23 shows the mature amino acid sequence (i.e., without the leader sequence) of hTβRII_short (29-159)-hG2Fc (SEQ ID NO: 55). Single underline denotes linker.

(SEQ ID NO: 55)
```
QKSVNN DMIVTDNNGA VKFPQLCKFC
DVRFSTCDNQ KSCMSNCSIT SICEKPQEVC VAVWRKNDEN
ITLETVCHDP KLPYHDFILE DAASPKCIMK EKKKPGETFF
MCSCSSDECN DNIIFSEEYN TSNPDTGGGV ECPPCPAPPV
AGPSVFLFPP KPKDTLMISR TPEVTCVVVD VSHEDPEVQF
NWYVDGVEVH NAKTKPREEQ FNSTFRVVSV LTVVHQDWLN
GKEYKCKVSN KGLPAPIEKT ISKTKGQPRE PQVYTLPPSR
EEMTKNQVSL TCLVKGFYPS DIAVEWESNG QPENNYKTTP
PMLDSDGSFF LYSKLTVDKS RWQQGNVFSC SVMHEALHNH
YTQKSLSLSP GK
```

Item 24 shows the mature amino acid sequence (i.e., without the leader sequence) of hTβRII_short (29-159)-hG1Fc_short (SEQ ID NO: 56). Single underline denotes linker.

(SEQ ID NO: 56)
```
QKSVNN DMIVTDNNGA VKFPQLCKFC
DVRFSTCDNQ KSCMSNCSIT SICEKPQEVC VAVWRKNDEN
ITLETVCHDP KLPYHDFILE DAASPKCIMK EKKKPGETFF
MCSCSSDECN DNIIFSEEYN TSNPDTGGGT HTCPPCPAPE
LLGGPSVFLF PPKPKDTLMI SRTPEVTCVV VDVSHEDPEV
KFNWYVDGVE VHNAKTKPRE EQYNSTYRVV SVLTVLHQDW
LNGKEYKCKV SNKALPAPIE KTISKAKGQP REPQVYTLPP
SREEMTKNQV SLTCLVKGFY PSDIAVEWES NGQPENNYKT
TPPVLDSDGS FFLYSKLTVD KSRWQQGNVF SCSVMHEALH
NHYTQKSLSL SPGK
```

Item 25 shows the mature amino acid sequence (i.e., without the leader sequence) of hTβRII_short (35-159)-hG2Fc (SEQ ID NO: 57). Single underline denotes linker.

(SEQ ID NO: 57)
```
DMIVTD NNGAVKFPQL CKFCDVRFST
CDNQKSCMSN CSITSICEKP QEVCVAVWRK NDENITLETV
CHDPKLPYHD FILEDAASPK CIMKEKKKPG ETFFMCSCSS
DECNDNIIFS EEYNTSNPDT GGGVECPPCP APPVAGPSVF
LFPPKPKDTL MISRTPEVTC VVVDVSHEDP EVQFNWYVDG
VEVHNAKTKP REEQFNSTFR VVSVLTVVHQ DWLNGKEYKC
KVSNKGLPAP IEKTISKTKG QPREPQVYTL PPSREEMTKN
QVSLTCLVKG FYPSDIAVEW ESNGQPENNY KTTPPMLDSD
GSFFLYSKLT VDKSRWQQGN VFSCSVMHEA LHNHYTQKSL SLSPGK
```

Item 26 shows the mature amino acid sequence (i.e., without the leader sequence) of hTβRII_short (35-159)-hG1Fc_short (SEQ ID NO: 58). Single underline denotes linker.

(SEQ ID NO: 58)
```
DMIVTD NNGAVKFPQL CKFCDVRFST
CDNQKSCMSN CSITSICEKP QEVCVAVWRK NDENITLETV
CHDPKLPYHD FILEDAASPK CIMKEKKKPG ETFFMCSCSS
DECNDNIIFS EEYNTSNPDT GGGTHTCPPC PAPELLGGPS
VFLFPPKPKD TLMISRTPEV TCVVVDVSHE DPEVKFNWYV
DGVEVHNAKT KPREEQYNST YRVVSVLTVL HQDWLNGKEY
KCKVSNKALP APIEKTISKA KGQPREPQVY TLPPSREEMT
KNQVSLTCLV KGFYPSDIAV EWESNGQPEN NYKTTPPVLD
SDGSFFLYSK LTVDKSRWQQ GNVFSCSVMH EALHNHYTQK
SLSLSPGK
```

Item 27 shows the mature amino acid sequence (i.e., without the leader sequence) of hTβRII_short (23-153)-hG2Fc (SEQ ID NO: 59). Single underline denotes linker.

(SEQ ID NO: 59)
TIPPHV QKSVNNDMIV TDNNGAVKFP

QLCKFCDVRF STCDNQKSCM SNCSITSICE KPQEVCVAVW

RKNDENITLE TVCHDPKLPY HDFILEDAAS PKCIMKEKKK

PGETFFMCSC SSDECNDNII FSEEY<u>TGGGV</u> ECPPCPAPPV

AGPSVFLFPP KPKDTLMISR TPEVTCVVVD VSHEDPEVQF

NWYVDGVEVH NAKTKPREEQ FNSTFRVVSV LTVVHQDWLN

GKEYKCKVSN KGLPAPIEKT ISKTKGQPRE PQVYTLPPSR

EEMTKNQVSL TCLVKGFYPS DIAVEWESNG QPENNYKTTP

PMLDSDGSFF LYSKLTVDKS RWQQGNVFSC SVMHEALHNH

YTQKSLSLSP GK

Item 28 shows the mature amino acid sequence (i.e., without the leader sequence) of hTβRII$_{short}$ (23-153)-hG1Fc$_{short}$ (SEQ ID NO: 60). Single underline denotes linker.

(SEQ ID NO: 60)
TIPPHV QKSVNNDMIV TDNNGAVKFP

QLCKFCDVRF STCDNQKSCM SNCSITSICE KPQEVCVAVW

RKNDENITLE TVCHDPKLPY HDFILEDAAS PKCIMKEKKK

PGETFFMCSC SSDECNDNII FSEEY<u>TGGGT</u> HTCPPCPAPE

LLGGPSVFLF PPKPKDTLMI SRTPEVTCVV VDVSHEDPEV

KFNWYVDGVE VHNAKTKPRE EQYNSTYRVV SVLTVLHQDW

LNGKEYKCKV SNKALPAPIE KTISKAKGQP REPQVYTLPP

SREEMTKNQV SLTCLVKGFY PSDIAVEWES NGQPENNYKT

TPPVLDSDGS FFLYSKLTVD KSRWQQGNVF SCSVMHEALH

NHYTQKSLSL SPGK

Item 29 shows the mature amino acid sequence (i.e., without the leader sequence) of hTβRII$_{short}$ (23-153/N70D)-hG2Fc (SEQ ID NO: 61). Double underline indicates N70D substitution. Single underline denotes linker.

(SEQ ID NO: 61)
TIPPHV QKSVNNDMIV TDNNGAVKFP

QLCKFCDVRF STCDNQKSCM S<u><u>D</u></u>CSITSICE KPQEVCVAVW

RKNDENITLE TVCHDPKLPY HDFILEDAAS PKCIMKEKKK

PGETFFMCSC SSDECNDNII FSEEY<u>TGGGV</u> ECPPCPAPPV

AGPSVFLFPP KPKDTLMISR TPEVTCVVVD VSHEDPEVQF

NWYVDGVEVH NAKTKPREEQ FNSTFRVVSV LTVVHQDWLN

GKEYKCKVSN KGLPAPIEKT ISKTKGQPRE PQVYTLPPSR

EEMTKNQVSL TCLVKGFYPS DIAVEWESNG QPENNYKTTP

PMLDSDGSFF LYSKLTVDKS RWQQGNVFSC SVMHEALHNH

YTQKSLSLSP GK

Item 30 shows the mature amino acid sequence (i.e., without the leader sequence) of hTβRII$_{short}$ (23-153/N70D)-hG1Fc$_{short}$ (SEQ ID NO: 62). Double underline indicates N70D substitution. Single underline denotes linker.

(SEQ ID NO: 62)
TIPPHV QKSVNNDMIV TDNNGAVKFP

QLCKFCDVRF STCDNQKSCM S<u><u>D</u></u>CSITSICE KPQEVCVAVW

RKNDENITLE TVCHDPKLPY HDFILEDAAS PKCIMKEKKK

PGETFFMCSC SSDECNDNII FSEEY<u>TGGGT</u> HTCPPCPAPE

LLGGPSVFLF PPKPKDTLMI SRTPEVTCVV VDVSHEDPEV

KFNWYVDGVE VHNAKTKPRE EQYNSTYRVV SVLTVLHQDW

LNGKEYKCKV SNKALPAPIE KTISKAKGQP REPQVYTLPP

SREEMTKNQV SLTCLVKGFY PSDIAVEWES NGQPENNYKT

TPPVLDSDGS FFLYSKLTVD KSRWQQGNVF SCSVMHEALH

NHYTQKSLSL SPGK

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A Transforming Growth Factor β Receptor II (TβRII) fusion polypeptide comprising a first amino acid sequence from the extracellular domain of TβRII and a heterologous amino acid sequence, wherein the first amino acid sequence consists of an amino acid sequence at least 95% identical to the amino acid sequence of SEQ ID NO: 13, wherein the fusion polypeptide does not include the amino acids corresponding to amino acids 1-22 and 185-592 of SEQ ID NO: 6;

and wherein the fusion polypeptide binds Transforming Growth Factor β1 or Transforming Growth Factor β3.

2. The TβRII fusion polypeptide of claim 1, wherein the heterologous amino acid sequence is joined to the TβRII polypeptide by a linker, and wherein the heterologous amino acid sequence comprises a polypeptide portion selected from: an immunoglobulin Fc domain and a serum albumin.

3. The TβRII fusion polypeptide of claim 1, wherein the first amino acid sequence consists of the amino acid sequence of SEQ ID NO: 13.

4. The TβRII fusion polypeptide of claim 1, wherein the heterologous amino acid sequence comprises the amino acid sequence of SEQ ID NO: 21.

5. The TβRII fusion polypeptide of claim 3, wherein the heterologous amino acid sequence comprises the amino acid sequence of SEQ ID NO: 21.

6. The TβRII fusion polypeptide of claim 5, wherein the heterologous amino acid sequence is joined to the TβRII polypeptide by a linker.

7. The TβRII fusion polypeptide of claim 1, wherein the fusion polypeptide binds Transforming Growth Factor β1 and Transforming Growth Factor β3.

8. The TβRII fusion polypeptide of claim 6, wherein the fusion polypeptide binds Transforming Growth Factor β1 and Transforming Growth Factor β3.

9. A pharmaceutical preparation comprising the polypeptide of claim 1 and a pharmaceutically acceptable excipient.

* * * * *

SEQUENCE LISTING

```
<160> NUMBER OF SEQ ID NOS: 69

<210> SEQ ID NO 1
<211> LENGTH: 308
<212> TYPE: PRT
<213> ORGANISM: Homo sapiens

<400> SEQUENCE: 1

Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
            20                  25                  30
```

Ala Glu Ala Ser Arg Ala Ser Phe Pro Gly Pro Ser Glu Leu His Ser
 35                  40                  45

Glu Asp Ser Arg Phe Arg Glu Leu Arg Lys Arg Tyr Glu Asp Leu Leu
 50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                 85                  90                  95

Ser Gly Gly His Leu His Leu Arg Ile Ser Arg Ala Ala Leu Pro Glu
                100                 105                 110

Gly Leu Pro Glu Ala Ser Arg Leu His Arg Ala Leu Phe Arg Leu Ser
            115                 120                 125

Pro Thr Ala Ser Arg Ser Trp Asp Val Thr Arg Pro Leu Arg Arg Gln
        130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
                180                 185                 190

Arg Arg Ala Arg Ala Arg Asn Gly Asp His Cys Pro Leu Gly Pro Gly
            195                 200                 205

Arg Cys Cys Arg Leu His Thr Val Arg Ala Ser Leu Glu Asp Leu Gly
        210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
                260                 265                 270

Cys Cys Val Pro Ala Ser Tyr Asn Pro Met Val Leu Ile Gln Lys Thr
            275                 280                 285

Asp Thr Gly Val Ser Leu Gln Thr Tyr Asp Asp Leu Leu Ala Lys Asp
        290                 295                 300

Cys His Cys Ile
305

<210> SEQ ID NO 2
<211> LENGTH: 924
<212> TYPE: DNA
<213> ORGANISM: Homo sapiens

<400> SEQUENCE: 2
atgcccgggc aagaactcag gacggtgaat ggctctcaga tgctcctggt gttgctggtg      60
ctctcgtggc tgccgcatgg gggcgccctg tctctggccg aggcgagccg cgcaagtttc     120
ccgggaccct cagagttgca ctccgaagac tccagattcc gagagttgcg aaaacgctac     180
gaggacctgc taaccaggct gcgggccaac cagagctggg aagattcgaa caccgacctc     240
gtcccggccc ctgcagtccg gatactcacg ccagaagtgc ggctgggatc cggcggccac     300
ctgcacctgc gtatctctcg gccgcccctt cccgaggggc tccccgaggc ctcccgcctt     360
caccgggctc tgttccggct gtccccgacg gcgtcaaggt cgtgggacgt gacacgaccg     420
ctgcggcgtc agctcagcct tgcaagaccc caggcacccg cgctgcacct gcgactgtcg     480
ccgccgccgt cgcagtcgga ccaactgctg gcagaatctt cgtccgcacg gccccagctg     540

```
gagttgcact tgcggccgca agccgccagg gggcgccgca gagcgcgtgc gcgcaacggg    600
gaccactgtc cgctcgggcc cgggcgttgc tgccgtctgc acacggtccg cgcgtcgctg    660
gaagacctgg gctgggccga ttgggtgctg tcgccacggg aggtgcaagt gaccatgtgc    720
atcggcgcgt gcccgagcca gttccgggcg gcaaacatgc acgcgcagat caagacgagc    780
ctgcaccgcc tgaagcccga cacggtgcca gcgccctgct gcgtgccgcc cagctacaat    840
cccatggtgc tcattcaaaa gaccgacacc ggggtgtcac tccagaccta tgatgacttg    900
ttagccaaag actgccactg cata                                           924
```

```
<210> SEQ ID NO 3
<211> LENGTH: 303
<212> TYPE: PRT
<213> ORGANISM: Mus musculus

<400> SEQUENCE: 3

Met Ala Pro Pro Ala Leu Gln Ala Gln Pro Gly Gly Ser Gln Leu
1               5                   10                  15

Arg Phe Leu Leu Phe Leu Leu Leu Leu Leu Leu Leu Ser Trp Pro
                20                  25                  30

Ser Gln Gly Asp Ala Leu Ala Met Pro Glu Gln Arg Pro Ser Gly Pro
            35                  40                  45

Glu Ser Gln Leu Asn Ala Asp Glu Leu Arg Gly Arg Phe Gln Asp Leu
        50                  55                  60

Leu Ser Arg Leu His Ala Asn Gln Ser Arg Glu Asp Ser Asn Ser Glu
65                  70                  75                  80

Pro Ser Pro Asp Pro Ala Val Arg Ile Leu Ser Pro Glu Val Arg Leu
                85                  90                  95

Gly Ser His Gly Gln Leu Leu Leu Arg Val Asn Arg Ala Ser Leu Ser
            100                 105                 110

Gln Gly Leu Pro Glu Ala Tyr Arg Val His Arg Ala Leu Leu Leu Leu
        115                 120                 125

Thr Pro Thr Ala Arg Pro Trp Asp Ile Thr Arg Pro Leu Lys Arg Ala
130                 135                 140

Leu Ser Leu Arg Gly Pro Arg Ala Pro Ala Leu Arg Leu Arg Leu Thr
145                 150                 155                 160

Pro Pro Pro Asp Leu Ala Met Leu Pro Ser Gly Gly Thr Gln Leu Glu
                165                 170                 175

Leu Arg Leu Arg Val Ala Ala Gly Arg Gly Arg Arg Ser Ala His Ala
            180                 185                 190

His Pro Arg Asp Ser Cys Pro Leu Gly Pro Gly Arg Cys Cys His Leu
        195                 200                 205

Glu Thr Val Gln Ala Thr Leu Glu Asp Leu Gly Trp Ser Asp Trp Val
    210                 215                 220

Leu Ser Pro Arg Gln Leu Gln Leu Ser Met Cys Val Gly Glu Cys Pro
225                 230                 235                 240

His Leu Tyr Arg Ser Ala Asn Thr His Ala Gln Ile Lys Ala Arg Leu
                245                 250                 255

His Gly Leu Gln Pro Asp Lys Val Pro Ala Pro Cys Cys Val Pro Ser
            260                 265                 270

Ser Tyr Thr Pro Val Val Leu Met His Arg Thr Asp Ser Gly Val Ser
        275                 280                 285

Leu Gln Thr Tyr Asp Asp Leu Val Ala Arg Gly Cys His Cys Ala
    290                 295                 300
```

<210> SEQ ID NO 4
<211> LENGTH: 909
<212> TYPE: DNA
<213> ORGANISM: Mus musculus

<400> SEQUENCE: 4

| | |
|---|---|
| atggccccgc ccgcgctcca ggcccagcct ccaggcggct ctcaactgag gttcctgctg | 60 |
| ttcctgctgc tgttgctgct gctgctgtca tggccatcgc aggggacgc cctggcaatg | 120 |
| cctgaacagc gaccctccgg ccctgagtcc caactcaacg ccgacgagct acgggtcgc | 180 |
| ttccaggacc tgctgagccg gctgcatgcc aaccagagcc gagaggactc gaactcagaa | 240 |
| ccaagtcctg acccagctgt ccggatactc agtccagagg tgagattggg gtcccacggc | 300 |
| cagctgctac tccgcgtcaa ccgggcgtcg ctgagtcagg gtctccccga agcctaccgc | 360 |
| gtgcaccgag cgctgctcct gctgacgccg acggcccgcc cctgggacat cactaggccc | 420 |
| ctgaagcgtg cgctcagcct ccggggaccc cgtgctcccg cattacgcct gcgcctgacg | 480 |
| ccgcctccgg acctggctat gctgccctct ggcggcacgc agctggaact gcgcttacgg | 540 |
| gtagccgccg gcaggggggcg ccgaagcgcg catgcgcacc caagagactc gtgcccactg | 600 |
| ggtccagggc gctgctgtca cttggagact gtgcaggcaa ctcttgaaga cttgggctgg | 660 |
| agcgactggg tgctgtcccc cgccagctg cagctgagca tgtgcgtggg cgagtgtccc | 720 |
| cacctgtatc gctccgcgaa cacgcatgcg cagatcaaag cacgcctgca tggcctgcag | 780 |
| cctgacaagg tgcctgcccc gtgctgtgtc ccctccagct acaccccggt ggttcttatg | 840 |
| cacaggacag acagtggtgt gtcactgcag acttatgatg acctggtggc ccggggctgc | 900 |
| cactgcgct | 909 |

<210> SEQ ID NO 5
<211> LENGTH: 567
<212> TYPE: PRT
<213> ORGANISM: Homo sapiens

<400> SEQUENCE: 5

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu

```
                  165                 170                 175
Gly Val Ala Ile Ser Val Ile Ile Phe Tyr Cys Tyr Arg Val Asn
            180                 185                 190
Arg Gln Gln Lys Leu Ser Ser Thr Trp Glu Thr Gly Lys Thr Arg Lys
            195                 200                 205
Leu Met Glu Phe Ser Glu His Cys Ala Ile Ile Leu Glu Asp Asp Arg
        210                 215                 220
Ser Asp Ile Ser Ser Thr Cys Ala Asn Asn Ile Asn His Asn Thr Glu
225                 230                 235                 240
Leu Leu Pro Ile Glu Leu Asp Thr Leu Val Gly Lys Gly Arg Phe Ala
                245                 250                 255
Glu Val Tyr Lys Ala Lys Leu Lys Gln Asn Thr Ser Glu Gln Phe Glu
            260                 265                 270
Thr Val Ala Val Lys Ile Phe Pro Tyr Glu Glu Tyr Ala Ser Trp Lys
        275                 280                 285
Thr Glu Lys Asp Ile Phe Ser Asp Ile Asn Leu Lys His Glu Asn Ile
    290                 295                 300
Leu Gln Phe Leu Thr Ala Glu Glu Arg Lys Thr Glu Leu Gly Lys Gln
305                 310                 315                 320
Tyr Trp Leu Ile Thr Ala Phe His Ala Lys Gly Asn Leu Gln Glu Tyr
                325                 330                 335
Leu Thr Arg His Val Ile Ser Trp Glu Asp Leu Arg Lys Leu Gly Ser
            340                 345                 350
Ser Leu Ala Arg Gly Ile Ala His Leu His Ser Asp His Thr Pro Cys
        355                 360                 365
Gly Arg Pro Lys Met Pro Ile Val His Arg Asp Leu Lys Ser Ser Asn
    370                 375                 380
Ile Leu Val Lys Asn Asp Leu Thr Cys Cys Leu Cys Asp Phe Gly Leu
385                 390                 395                 400
Ser Leu Arg Leu Asp Pro Thr Leu Ser Val Asp Asp Leu Ala Asn Ser
                405                 410                 415
Gly Gln Val Gly Thr Ala Arg Tyr Met Ala Pro Glu Val Leu Glu Ser
            420                 425                 430
Arg Met Asn Leu Glu Asn Val Glu Ser Phe Lys Gln Thr Asp Val Tyr
        435                 440                 445
Ser Met Ala Leu Val Leu Trp Glu Met Thr Ser Arg Cys Asn Ala Val
    450                 455                 460
Gly Glu Val Lys Asp Tyr Glu Pro Pro Phe Gly Ser Lys Val Arg Glu
465                 470                 475                 480
His Pro Cys Val Glu Ser Met Lys Asp Asn Val Leu Arg Asp Arg Gly
                485                 490                 495
Arg Pro Glu Ile Pro Ser Phe Trp Leu Asn His Gln Gly Ile Gln Met
            500                 505                 510
Val Cys Glu Thr Leu Thr Glu Cys Trp Asp His Asp Pro Glu Ala Arg
        515                 520                 525
Leu Thr Ala Gln Cys Val Ala Glu Arg Phe Ser Glu Leu Glu His Leu
    530                 535                 540
Asp Arg Leu Ser Gly Arg Ser Cys Ser Glu Glu Lys Ile Pro Glu Asp
545                 550                 555                 560
Gly Ser Leu Asn Thr Thr Lys
                565

<210> SEQ ID NO 6
```

```
<211> LENGTH: 592
<212> TYPE: PRT
<213> ORGANISM: Homo sapiens

<400> SEQUENCE: 6

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
            20                  25                  30

Val Glu Met Glu Ala Gln Lys Asp Glu Ile Ile Cys Pro Ser Cys Asn
        35                  40                  45

Arg Thr Ala His Pro Leu Arg His Ile Asn Asn Asp Met Ile Val Thr
    50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
        115                 120                 125

Pro Lys Leu Pro Tyr His Asp Phe Ile Leu Glu Asp Ala Ala Ser Pro
    130                 135                 140

Lys Cys Ile Met Lys Glu Lys Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
            180                 185                 190

Thr Gly Ile Ser Leu Leu Pro Pro Leu Gly Val Ala Ile Ser Val Ile
        195                 200                 205

Ile Ile Phe Tyr Cys Tyr Arg Val Asn Arg Gln Gln Lys Leu Ser Ser
    210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
            260                 265                 270

Thr Leu Val Gly Lys Gly Arg Phe Ala Glu Val Tyr Lys Ala Lys Leu
        275                 280                 285

Lys Gln Asn Thr Ser Glu Gln Phe Glu Thr Val Ala Val Lys Ile Phe
    290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
            340                 345                 350

His Ala Lys Gly Asn Leu Gln Glu Tyr Leu Thr Arg His Val Ile Ser
        355                 360                 365

Trp Glu Asp Leu Arg Lys Leu Gly Ser Ser Leu Ala Arg Gly Ile Ala
    370                 375                 380

His Leu His Ser Asp His Thr Pro Cys Gly Arg Pro Lys Met Pro Ile
```

```
                385                 390                 395                 400
Val His Arg Asp Leu Lys Ser Ser Asn Ile Leu Val Lys Asn Asp Leu
                    405                 410                 415

Thr Cys Cys Leu Cys Asp Phe Gly Leu Ser Leu Arg Leu Asp Pro Thr
                420                 425                 430

Leu Ser Val Asp Asp Leu Ala Asn Ser Gly Gln Val Gly Thr Ala Arg
                435                 440                 445

Tyr Met Ala Pro Glu Val Leu Glu Ser Arg Met Asn Leu Glu Asn Val
            450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
                485                 490                 495

Pro Pro Phe Gly Ser Lys Val Arg Glu His Pro Cys Val Glu Ser Met
                500                 505                 510

Lys Asp Asn Val Leu Arg Asp Arg Gly Arg Pro Glu Ile Pro Ser Phe
            515                 520                 525

Trp Leu Asn His Gln Gly Ile Gln Met Val Cys Glu Thr Leu Thr Glu
530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
                565                 570                 575

Cys Ser Glu Glu Lys Ile Pro Glu Asp Gly Ser Leu Asn Thr Thr Lys
            580                 585                 590
```

<210> SEQ ID NO 7
<211> LENGTH: 137
<212> TYPE: PRT
<213> ORGANISM: Homo sapiens

<400> SEQUENCE: 7

```
Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
                20                  25                  30

Asp Val Arg Phe Ser Thr Cys Asp Asn Gln Lys Ser Cys Met Ser Asn
            35                  40                  45

Cys Ser Ile Thr Ser Ile Cys Glu Lys Pro Gln Glu Val Cys Val Ala
        50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
                100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp
        130                 135
```

<210> SEQ ID NO 8
<211> LENGTH: 137
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 8

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Lys Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp
    130                 135

<210> SEQ ID NO 9
<211> LENGTH: 131
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 9

Gln Lys Ser Val Asn Asn Asp Met Ile Val Thr Asp Asn Asn Gly Ala
1               5                   10                  15

Val Lys Phe Pro Gln Leu Cys Lys Phe Cys Asp Val Arg Phe Ser Thr
            20                  25                  30

Cys Asp Asn Gln Lys Ser Cys Met Ser Asn Cys Ser Ile Thr Ser Ile
        35                  40                  45

Cys Glu Lys Pro Gln Glu Val Cys Val Ala Val Trp Arg Lys Asn Asp
    50                  55                  60

Glu Asn Ile Thr Leu Glu Thr Val Cys His Asp Pro Lys Leu Pro Tyr
65                  70                  75                  80

His Asp Phe Ile Leu Glu Asp Ala Ala Ser Pro Lys Cys Ile Met Lys
                85                  90                  95

Glu Lys Lys Pro Gly Glu Thr Phe Phe Met Cys Ser Cys Ser Ser
            100                 105                 110

Asp Glu Cys Asn Asp Asn Ile Ile Phe Ser Glu Glu Tyr Asn Thr Ser
        115                 120                 125

Asn Pro Asp
    130

<210> SEQ ID NO 10
<211> LENGTH: 125
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 10

Asp Met Ile Val Thr Asp Asn Asn Gly Ala Val Lys Phe Pro Gln Leu
1               5                   10                  15

Cys Lys Phe Cys Asp Val Arg Phe Ser Thr Cys Asp Asn Gln Lys Ser
            20                  25                  30

Cys Met Ser Asn Cys Ser Ile Thr Ser Ile Cys Glu Lys Pro Gln Glu
        35                  40                  45

Val Cys Val Ala Val Trp Arg Lys Asn Asp Glu Asn Ile Thr Leu Glu
    50                  55                  60

Thr Val Cys His Asp Pro Lys Leu Pro Tyr His Asp Phe Ile Leu Glu
65                  70                  75                  80

Asp Ala Ala Ser Pro Lys Cys Ile Met Lys Glu Lys Lys Pro Gly
                85                  90                  95

Glu Thr Phe Phe Met Cys Ser Cys Ser Ser Asp Glu Cys Asn Asp Asn
            100                 105                 110

Ile Ile Phe Ser Glu Glu Tyr Asn Thr Ser Asn Pro Asp
        115                 120                 125

<210> SEQ ID NO 11
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr
        130

<210> SEQ ID NO 12
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys

```
                    20                  25                  30
Asp Val Arg Phe Ser Thr Cys Asp Asn Gln Lys Ser Cys Met Ser Asp
            35                  40                  45

Cys Ser Ile Thr Ser Ile Cys Glu Lys Pro Gln Val Cys Val Ala
        50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr
        130

<210> SEQ ID NO 13
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160

Pro Asp

<210> SEQ ID NO 14
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Thr Ile Pro Pro His Val Gln Lys Ser Asp Val Glu Met Glu Ala Gln
1               5                   10                  15
```

```
Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Lys Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160

Pro Asp

<210> SEQ ID NO 15
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Lys Ser Asp Val Glu Met Glu Ala Gln Lys Asp Glu Ile Ile Cys
1               5                   10                  15

Pro Ser Cys Asn Arg Thr Ala His Pro Leu Arg His Ile Asn Asn Asp
            20                  25                  30

Met Ile Val Thr Asp Asn Asn Gly Ala Val Lys Phe Pro Gln Leu Cys
        35                  40                  45

Lys Phe Cys Asp Val Arg Phe Ser Thr Cys Asp Asn Gln Lys Ser Cys
    50                  55                  60

Met Ser Asn Cys Ser Ile Thr Ser Ile Cys Glu Lys Pro Gln Glu Val
65                  70                  75                  80

Cys Val Ala Val Trp Arg Lys Asn Asp Glu Asn Ile Thr Leu Glu Thr
                85                  90                  95

Val Cys His Asp Pro Lys Leu Pro Tyr His Asp Phe Ile Leu Glu Asp
            100                 105                 110

Ala Ala Ser Pro Lys Cys Ile Met Lys Glu Lys Lys Lys Pro Gly Glu
        115                 120                 125

Thr Phe Phe Met Cys Ser Cys Ser Ser Asp Glu Cys Asn Asp Asn Ile
    130                 135                 140

Ile Phe Ser Glu Glu Tyr Asn Thr Ser Asn Pro Asp
145                 150                 155

<210> SEQ ID NO 16
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 16

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr
145                 150                 155

<210> SEQ ID NO 17
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asp Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr
145                 150                 155

<210> SEQ ID NO 18
<211> LENGTH: 36
<212> TYPE: PRT
<213> ORGANISM: Homo sapiens -continued

```
<400> SEQUENCE: 18

Gly Arg Cys Lys Ile Arg His Ile Gly Ser Asn Asn Arg Leu Gln Arg
1               5                  10                  15

Ser Thr Cys Gln Asn Thr Gly Trp Glu Ser Ala His Val Met Lys Thr
            20                  25                  30

Pro Gly Phe Arg
        35

<210> SEQ ID NO 19
<211> LENGTH: 223
<212> TYPE: PRT
<213> ORGANISM: Homo sapiens

<400> SEQUENCE: 19

Val Glu Cys Pro Pro Cys Pro Ala Pro Pro Val Ala Gly Pro Ser Val
1               5                  10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 20
<211> LENGTH: 233
<212> TYPE: PRT
<213> ORGANISM: Homo sapiens

<400> SEQUENCE: 20

Gly Gly Pro Lys Ser Cys Asp Lys Thr His Thr Cys Pro Pro Cys Pro
1               5                  10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45
```

```
Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                 85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Glu Glu Met
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 21
<211> LENGTH: 225
<212> TYPE: PRT
<213> ORGANISM: Homo sapiens

<400> SEQUENCE: 21

Thr His Thr Cys Pro Pro Cys Pro Ala Pro Glu Leu Leu Gly Gly Pro
  1               5                  10                  15

Ser Val Phe Leu Phe Pro Pro Lys Pro Lys Asp Thr Leu Met Ile Ser
             20                  25                  30

Arg Thr Pro Glu Val Thr Cys Val Val Val Asp Val Ser His Glu Asp
         35                  40                  45

Pro Glu Val Lys Phe Asn Trp Tyr Val Asp Gly Val Glu Val His Asn
     50                  55                  60

Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190
```

-continued

```
Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 22
<211> LENGTH: 22
<212> TYPE: PRT
<213> ORGANISM: Unknown
<220> FEATURE:
<223> OTHER INFORMATION: Description of Unknown: Native leader peptide
      sequence

<400> SEQUENCE: 22

Met Gly Arg Gly Leu Leu Arg Gly Leu Trp Pro Leu His Ile Val Leu
1               5                   10                  15

Trp Thr Arg Ile Ala Ser
            20

<210> SEQ ID NO 23
<211> LENGTH: 22
<212> TYPE: PRT
<213> ORGANISM: Unknown
<220> FEATURE:
<223> OTHER INFORMATION: Description of Unknown: Tissue plasminogen
      activator
      (TPA) leader peptide sequence

<400> SEQUENCE: 23

Met Asp Ala Met Lys Arg Gly Leu Cys Cys Val Leu Leu Leu Cys Gly
1               5                   10                  15

Ala Val Phe Val Ser Pro
            20

<210> SEQ ID NO 24
<211> LENGTH: 21
<212> TYPE: PRT
<213> ORGANISM: Apis mellifera

<400> SEQUENCE: 24

Met Lys Phe Leu Val Asn Val Ala Leu Val Phe Met Val Val Tyr Ile
1               5                   10                  15

Ser Tyr Ile Tyr Ala
            20

<210> SEQ ID NO 25
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Val Asn Asn Asp Met Ile Val Thr Asp Asn Asn Gly Ala Val Lys
        35                  40                  45
```

Phe Pro Gln Leu Cys Lys Phe Cys Asp Val Arg Phe Ser Thr Cys Asp
 50                  55                  60

Asn Gln Lys Ser Cys Met Ser Asn Cys Ser Ile Thr Ser Ile Cys Glu
 65                  70                  75                  80

Lys Pro Gln Glu Val Cys Val Ala Val Trp Arg Lys Asn Asp Glu Asn
                 85                  90                  95

Ile Thr Leu Glu Thr Val Cys His Asp Pro Lys Leu Pro Tyr His Lys
                100                 105                 110

Phe Ile Leu Glu Asp Ala Ala Ser Pro Lys Cys Ile Met Lys Glu Lys
            115                 120                 125

Lys Lys Pro Gly Glu Thr Phe Phe Met Cys Ser Cys Ser Ser Asp Glu
130                 135                 140

Cys Asn Asp Asn Ile Ile Phe Ser Glu Glu Tyr Asn Thr Ser Asn Pro
145                 150                 155                 160

Asp Thr Gly Gly Gly Val Glu Cys Pro Pro Cys Pro Ala Pro Pro Val
                165                 170                 175

Ala Gly Pro Ser Val Phe Leu Phe Pro Pro Lys Pro Lys Asp Thr Leu
                180                 185                 190

Met Ile Ser Arg Thr Pro Glu Val Thr Cys Val Val Val Asp Val Ser
            195                 200                 205

His Glu Asp Pro Glu Val Gln Phe Asn Trp Tyr Val Asp Gly Val Glu
210                 215                 220

Val His Asn Ala Lys Thr Lys Pro Arg Glu Glu Gln Phe Asn Ser Thr
225                 230                 235                 240

Phe Arg Val Val Ser Val Leu Thr Val Val His Gln Asp Trp Leu Asn
                245                 250                 255

Gly Lys Glu Tyr Lys Cys Lys Val Ser Asn Lys Gly Leu Pro Ala Pro
                260                 265                 270

Ile Glu Lys Thr Ile Ser Lys Thr Lys Gly Gln Pro Arg Glu Pro Gln
            275                 280                 285

Val Tyr Thr Leu Pro Pro Ser Arg Glu Glu Met Thr Lys Asn Gln Val
290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
                325                 330                 335

Pro Met Leu Asp Ser Asp Gly Ser Phe Phe Leu Tyr Ser Lys Leu Thr
                340                 345                 350

Val Asp Lys Ser Arg Trp Gln Gln Gly Asn Val Phe Ser Cys Ser Val
            355                 360                 365

Met His Glu Ala Leu His Asn His Tyr Thr Gln Lys Ser Leu Ser Leu
370                 375                 380

Ser Pro Gly Lys
385

<210> SEQ ID NO 26
<211> LENGTH: 1164
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
atggatgcaa tgaagagagg gctctgctgt gtgctgctgc tgtgtggagc agtcttcgtt         60

```
tcgcccggcg ccacgatccc accgcacgtt cagaagtcgg ttaataacga catgatagtc    120
actgacaaca acggtgcagt caagtttcca caactgtgta aattttgtga tgtgagattt    180
tccacctgtg acaaccagaa atcctgcatg agcaactgca gcatcacctc catctgtgag    240
aagccacagg aagtctgtgt ggctgtatgg agaaagaatg acgagaacat aacactagag    300
acagtttgcc atgaccccaa gctcccctac cataagttta ttctggaaga tgctgcttct    360
ccaaagtgca ttatgaagga aaaaaaaaag cctggtgaga cttctcttcat gtgttcctgt    420 agctctgatg agtgcaatga caacatcatc ttctcagaag aatataacac cagcaatcct    480
gacaccggtg gtggagtcga gtgcccaccg tgcccagcac cacctgtggc aggaccgtca    540
gtcttcctct tccccccaaa acccaaggac accctcatga tctcccggac ccctgaggtc    600
acgtgcgtgg tggtggacgt gagccacgaa gaccccgagg tccagttcaa ctggtacgtg    660
gacggcgtgg aggtgcataa tgccaagaca aagccacggg aggagcagtt caacagcacg    720
ttccgtgtgg tcagcgtcct caccgtcgtg caccaggact ggctgaacgg caaggagtac    780
aagtgcaagg tctccaacaa aggcctccca gcccccatcg agaaaaccat ctccaaaacc    840
aaagggcagc cccgagaacc acaggtgtac accctgcccc catcccggga ggagatgacc    900
aagaaccagg tcagcctgac ctgcctggtc aaaggcttct accccagcga catcgccgtg    960
gagtgggaga gcaatgggca gccggagaac aactacaaga ccacacctcc catgctggac    1020
tccgacggct ccttcttcct ctacagcaag ctcaccgtgg acaagagcag gtggcagcag    1080
gggaacgtct tctcatgctc cgtgatgcat gaggctctgc acaaccacta cacgcagaag    1140
agcctctccc tgtctccggg taaa                                            1164
```

<210> SEQ ID NO 27
<211> LENGTH: 390
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Val Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Lys
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
    130                 135                 140

Cys Asn Asp Asn Ile Ile Phe Ser Glu Glu Tyr Asn Thr Ser Asn Pro
145                 150                 155                 160
```

```
Asp Thr Gly Gly Gly Thr His Thr Cys Pro Pro Cys Pro Ala Pro Glu
                165                 170                 175
Leu Leu Gly Gly Pro Ser Val Phe Leu Phe Pro Pro Lys Pro Lys Asp
            180                 185                 190
Thr Leu Met Ile Ser Arg Thr Pro Glu Val Thr Cys Val Val Val Asp
        195                 200                 205
Val Ser His Glu Asp Pro Glu Val Lys Phe Asn Trp Tyr Val Asp Gly
    210                 215                 220
Val Glu Val His Asn Ala Lys Thr Lys Pro Arg Glu Glu Gln Tyr Asn
225                 230                 235                 240
Ser Thr Tyr Arg Val Val Ser Val Leu Thr Val Leu His Gln Asp Trp
                245                 250                 255
Leu Asn Gly Lys Glu Tyr Lys Cys Lys Val Ser Asn Lys Ala Leu Pro
            260                 265                 270
Ala Pro Ile Glu Lys Thr Ile Ser Lys Ala Lys Gly Gln Pro Arg Glu
        275                 280                 285
Pro Gln Val Tyr Thr Leu Pro Pro Ser Arg Glu Glu Met Thr Lys Asn
    290                 295                 300
Gln Val Ser Leu Thr Cys Leu Val Lys Gly Phe Tyr Pro Ser Asp Ile
305                 310                 315                 320
Ala Val Glu Trp Glu Ser Asn Gly Gln Pro Glu Asn Asn Tyr Lys Thr
                325                 330                 335
Thr Pro Pro Val Leu Asp Ser Asp Gly Ser Phe Phe Leu Tyr Ser Lys
            340                 345                 350
Leu Thr Val Asp Lys Ser Arg Trp Gln Gln Gly Asn Val Phe Ser Cys
        355                 360                 365
Ser Val Met His Glu Ala Leu His Asn His Tyr Thr Gln Lys Ser Leu
    370                 375                 380
Ser Leu Ser Pro Gly Lys
385                 390

<210> SEQ ID NO 28
<211> LENGTH: 1170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
atggatgcaa tgaagagagg gctctgctgt gtgctgctgc tgtgtggagc agtcttcgtt      60
tcgcccggcg ccacgatccc accgcacgtt cagaagtcgg ttaataacga catgatagtc     120
actgacaaca acggtgcagt caagtttcca caactgtgta aattttgtga tgtgagattt     180
tccacctgtg acaaccagaa atcctgcatg agcaactgca gcatcacctc catctgtgag     240
aagccacagg aagtctgtgt ggctgtatgg agaaagaatg acgagaacat aacactagag     300
acagtttgcc atgaccccaa gctcccctac cataagttta ttctggaaga tgctgcttct     360
ccaaagtgca ttatgaagga aaaaaaaaag cctggtgaga ctttcttcat gtgttcctgt     420
agctctgatg agtgcaatga caacatcatc ttctcagaag aatataacac cagcaatcct     480
gacaccggtg gtggaactca cacatgccca ccgtgcccag cacctgaact cctgggggga     540
ccgtcagtct tcctcttccc cccaaaaccc aaggacaccc tcatgatctc ccggacccct     600
gaggtcacat gcgtggtggt ggacgtgagc cacgaagacc ctgaggtcaa gttcaactgg     660
tacgtggacg gcgtggaggt gcataatgcc aagacaaagc cgcgggagga gcagtacaac     720
```

```
agcacgtacc gtgtggtcag cgtcctcacc gtcctgcacc aggactggct gaatggcaag    780
gagtacaagt gcaaggtctc caacaaagcc ctcccagccc ccatcgagaa aaccatctcc    840
aaagccaaag gcagccccg agaaccacag gtgtacaccc tgccccatc ccgggaggag     900 atgaccaaga accaggtcag cctgacctgc ctggtcaaag gcttctatcc cagcgacatc    960
gccgtggagt gggagagcaa tgggcagccg gagaacaact acaagaccac gcctcccgtg   1020
ctggactccg acggctcctt cttcctctat agcaagctca ccgtggacaa gagcaggtgg   1080
cagcagggga acgtcttctc atgctccgtg atgcatgagg ctctgcacaa ccactacacg   1140
cagaagagcc tctccctgtc cccgggtaaa                                    1170
```

<210> SEQ ID NO 29
<211> LENGTH: 382
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Met Asp Ala Met Lys Arg Gly Leu Cys Cys Val Leu Leu Leu Cys Gly
1               5                   10                  15

Ala Val Phe Val Ser Pro Gly Ala Gln Lys Ser Val Asn Asn Asp Met
            20                  25                  30

Ile Val Thr Asp Asn Asn Gly Ala Val Lys Phe Pro Gln Leu Cys Lys
        35                  40                  45

Phe Cys Asp Val Arg Phe Ser Thr Cys Asp Asn Gln Lys Ser Cys Met
    50                  55                  60

Ser Asn Cys Ser Ile Thr Ser Ile Cys Glu Lys Pro Gln Glu Val Cys
65                  70                  75                  80

Val Ala Val Trp Arg Lys Asn Asp Glu Asn Ile Thr Leu Glu Thr Val
                85                  90                  95

Cys His Asp Pro Lys Leu Pro Tyr His Asp Phe Ile Leu Glu Asp Ala
            100                 105                 110

Ala Ser Pro Lys Cys Ile Met Lys Glu Lys Lys Lys Pro Gly Glu Thr
        115                 120                 125

Phe Phe Met Cys Ser Cys Ser Ser Asp Glu Cys Asn Asp Asn Ile Ile
    130                 135                 140

Phe Ser Glu Glu Tyr Asn Thr Ser Asn Pro Asp Thr Gly Gly Gly Val
145                 150                 155                 160

Glu Cys Pro Pro Cys Pro Ala Pro Val Ala Gly Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
        195                 200                 205

Gln Phe Asn Trp Tyr Val Asp Gly Val Glu Val His Asn Ala Lys Thr
    210                 215                 220

Lys Pro Arg Glu Glu Gln Phe Asn Ser Thr Phe Arg Val Val Ser Val
225                 230                 235                 240

Leu Thr Val Val His Gln Asp Trp Leu Asn Gly Lys Glu Tyr Lys Cys
                245                 250                 255

Lys Val Ser Asn Lys Gly Leu Pro Ala Pro Ile Glu Lys Thr Ile Ser
            260                 265                 270
```

Lys Thr Lys Gly Gln Pro Arg Glu Pro Gln Val Tyr Thr Leu Pro Pro
            275                 280                 285

Ser Arg Glu Glu Met Thr Lys Asn Gln Val Ser Leu Thr Cys Leu Val
        290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Met Leu Asp Ser Asp
                325                 330                 335

Gly Ser Phe Phe Leu Tyr Ser Lys Leu Thr Val Asp Lys Ser Arg Trp
            340                 345                 350

Gln Gln Gly Asn Val Phe Ser Cys Ser Val Met His Glu Ala Leu His
        355                 360                 365

Asn His Tyr Thr Gln Lys Ser Leu Ser Leu Ser Pro Gly Lys
    370                 375                 380

<210> SEQ ID NO 30
<211> LENGTH: 1146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
atggatgcaa tgaagagagg ctctgctgt gtgctgctgc tgtgtggagc agtcttcgtt        60
tcgcccggcg cccagaagtc ggttaataac gacatgatag tcactgacaa caacggtgca     120
gtcaagtttc cacaactgtg taaattttgt gatgtgagat tttccacctg tgacaaccag     180
aaatcctgca tgagcaactg cagcatcacc tccatctgtg agaagccaca ggaagtctgt     240
gtggctgtat ggaaaagaa tgacgagaac ataacactag acagtttg ccatgacccc       300 aagctcccct accatgactt tattctggaa gatgctgctt ctccaaagtg cattatgaag     360
gaaaaaaaaa agcctggtga gactttcttc atgtgttcct gtagctctga tgagtgcaat     420
gacaacatca tcttctcaga agaatataac accagcaatc ctgacaccgg tggtggagtc     480
gagtgcccac cgtgcccagc accacctgtg gcaggaccgt cagtcttcct cttccccca      540 aaacccaagg acaccctcat gatctcccgg accctgagg tcacgtgcgt ggtggtggac      600
gtgagccacg aagaccccga ggtccagttc aactggtacg tggacggcgt ggaggtgcat     660
aatgccaaga caaagccacg ggaggagcag ttcaacagca cgttccgtgt ggtcagcgtc     720
ctcaccgtcg tgcaccagga ctggctgaac ggcaaggagt acaagtgcaa ggtctccaac     780
aaaggcctcc cagcccccat cgagaaaacc atctccaaaa ccaaagggca gccccgagaa     840
ccacaggtgt acaccctgcc cccatcccgg gaggagatga ccaagaacca ggtcagcctg     900
acctgcctgg tcaaaggctt ctaccccagc gacatcgccg tggagtggga gagcaatggg     960
cagccggaga acaactacaa gaccacacct cccatgctgg actccgacgg ctccttcttc    1020
ctctacagca agctcaccgt ggacaagagc aggtggcagc aggggaacgt cttctcatgc    1080
tccgtgatgc atgaggctct gcacaaccac tacacgcaga gagcctctc cctgtctccg     1140 ggtaaa                                                                1146

<210> SEQ ID NO 31
<211> LENGTH: 384
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Met Asp Ala Met Lys Arg Gly Leu Cys Cys Val Leu Leu Leu Cys Gly
1               5                   10                  15

Ala Val Phe Val Ser Pro Gly Ala Gln Lys Ser Val Asn Asn Asp Met
            20                  25                  30

Ile Val Thr Asp Asn Asn Gly Ala Val Lys Phe Pro Gln Leu Cys Lys
        35                  40                  45

Phe Cys Asp Val Arg Phe Ser Thr Cys Asp Asn Gln Lys Ser Cys Met
    50                  55                  60

Ser Asn Cys Ser Ile Thr Ser Ile Cys Glu Lys Pro Gln Glu Val Cys
65                  70                  75                  80

Val Ala Val Trp Arg Lys Asn Asp Glu Asn Ile Thr Leu Glu Thr Val
                85                  90                  95

Cys His Asp Pro Lys Leu Pro Tyr His Asp Phe Ile Leu Glu Asp Ala
            100                 105                 110

Ala Ser Pro Lys Cys Ile Met Lys Glu Lys Lys Pro Gly Glu Thr
        115                 120                 125

Phe Phe Met Cys Ser Cys Ser Ser Asp Glu Cys Asn Asp Asn Ile Ile
130                 135                 140

Phe Ser Glu Glu Tyr Asn Thr Ser Asn Pro Asp Thr Gly Gly Gly Thr
145                 150                 155                 160

His Thr Cys Pro Pro Cys Pro Ala Pro Glu Leu Leu Gly Gly Pro Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser His Glu Asp Pro
        195                 200                 205

Glu Val Lys Phe Asn Trp Tyr Val Asp Gly Val Glu Val His Asn Ala
    210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
            260                 265                 270

Ile Ser Lys Ala Lys Gly Gln Pro Arg Glu Pro Gln Val Tyr Thr Leu
        275                 280                 285

Pro Pro Ser Arg Glu Glu Met Thr Lys Asn Gln Val Ser Leu Thr Cys
    290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
            340                 345                 350

Arg Trp Gln Gln Gly Asn Val Phe Ser Cys Ser Val Met His Glu Ala
        355                 360                 365

Leu His Asn His Tyr Thr Gln Lys Ser Leu Ser Leu Ser Pro Gly Lys
    370                 375                 380

<210> SEQ ID NO 32
<211> LENGTH: 1152

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
atggatgcaa tgaagagagg gctctgctgt gtgctgctgc tgtgtggagc agtcttcgtt      60
tcgcccggcg cccagaagtc ggttaataac gacatgatag tcactgacaa caacggtgca     120
gtcaagtttc cacaactgtg taaattttgt gatgtgagat tttccacctg tgacaaccag     180
aaatcctgca tgagcaactg cagcatcacc tccatctgtg agaagccaca ggaagtctgt     240
gtggctgtat ggagaaagaa tgacgagaac ataacactag agacagtttg ccatgacccc     300
aagctcccct accatgactt tattctggaa gatgctgctt ctccaaagtg cattatgaag     360
gaaaaaaaaa agcctggtga acttttcttc atgtgttcct gtagctctga tgagtgcaat     420
gacaacatca tcttctcaga agaatataac accagcaatc ctgacaccgg tggtggaact     480
cacacatgcc caccgtgccc agcacctgaa ctcctggggg gaccgtcagt cttcctcttc     540
ccccaaaac ccaaggacac cctcatgatc tcccggaccc ctgaggtcac atgcgtggtg      600
gtggacgtga gccacgaaga ccctgaggtc aagttcaact ggtacgtgga cggcgtggag     660
gtgcataatg ccaagacaaa gccgcgggag gagcagtaca acagcacgta ccgtgtggtc     720
agcgtcctca ccgtcctgca ccaggactgg ctgaatggca aggagtacaa gtgcaaggtc     780
tccaacaaag ccctcccagc ccccatcgag aaaaccatct ccaaagccaa agggcagccc     840
cgagaaccac aggtgtacac cctgccccca tcccgggagg atgaccaaga accaggtc     900
agcctgacct gcctggtcaa aggcttctat cccagcgaca tcgccgtgga gtgggagagc     960
aatgggcagc cggagaacaa ctacaagacc acgcctcccg tgctggactc cgacggctcc    1020
ttcttcctct atagcaagct caccgtggac aagagcaggt ggcagcaggg gaacgtcttc    1080
tcatgctccg tgatgcatga ggctctgcac aaccactaca cgcagaagag cctctccctg    1140
tccccgggta aa                                                        1152
```

<210> SEQ ID NO 33
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Met Asp Ala Met Lys Arg Gly Leu Cys Cys Val Leu Leu Leu Cys Gly
1               5                   10                  15

Ala Val Phe Val Ser Pro Gly Ala Asp Met Ile Val Thr Asp Asn Asn
            20                  25                  30

Gly Ala Val Lys Phe Pro Gln Leu Cys Lys Phe Cys Asp Val Arg Phe
        35                  40                  45

Ser Thr Cys Asp Asn Gln Lys Ser Cys Met Ser Asn Cys Ser Ile Thr
    50                  55                  60

Ser Ile Cys Glu Lys Pro Gln Glu Val Cys Val Ala Val Trp Arg Lys
65                  70                  75                  80

Asn Asp Glu Asn Ile Thr Leu Glu Thr Val Cys His Asp Pro Lys Leu
                85                  90                  95

Pro Tyr His Asp Phe Ile Leu Glu Asp Ala Ala Ser Pro Lys Cys Ile
            100                 105                 110
```

```
Met Lys Glu Lys Lys Pro Gly Glu Thr Phe Phe Met Cys Ser Cys
        115                 120                 125
Ser Ser Asp Glu Cys Asn Asp Asn Ile Ile Phe Ser Glu Glu Tyr Asn
    130                 135                 140
Thr Ser Asn Pro Asp Thr Gly Gly Val Glu Cys Pro Pro Cys Pro
145                 150                 155                 160
Ala Pro Pro Val Ala Gly Pro Ser Val Phe Leu Phe Pro Pro Lys Pro
                165                 170                 175
Lys Asp Thr Leu Met Ile Ser Arg Thr Pro Glu Val Thr Cys Val Val
            180                 185                 190
Val Asp Val Ser His Glu Asp Pro Glu Val Gln Phe Asn Trp Tyr Val
            195                 200                 205
Asp Gly Val Glu Val His Asn Ala Lys Thr Lys Pro Arg Glu Glu Gln
        210                 215                 220
Phe Asn Ser Thr Phe Arg Val Val Ser Val Leu Thr Val Val His Gln
225                 230                 235                 240
Asp Trp Leu Asn Gly Lys Glu Tyr Lys Cys Lys Val Ser Asn Lys Gly
                245                 250                 255
Leu Pro Ala Pro Ile Glu Lys Thr Ile Ser Lys Thr Lys Gly Gln Pro
            260                 265                 270
Arg Glu Pro Gln Val Tyr Thr Leu Pro Pro Ser Arg Glu Glu Met Thr
        275                 280                 285
Lys Asn Gln Val Ser Leu Thr Cys Leu Val Lys Gly Phe Tyr Pro Ser
        290                 295                 300
Asp Ile Ala Val Glu Trp Glu Ser Asn Gly Gln Pro Glu Asn Asn Tyr
305                 310                 315                 320
Lys Thr Thr Pro Pro Met Leu Asp Ser Asp Gly Ser Phe Phe Leu Tyr
                325                 330                 335
Ser Lys Leu Thr Val Asp Lys Ser Arg Trp Gln Gln Gly Asn Val Phe
            340                 345                 350
Ser Cys Ser Val Met His Glu Ala Leu His Asn His Tyr Thr Gln Lys
        355                 360                 365
Ser Leu Ser Leu Ser Pro Gly Lys
        370                 375

<210> SEQ ID NO 34
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
atggatgcaa tgaagagagg gctctgctgt gtgctgctgc tgtgtggagc agtcttcgtt      60
tcgcccggcg ccgacatgat agtcactgac aacaacggtg cagtcaagtt tccacaactg     120
tgtaaatttt gtgatgtgag attttccacc tgtgacaacc agaaatcctg catgagcaac     180
tgcagcatca cctccatctg tgagaagcca caggaagtct gtgtggctgt atggagaaag     240
aatgacgaga acataacact agagacagtt gccatgacc ccaagctccc ctaccatgac     300
tttattctgg aagatgctgc ttctccaaag tgcattatga aggaaaaaaa aaagcctggt     360 gagctttct tcatgtgttc ctgtagctct gatgagtgca atgacaacat catcttctca     420
gaagaatata acaccagcaa tcctgacacc ggtggtggag tcgagtgccc accgtgccca     480
```

```
gcaccacctg tggcaggacc gtcagtcttc ctcttccccc caaaacccaa ggacaccctc      540
atgatctccc ggaccctga ggtcacgtgc gtggtggtgg acgtgagcca cgaagacccc       600
gaggtccagt tcaactggta cgtggacggc gtggaggtgc ataatgccaa gacaaagcca      660
cgggaggagc agttcaacag cacgttccgt gtggtcagcg tcctcaccgt cgtgcaccag      720
gactggctga acggcaagga gtacaagtgc aaggtctcca acaaaggcct cccagccccc      780
atcgagaaaa ccatctccaa aaccaaaggg cagccccgag aaccacaggt gtacaccctg      840
cccccatccc gggaggagat gaccaagaac caggtcagcc tgacctgcct ggtcaaaggc      900
ttctacccca gcgacatcgc cgtggagtgg gagagcaatg ggcagccgga gaacaactac      960
aagaccacac ctcccatgct ggactccgac ggctccttct tcctctacag caagctcacc     1020
gtggacaaga gcaggtggca gcaggggaac gtcttctcat gctccgtgat gcatgaggct     1080
ctgcacaacc actacacgca gaagagcctc tccctgtctc cgggtaaa                  1128
```

<210> SEQ ID NO 35
<211> LENGTH: 378
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 35

```
Met Asp Ala Met Lys Arg Gly Leu Cys Cys Val Leu Leu Leu Cys Gly
1               5                   10                  15

Ala Val Phe Val Ser Pro Gly Ala Asp Met Ile Val Thr Asp Asn Asn
            20                  25                  30

Gly Ala Val Lys Phe Pro Gln Leu Cys Lys Phe Cys Asp Val Arg Phe
        35                  40                  45

Ser Thr Cys Asp Asn Gln Lys Ser Cys Met Ser Asn Cys Ser Ile Thr
    50                  55                  60

Ser Ile Cys Glu Lys Pro Gln Glu Val Cys Val Ala Val Trp Arg Lys
65                  70                  75                  80

Asn Asp Glu Asn Ile Thr Leu Glu Thr Val Cys His Asp Pro Lys Leu
                85                  90                  95

Pro Tyr His Asp Phe Ile Leu Glu Asp Ala Ala Ser Pro Lys Cys Ile
            100                 105                 110

Met Lys Glu Lys Lys Lys Pro Gly Glu Thr Phe Phe Met Cys Ser Cys
        115                 120                 125

Ser Ser Asp Glu Cys Asn Asp Asn Ile Ile Phe Ser Glu Glu Tyr Asn
    130                 135                 140

Thr Ser Asn Pro Asp Thr Gly Gly Gly Thr His Thr Cys Pro Pro Cys
145                 150                 155                 160

Pro Ala Pro Glu Leu Leu Gly Gly Pro Ser Val Phe Leu Phe Pro Pro
                165                 170                 175

Lys Pro Lys Asp Thr Leu Met Ile Ser Arg Thr Pro Glu Val Thr Cys
            180                 185                 190

Val Val Val Asp Val Ser His Glu Asp Pro Glu Val Lys Phe Asn Trp
        195                 200                 205

Tyr Val Asp Gly Val Glu Val His Asn Ala Lys Thr Lys Pro Arg Glu
    210                 215                 220

Glu Gln Tyr Asn Ser Thr Tyr Arg Val Val Ser Val Leu Thr Val Leu
225                 230                 235                 240

His Gln Asp Trp Leu Asn Gly Lys Glu Tyr Lys Cys Lys Val Ser Asn
```

245                 250                 255
Lys Ala Leu Pro Ala Pro Ile Glu Lys Thr Ile Ser Lys Ala Lys Gly
                260                 265                 270

Gln Pro Arg Glu Pro Gln Val Tyr Thr Leu Pro Pro Ser Arg Glu Glu
            275                 280                 285

Met Thr Lys Asn Gln Val Ser Leu Thr Cys Leu Val Lys Gly Phe Tyr
        290                 295                 300

Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
                325                 330                 335

Leu Tyr Ser Lys Leu Thr Val Asp Lys Ser Arg Trp Gln Gln Gly Asn
            340                 345                 350

Val Phe Ser Cys Ser Val Met His Glu Ala Leu His Asn His Tyr Thr
        355                 360                 365

Gln Lys Ser Leu Ser Leu Ser Pro Gly Lys
    370                 375

<210> SEQ ID NO 36
<211> LENGTH: 1134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
atggatgcaa tgaagagagg gctctgctgt gtgctgctgc tgtgtggagc agtcttcgtt      60
tcgcccggcg ccgacatgat agtcactgac aacaacggtg cagtcaagtt tccacaactg     120
tgtaaatttt gtgatgtgag attttccacc tgtgacaacc agaaatcctg catgagcaac     180
tgcagcatca cctccatctg tgagaagcca caggaagtct gtgtggctgt atggagaaag     240
aatgacgaga acataaacact agagacagtt tgccatgacc ccaagctccc ctaccatgac     300
tttattctgg aagatgctgc ttctccaaag tgcattatga aggaaaaaaa aaagcctggt     360
gagactttct tcatgtgttc ctgtagctct gatgagtgca atgacaacat catcttctca     420
gaagaatata caccagcaa tcctgacacc ggtggtggaa ctcacacatg cccaccgtgc     480
ccagcacctg aactcctggg gggaccgtca gtcttcctct tccccccaaa acccaaggac     540
accctcatga tctcccggac ccctgaggtc acatgcgtgg tggtggacgt gagccacgaa     600
gaccctgagg tcaagttcaa ctggtacgtg gacggcgtgg aggtgcataa tgccaagaca     660
aagccgcggg aggagcagta caacagcacg taccgtgtgg tcagcgtcct caccgtcctg     720
caccaggact ggctgaatgg caaggagtac aagtgcaagg tctccaacaa agccctccca     780
gcccccatcg agaaaaccat ctccaaagcc aagggcagc cccgagaacc acaggtgtac     840
accctgcccc catcccggga ggagatgacc aagaaccagg tcagcctgac ctgcctggtc     900
aaaggcttct atcccagcga catcgccgtg gagtgggaga gcaatgggca gccggagaac     960
aactacaaga ccacgcctcc cgtgctggac tccgacggct ccttcttcct ctatagcaag    1020
ctcaccgtgg acaagagcag gtggcagcag gggaacgtct tctcatgctc cgtgatgcat    1080
gaggctctgc acaaccacta cacgcagaag agcctctccc tgtcccccgg gtaaa         1134

<210> SEQ ID NO 37
<211> LENGTH: 382
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 37

| | | | | | | | | | | | | | | |
|---|---|---|---|---|---|---|---|---|---|---|---|---|---|---|
| Met | Asp | Ala | Met | Lys | Arg | Gly | Leu | Cys | Cys | Val | Leu | Leu | Cys | Gly |
| 1 | | | | 5 | | | | | 10 | | | | | 15 |
| Ala | Val | Phe | Val | Ser | Pro | Gly | Ala | Thr | Ile | Pro | Pro | His | Val | Gln | Lys |
| | | | 20 | | | | | 25 | | | | | 30 | | |
| Ser | Val | Asn | Asn | Asp | Met | Ile | Val | Thr | Asp | Asn | Asn | Gly | Ala | Val | Lys |
| | | | 35 | | | | | 40 | | | | | 45 | | |
| Phe | Pro | Gln | Leu | Cys | Lys | Phe | Cys | Asp | Val | Arg | Phe | Ser | Thr | Cys | Asp |
| | 50 | | | | | 55 | | | | | 60 | | | | |
| Asn | Gln | Lys | Ser | Cys | Met | Ser | Asn | Cys | Ser | Ile | Thr | Ser | Ile | Cys | Glu |
| 65 | | | | | 70 | | | | | 75 | | | | | 80 |
| Lys | Pro | Gln | Glu | Val | Cys | Val | Ala | Val | Trp | Arg | Lys | Asn | Asp | Glu | Asn |
| | | | | 85 | | | | | 90 | | | | | 95 | |
| Ile | Thr | Leu | Glu | Thr | Val | Cys | His | Asp | Pro | Lys | Leu | Pro | Tyr | His | Asp |
| | | | | 100 | | | | | 105 | | | | | 110 | |
| Phe | Ile | Leu | Glu | Asp | Ala | Ala | Ser | Pro | Lys | Cys | Ile | Met | Lys | Glu | Lys |
| | | | | 115 | | | | | 120 | | | | | 125 | |
| Lys | Lys | Pro | Gly | Glu | Thr | Phe | Phe | Met | Cys | Ser | Cys | Ser | Ser | Asp | Glu |
| | 130 | | | | | 135 | | | | | 140 | | | | |
| Cys | Asn | Asp | Asn | Ile | Ile | Phe | Ser | Glu | Glu | Tyr | Thr | Gly | Gly | Gly | Val |
| 145 | | | | | 150 | | | | | 155 | | | | | 160 |
| Glu | Cys | Pro | Pro | Cys | Pro | Ala | Pro | Pro | Val | Ala | Gly | Pro | Ser | Val | Phe |
| | | | | 165 | | | | | 170 | | | | | 175 | |
| Leu | Phe | Pro | Pro | Lys | Pro | Lys | Asp | Thr | Leu | Met | Ile | Ser | Arg | Thr | Pro |
| | | | 180 | | | | | 185 | | | | | 190 | | |
| Glu | Val | Thr | Cys | Val | Val | Val | Asp | Val | Ser | His | Glu | Asp | Pro | Glu | Val |
| | | | 195 | | | | | 200 | | | | | 205 | | |
| Gln | Phe | Asn | Trp | Tyr | Val | Asp | Gly | Val | Glu | Val | His | Asn | Ala | Lys | Thr |
| | 210 | | | | | 215 | | | | | 220 | | | | |
| Lys | Pro | Arg | Glu | Glu | Gln | Phe | Asn | Ser | Thr | Phe | Arg | Val | Val | Ser | Val |
| 225 | | | | | 230 | | | | | 235 | | | | | 240 |
| Leu | Thr | Val | Val | His | Gln | Asp | Trp | Leu | Asn | Gly | Lys | Glu | Tyr | Lys | Cys |
| | | | | 245 | | | | | 250 | | | | | 255 | |
| Lys | Val | Ser | Asn | Lys | Gly | Leu | Pro | Ala | Pro | Ile | Glu | Lys | Thr | Ile | Ser |
| | | | 260 | | | | | 265 | | | | | 270 | | |
| Lys | Thr | Lys | Gly | Gln | Pro | Arg | Glu | Pro | Gln | Val | Tyr | Thr | Leu | Pro | Pro |
| | | 275 | | | | | 280 | | | | | 285 | | | |
| Ser | Arg | Glu | Glu | Met | Thr | Lys | Asn | Gln | Val | Ser | Leu | Thr | Cys | Leu | Val |
| | 290 | | | | | 295 | | | | | 300 | | | | |
| Lys | Gly | Phe | Tyr | Pro | Ser | Asp | Ile | Ala | Val | Glu | Trp | Glu | Ser | Asn | Gly |
| 305 | | | | | 310 | | | | | 315 | | | | | 320 |
| Gln | Pro | Glu | Asn | Asn | Tyr | Lys | Thr | Thr | Pro | Pro | Met | Leu | Asp | Ser | Asp |
| | | | | 325 | | | | | 330 | | | | | 335 | |
| Gly | Ser | Phe | Phe | Leu | Tyr | Ser | Lys | Leu | Thr | Val | Asp | Lys | Ser | Arg | Trp |
| | | | 340 | | | | | 345 | | | | | 350 | | |
| Gln | Gln | Gly | Asn | Val | Phe | Ser | Cys | Ser | Val | Met | His | Glu | Ala | Leu | His |
| | | 355 | | | | | 360 | | | | | 365 | | | |
| Asn | His | Tyr | Thr | Gln | Lys | Ser | Leu | Ser | Leu | Ser | Pro | Gly | Lys |
| | 370 | | | | | 375 | | | | | 380 | | |

<210> SEQ ID NO 38
<211> LENGTH: 1146
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

```
atggatgcaa tgaagagagg gctctgctgt gtgctgctgc tgtgtggagc agtcttcgtt      60
tcgcccggcg ccacgatccc accgcacgtt cagaagtcgg ttaataacga catgatagtc     120
actgacaaca acggtgcagt caagtttcca caactgtgta aattttgtga tgtgagattt     180
tccacctgtg acaaccagaa atcctgcatg agcaactgca gcatcacctc catctgtgag     240
aagccacagg aagtctgtgt ggctgtatgg agaaagaatg acgagaacat aacactagag     300
acagtttgcc atgaccccaa gctcccctac catgacttta ttctggaaga tgctgcttct     360
ccaaagtgca ttatgaagga aaaaaaaaag cctggtgaga ctttcttcat gtgttcctgt     420
agctctgatg agtgcaatga acacatcatc ttctcagaag aatataccgg tggtggagtc     480
gagtgcccac cgtgcccagc accacctgtg gcaggaccgt cagtcttcct cttcccccca     540
aaacccaagg acaccctcat gatctcccgg acccctgagg tcacgtgcgt ggtggtggac     600
gtgagccacg aagaccccga ggtccagttc aactggtacg tggacggcgt ggaggtgcat     660
aatgccaaga caaagccacg ggaggagcag ttcaacagca cgttccgtgt ggtcagcgtc     720
ctcaccgtcg tgcaccagga ctggctgaac ggcaaggagt acaagtgcaa ggtctccaac     780
aaaggcctcc cagcccccat cgagaaaacc atctccaaaa ccaaagggca gccccgagaa     840
ccacaggtgt acaccctgcc cccatcccgg gaggagatga ccaagaacca ggtcagcctg     900
acctgcctgg tcaaaggctt ctaccccagc gacatcgccg tggagtggga gagcaatggg     960
cagccggaga acaactacaa gaccacacct cccatgctgg actccgacgg ctccttcttc    1020
ctctacagca agctcaccgt ggacaagagc aggtggcagc aggggaacgt cttctcatgc    1080
tccgtgatgc atgaggctct gcacaaccac tacacgcaga agagcctctc cctgtctccg    1140
ggtaaa                                                                1146
```

<210> SEQ ID NO 39
<211> LENGTH: 384
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Val Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95
```

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
            115                 120                 125

Lys Lys Pro Gly Glu Thr Phe Phe Met Cys Ser Cys Ser Ser Asp Glu
130                 135                 140

Cys Asn Asp Asn Ile Ile Phe Ser Glu Glu Tyr Thr Gly Gly Thr
145                 150                 155                 160

His Thr Cys Pro Pro Cys Pro Ala Pro Glu Leu Leu Gly Gly Pro Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser His Glu Asp Pro
            195                 200                 205

Glu Val Lys Phe Asn Trp Tyr Val Asp Gly Val Glu Val His Asn Ala
            210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
            260                 265                 270

Ile Ser Lys Ala Lys Gly Gln Pro Arg Glu Pro Gln Val Tyr Thr Leu
            275                 280                 285

Pro Pro Ser Arg Glu Glu Met Thr Lys Asn Gln Val Ser Leu Thr Cys
290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
            340                 345                 350

Arg Trp Gln Gln Gly Asn Val Phe Ser Cys Ser Val Met His Glu Ala
            355                 360                 365

Leu His Asn His Tyr Thr Gln Lys Ser Leu Ser Leu Ser Pro Gly Lys
            370                 375                 380

<210> SEQ ID NO 40
<211> LENGTH: 1152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
atggatgcaa tgaagagagg gctctgctgt gtgctgctgc tgtgtggagc agtcttcgtt     60
tcgcccggcg ccacgatccc accgcacgtt cagaagtcgg ttaataacga catgatagtc    120
actgacaaca acggtgcagt caagtttcca caactgtgta aattttgtga tgtgagattt    180
tccacctgtg acaaccagaa atcctgcatg agcaactgca gcatcacctc catctgtgag    240
aagccacagg aagtctgtgt ggctgtatgg agaaagaatg acgagaacat aacactagag    300
acagtttgcc atgaccccaa gctcccctac atgactttta ttctggaaga tgctgcttct    360
ccaaagtgca ttatgaagga aaaaaaaaag cctggtgaga cttttcttca tgttcctgt     420

```
agctctgatg agtgcaatga caacatcatc ttctcagaag aatataccgg tggtggaact    480
cacacatgcc caccgtgccc agcacctgaa ctcctggggg gaccgtcagt cttcctcttc    540
cccccaaaac ccaaggacac cctcatgatc tcccggaccc ctgaggtcac atgcgtggtg    600
gtggacgtga gccacgaaga ccctgaggtc aagttcaact ggtacgtgga cggcgtggag    660
gtgcataatg ccaagacaaa gccgcgggag gagcagtaca acagcacgta ccgtgtggtc    720
agcgtcctca ccgtcctgca ccaggactgg ctgaatggca aggagtacaa gtgcaaggtc    780
tccaacaaag ccctcccagc ccccatcgag aaaaccatct ccaaagccaa agggcagccc    840
cgagaaccac aggtgtacac cctgccccca tcccgggagg agatgaccaa gaaccaggtc    900
agcctgacct gcctggtcaa aggcttctat cccagcgaca tcgccgtgga gtgggagagc    960
aatgggcagc cggagaacaa ctacaagacc acgcctcccg tgctggactc cgacggctcc   1020
ttcttcctct atagcaagct caccgtggac aagagcaggt ggcagcaggg gaacgtcttc   1080
tcatgctccg tgatgcatga ggctctgcac aaccactaca cgcagaagag cctctccctg   1140
tccccgggta aa                                                       1152
```

<210> SEQ ID NO 41
<211> LENGTH: 382
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Val Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asp Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
    130                 135                 140

Cys Asn Asp Asn Ile Ile Phe Ser Glu Glu Tyr Thr Gly Gly Gly Val
145                 150                 155                 160

Glu Cys Pro Pro Cys Pro Ala Pro Pro Val Ala Gly Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
        195                 200                 205

Gln Phe Asn Trp Tyr Val Asp Gly Val Glu Val His Asn Ala Lys Thr
    210                 215                 220

Lys Pro Arg Glu Glu Gln Phe Asn Ser Thr Phe Arg Val Val Ser Val
225                 230                 235                 240

Leu Thr Val Val His Gln Asp Trp Leu Asn Gly Lys Glu Tyr Lys Cys
            245                 250                 255

Lys Val Ser Asn Lys Gly Leu Pro Ala Pro Ile Glu Lys Thr Ile Ser
        260                 265                 270

Lys Thr Lys Gly Gln Pro Arg Glu Pro Gln Val Tyr Thr Leu Pro Pro
    275                 280                 285

Ser Arg Glu Glu Met Thr Lys Asn Gln Val Ser Leu Thr Cys Leu Val
290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Met Leu Asp Ser Asp
            325                 330                 335

Gly Ser Phe Phe Leu Tyr Ser Lys Leu Thr Val Asp Lys Ser Arg Trp
        340                 345                 350

Gln Gln Gly Asn Val Phe Ser Cys Ser Val Met His Glu Ala Leu His
    355                 360                 365

Asn His Tyr Thr Gln Lys Ser Leu Ser Leu Ser Pro Gly Lys
370                 375                 380

<210> SEQ ID NO 42
<211> LENGTH: 1146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
atggatgcaa tgaagagagg ctctgctgtg tgctgctgct gtgtggagca gtcttcgtt      60 tcgcccggcg ccacgatccc accgcacgtt cagaagtcgg ttaataacga catgatagtc    120
actgacaaca acggtgcagt caagtttcca caactgtgta aattttgtga tgtgagattt    180
tccacctgtg acaaccagaa atcctgcatg agcgactgca gcatcacctc catctgtgag    240
aagccacagg aagtctgtgt ggctgtatgg agaaagaatg acgagaacat aacactagag    300
acagtttgcc atgaccccaa gctcccctac catgactta ttctggaaga tgctgcttct    360
ccaaagtgca ttatgaagga aaaaaaaag cctggtgaga ctttcttcat gtgttcctgt    420
agctctgatg agtgcaatga caacatcatc ttctcagaag aatataccgg tggtggagtc    480
gagtgcccac cgtgcccagc accacctgtg caggaccgt cagtcttcct cttcccccca    540
aaacccaagg acaccctcat gatctcccgg acccctgagg tcacgtgcgt ggtggtggac    600
gtgagccacg aagaccccga ggtccagttc aactggtacg tggacggcgt ggaggtgcat    660
aatgccaaga caaagccacg ggaggagcag ttcaacagca cgttccgtgt ggtcagcgtc    720
ctcaccgtcg tgcaccagga ctggctgaac ggcaaggagt acaagtgcaa ggtctccaac    780
aaaggcctcc cagcccccat cgagaaaacc atctccaaaa ccaaagggca gccccgagaa    840
ccacaggtgt acaccctgcc cccatcccgg gaggagatga ccaagaacca ggtcagcctg    900
acctgcctgg tcaaaggctt ctaccccagc gacatcgccg tggagtggga gagcaatggg    960
cagccggaga acaactacaa gaccacacct cccatgctgg actccgacgg ctccttcttc   1020
ctctacagca agctcaccgt ggacaagagc aggtggcagc aggggaacgt cttctcatgc   1080
tccgtgatgc atgaggctct gcacaaccac tacacgcaga agagcctctc cctgtctccg   1140
ggtaaa                                                              1146

<210> SEQ ID NO 43
<211> LENGTH: 384
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Asp Ala Met Lys Arg Gly Leu Cys Cys Val Leu Leu Cys Gly
1               5                   10                  15

Ala Val Phe Val Ser Pro Gly Ala Thr Ile Pro Pro His Val Gln Lys
            20                  25                  30

Ser Val Asn Asn Asp Met Ile Val Thr Asp Asn Gly Ala Val Lys
35                  40                  45

Phe Pro Gln Leu Cys Lys Phe Cys Asp Val Arg Phe Ser Thr Cys Asp
    50                  55                  60

Asn Gln Lys Ser Cys Met Ser Asp Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
    130                 135                 140

Cys Asn Asp Asn Ile Ile Phe Ser Glu Glu Tyr Thr Gly Gly Gly Thr
145                 150                 155                 160

His Thr Cys Pro Pro Cys Pro Ala Pro Glu Leu Leu Gly Gly Pro Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser His Glu Asp Pro
        195                 200                 205

Glu Val Lys Phe Asn Trp Tyr Val Asp Gly Val Glu Val His Asn Ala
    210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
            260                 265                 270

Ile Ser Lys Ala Lys Gly Gln Pro Arg Glu Pro Gln Val Tyr Thr Leu
        275                 280                 285

Pro Pro Ser Arg Glu Glu Met Thr Lys Asn Gln Val Ser Leu Thr Cys
    290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Val Leu Asp
                325                 330                 335

Ser Asp Gly Ser Phe Phe Leu Tyr Ser Lys Leu Thr Val Asp Lys Ser
            340                 345                 350

Arg Trp Gln Gln Gly Asn Val Phe Ser Cys Ser Val Met His Glu Ala
         355                 360                 365

Leu His Asn His Tyr Thr Gln Lys Ser Leu Ser Leu Ser Pro Gly Lys
     370                 375                 380

<210> SEQ ID NO 44
<211> LENGTH: 1152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
atggatgcaa tgaagagagg gctctgctgt gtgctgctgc tgtgtggagc agtcttcgtt      60
tcgcccggcg ccacgatccc accgcacgtt cagaagtcgg ttaataacga catgatagtc     120
actgacaaca acggtgcagt caagtttcca caactgtgta aattttgtga tgtgagattt     180
tccacctgtg acaaccagaa atcctgcatg agcgactgca gcatcacctc catctgtgag     240
aagccacagg aagtctgtgt ggctgtatgg agaaagaatg acgagaacat aacactagag     300
acagtttgcc atgaccccaa gctcccctac catgacttta ttctggaaga tgctgcttct     360
ccaaagtgca ttatgaagga aaaaaaaaag cctggtgaga ctttcttcat gtgttcctgt     420
agctctgatg agtgcaatga caacatcatc ttctcagaag aatataccgg tggtggaact     480
cacacatgcc accgtgccc  agcacctgaa ctcctggggg gaccgtcagt cttcctcttc     540
cccccaaaac ccaaggacac cctcatgatc tcccggaccc ctgaggtcac atgcgtggtg     600
gtggacgtga gccacgaaga ccctgaggtc aagttcaact ggtacgtgga cggcgtggag     660
gtgcataatg ccaagacaaa gccgcgggag gagcagtaca acagcacgta ccgtgtggtc     720
agcgtcctca ccgtcctgca ccaggactgg ctgaatggca aggagtacaa gtgcaaggtc     780
tccaacaaag ccctcccagc ccccatcgag aaaaccatct ccaaagccaa agggcagccc     840
cgagaaccac aggtgtacac cctgcccca tcccgggagg agatgaccaa gaaccaggtc     900
agcctgacct gcctggtcaa aggcttctat cccagcgaca tcgccgtgga gtgggagagc     960
aatgggcagc cggagaacaa ctacaagacc acgcctcccg tgctggactc cgacggctcc    1020
ttcttcctct atagcaagct caccgtggac aagagcaggt ggcagcaggg gaacgtcttc    1080
tcatgctccg tgatgcatga ggctctgcac aaccactaca cgcagaagag cctctccctg    1140
tccccgggta aa                                                         1152

<210> SEQ ID NO 45
<211> LENGTH: 35
<212> TYPE: PRT
<213> ORGANISM: Homo sapiens

<400> SEQUENCE: 45

Gln Lys Ser Asp Val Glu Met Glu Ala Gln Lys Asp Glu Ile Ile Cys
1               5                   10                  15

Pro Ser Cys Asn Arg Thr Ala His Pro Leu Arg His Ile Asn Asn Asp
            20                  25                  30

Met Ile Val
        35

<210> SEQ ID NO 46
<211> LENGTH: 4
<212> TYPE: PRT

<213> ORGANISM: Homo sapiens

<400> SEQUENCE: 46

Asp Met Ile Val
1

<210> SEQ ID NO 47
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Met Ile Val Thr Asp Asn Gly Ala Val Lys Phe Pro Gln Leu
1               5                   10                  15

Cys Lys Phe Cys Asp Val Arg Phe Ser Thr Cys Asp Asn Gln Lys Ser
            20                  25                  30

Cys Met Ser Asn Cys Ser Ile Thr Ser Ile Cys Glu Lys Pro Gln Glu
        35                  40                  45

Val Cys Val Ala Val Trp Arg Lys Asn Asp Glu Asn Ile Thr Leu Glu
50                  55                  60

Thr Val Cys His Asp Pro Lys Leu Pro Tyr His Asp Phe Ile Leu Glu
65                  70                  75                  80

Asp Ala Ser Pro Lys Cys Ile Met Lys Glu Lys Lys Pro Gly
                85                  90                  95

Glu Thr Phe Phe Met Cys Ser Cys Ser Ser Asp Glu Cys Asn Asp Asn
                100                 105                 110

Ile Ile Phe Ser Glu Glu Tyr
        115

<210> SEQ ID NO 48
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Lys Ser Val Asn Asn Asp Met Ile Val Thr Asp Asn Asn Gly Ala
1               5                   10                  15

Val Lys Phe Pro Gln Leu Cys Lys Phe Cys Asp Val Arg Phe Ser Thr
            20                  25                  30

Cys Asp Asn Gln Lys Ser Cys Met Ser Asn Cys Ser Ile Thr Ser Ile
        35                  40                  45

Cys Glu Lys Pro Gln Glu Val Cys Val Ala Val Trp Arg Lys Asn Asp
    50                  55                  60

Glu Asn Ile Thr Leu Glu Thr Val Cys His Asp Pro Lys Leu Pro Tyr
65                  70                  75                  80

His Asp Phe Ile Leu Glu Asp Ala Ala Ser Pro Lys Cys Ile Met Lys
                85                  90                  95

Glu Lys Lys Lys Pro Gly Glu Thr Phe Phe Met Cys Ser Cys Ser Ser
                100                 105                 110

Asp Glu Cys Asn Asp Asn Ile Ile Phe Ser Glu Glu Tyr
        115                 120                 125

<210> SEQ ID NO 49

<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Lys Ser Asp Val Glu Met Glu Ala Gln Lys Asp Glu Ile Ile Cys
1               5                   10                  15

Pro Ser Cys Asn Arg Thr Ala His Pro Leu Arg His Ile Asn Asn Asp
            20                  25                  30

Met Ile Val Thr Asp Asn Asn Gly Ala Val Lys Phe Pro Gln Leu Cys
        35                  40                  45

Lys Phe Cys Asp Val Arg Phe Ser Thr Cys Asp Asn Gln Lys Ser Cys
    50                  55                  60

Met Ser Asn Cys Ser Ile Thr Ser Ile Cys Glu Lys Pro Gln Glu Val
65                  70                  75                  80

Cys Val Ala Val Trp Arg Lys Asn Asp Glu Asn Ile Thr Leu Glu Thr
                85                  90                  95

Val Cys His Asp Pro Lys Leu Pro Tyr His Asp Phe Ile Leu Glu Asp
            100                 105                 110

Ala Ala Ser Pro Lys Cys Ile Met Lys Glu Lys Lys Pro Gly Glu
        115                 120                 125

Thr Phe Phe Met Cys Ser Cys Ser Ser Asp Glu Cys Asn Asp Asn Ile
130                 135                 140

Ile Phe Ser Glu Glu Tyr
145                 150

<210> SEQ ID NO 50
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Thr Gly Gly Val Glu Cys
    130                 135                 140

Pro Pro Cys Pro Ala Pro Pro Val Ala Gly Pro Ser Val Phe Leu Phe
145                 150                 155                 160

```
Pro Pro Lys Pro Lys Asp Thr Leu Met Ile Ser Arg Thr Pro Glu Val
            165                 170                 175

Thr Cys Val Val Asp Val Ser His Glu Asp Pro Glu Val Gln Phe
        180                 185                 190

Asn Trp Tyr Val Asp Gly Val Glu Val His Asn Ala Lys Thr Lys Pro
            195                 200                 205

Arg Glu Glu Gln Phe Asn Ser Thr Phe Arg Val Val Ser Val Leu Thr
        210                 215                 220

Val Val His Gln Asp Trp Leu Asn Gly Lys Glu Tyr Lys Cys Lys Val
225                 230                 235                 240

Ser Asn Lys Gly Leu Pro Ala Pro Ile Glu Lys Thr Ile Ser Lys Thr
            245                 250                 255

Lys Gly Gln Pro Arg Glu Pro Gln Val Tyr Thr Leu Pro Pro Ser Arg
        260                 265                 270

Glu Glu Met Thr Lys Asn Gln Val Ser Leu Thr Cys Leu Val Lys Gly
            275                 280                 285

Phe Tyr Pro Ser Asp Ile Ala Val Glu Trp Glu Ser Asn Gly Gln Pro
        290                 295                 300

Glu Asn Asn Tyr Lys Thr Thr Pro Pro Met Leu Asp Ser Asp Gly Ser
305                 310                 315                 320

Phe Phe Leu Tyr Ser Lys Leu Thr Val Asp Lys Ser Arg Trp Gln Gln
            325                 330                 335

Gly Asn Val Phe Ser Cys Ser Val Met His Glu Ala Leu His Asn His
        340                 345                 350

Tyr Thr Gln Lys Ser Leu Ser Leu Ser Pro Gly Lys
        355                 360

<210> SEQ ID NO 51
<211> LENGTH: 1164
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
atggatgcaa tgaagagagg gctctgctgt gtgctgctgc tgtgtggagc agtcttcgtt      60
tcgcccggcg ccacgatccc accgcacgtt cagaagtcgg ttaataacga catgatagtc     120
actgacaaca acggtgcagt caagtttcca caactgtgta aattttgtga tgtgagattt     180
tccacctgtg acaaccagaa atcctgcatg agcaactgca gcatcacctc catctgtgag     240
aagccacagg aagtctgtgt ggctgtatgg agaagaatga cgagaacat aacactagag     300 acagtttgcc atgaccccaa gctcccctac catgacttta ttctggaaga tgctgcttct     360
ccaaagtgca ttatgaagga aaaaaaaaag cctggtgaga ctttcttcat gtgttcctgt     420
agctctgatg agtgcaatga caacatcatc ttctcagaag aatataacac cagcaatcct     480
gacaccggtg gtggagtcga gtgcccaccg tgcccagcac cacctgtggc aggaccgtca     540
gtcttcctct tccccccaaa acccaaggac accctcatga tctcccggac ccctgaggtc     600
acgtgcgtgg tggtggacgt gagccacgaa gaccccgagg tccagttcaa ctggtacgtg     660
gacggcgtgg aggtgcataa tgccaagaca aagccacggg aggagcagtt caacagcacg     720
ttccgtgtgg tcagcgtcct caccgtcgtg caccaggact ggctgaacgg caaggagtac     780
aagtgcaagg tctccaacaa aggcctccca gcccccatcg agaaaaccat ctccaaaacc     840
```

```
aaagggcagc ccgagaacc acaggtgtac accctgcccc catcccggga ggagatgacc    900
aagaaccagg tcagcctgac ctgcctggtc aaaggcttct accccagcga catcgccgtg    960
gagtgggaga gcaatgggca gccggagaac aactacaaga ccacacctcc catgctggac   1020
tccgacggct ccttcttcct ctacagcaag ctcaccgtgg acaagagcag gtggcagcag   1080
gggaacgtct tctcatgctc cgtgatgcat gaggctctgc acaaccacta cacgcagaag   1140
agcctctccc tgtctccggg taaa                                          1164
```

<210> SEQ ID NO 52
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Met Asp Ala Met Lys Arg Gly Leu Cys Cys Val Leu Leu Cys Gly
1               5                   10                  15

Ala Val Phe Val Ser Pro Gly Ala Thr Ile Pro Pro His Val Gln Lys
            20                  25                  30

Ser Val Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
    130                 135                 140

Cys Asn Asp Asn Ile Ile Phe Ser Glu Glu Tyr Asn Thr Ser Asn Pro
145                 150                 155                 160

Asp Thr Gly Gly Val Glu Cys Pro Pro Cys Pro Ala Pro Pro Val
                165                 170                 175

Ala Gly Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser
        195                 200                 205

His Glu Asp Pro Glu Val Gln Phe Asn Trp Tyr Val Asp Gly Val Glu
    210                 215                 220

Val His Asn Ala Lys Thr Lys Pro Arg Glu Glu Gln Phe Asn Ser Thr
225                 230                 235                 240

Phe Arg Val Val Ser Val Leu Thr Val Val His Gln Asp Trp Leu Asn
                245                 250                 255

Gly Lys Glu Tyr Lys Cys Lys Val Ser Asn Lys Gly Leu Pro Ala Pro
            260                 265                 270

Ile Glu Lys Thr Ile Ser Lys Thr Lys Gly Gln Pro Arg Glu Pro Gln
        275                 280                 285

Val Tyr Thr Leu Pro Pro Ser Arg Glu Glu Met Thr Lys Asn Gln Val
    290                 295                 300
```

```
Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
                325                 330                 335

Pro Met Leu Asp Ser Asp Gly Ser Phe Phe Leu Tyr Ser Lys Leu Thr
            340                 345                 350

Val Asp Lys Ser Arg Trp Gln Gln Gly Asn Val Phe Ser Cys Ser Val
        355                 360                 365

Met His Glu Ala Leu His Asn His Tyr Thr Gln Lys Ser Leu Ser Leu
370                 375                 380

Ser Pro Gly Lys
385

<210> SEQ ID NO 53
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Lys Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Thr Gly Gly Gly Val Glu Cys
    130                 135                 140

Pro Pro Cys Pro Ala Pro Pro Val Ala Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Gln Phe
            180                 185                 190

Asn Trp Tyr Val Asp Gly Val Glu Val His Asn Ala Lys Thr Lys Pro
        195                 200                 205

Arg Glu Glu Gln Phe Asn Ser Thr Phe Arg Val Val Ser Val Leu Thr
    210                 215                 220

Val Val His Gln Asp Trp Leu Asn Gly Lys Glu Tyr Lys Cys Lys Val
225                 230                 235                 240

Ser Asn Lys Gly Leu Pro Ala Pro Ile Glu Lys Thr Ile Ser Lys Thr
                245                 250                 255

Lys Gly Gln Pro Arg Glu Pro Gln Val Tyr Thr Leu Pro Pro Ser Arg
```

```
                    260                 265                 270
Glu Glu Met Thr Lys Asn Gln Val Ser Leu Thr Cys Leu Val Lys Gly
            275                 280                 285

Phe Tyr Pro Ser Asp Ile Ala Val Glu Trp Glu Ser Asn Gly Gln Pro
        290                 295                 300

Glu Asn Asn Tyr Lys Thr Thr Pro Pro Met Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
        355                 360

<210> SEQ ID NO 54
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Lys Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Thr Gly Gly Thr His Thr
    130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255
```

Lys Ala Lys Gly Gln Pro Arg Glu Pro Gln Val Tyr Thr Leu Pro Pro
            260                 265                 270

Ser Arg Glu Glu Met Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
        355                 360                 365

<210> SEQ ID NO 55
<211> LENGTH: 358
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Lys Ser Val Asn Asn Asp Met Ile Val Thr Asp Asn Asn Gly Ala
1               5                   10                  15

Val Lys Phe Pro Gln Leu Cys Lys Phe Cys Asp Val Arg Phe Ser Thr
            20                  25                  30

Cys Asp Asn Gln Lys Ser Cys Met Ser Asn Cys Ser Ile Thr Ser Ile
        35                  40                  45

Cys Glu Lys Pro Gln Glu Val Cys Val Ala Val Trp Arg Lys Asn Asp
    50                  55                  60

Glu Asn Ile Thr Leu Glu Thr Val Cys His Asp Pro Lys Leu Pro Tyr
65                  70                  75                  80

His Asp Phe Ile Leu Glu Asp Ala Ala Ser Pro Lys Cys Ile Met Lys
                85                  90                  95

Glu Lys Lys Lys Pro Gly Glu Thr Phe Phe Met Cys Ser Cys Ser Ser
            100                 105                 110

Asp Glu Cys Asn Asp Asn Ile Ile Phe Ser Glu Glu Tyr Asn Thr Ser
        115                 120                 125

Asn Pro Asp Thr Gly Gly Gly Val Glu Cys Pro Pro Cys Pro Ala Pro
    130                 135                 140

Pro Val Ala Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Gln Phe Asn Trp Tyr Val Asp Gly
            180                 185                 190

Val Glu Val His Asn Ala Lys Thr Lys Pro Arg Glu Glu Gln Phe Asn
        195                 200                 205

Ser Thr Phe Arg Val Val Ser Val Leu Thr Val His Gln Asp Trp
    210                 215                 220

Leu Asn Gly Lys Glu Tyr Lys Cys Lys Val Ser Asn Lys Gly Leu Pro
225                 230                 235                 240

Ala Pro Ile Glu Lys Thr Ile Ser Lys Thr Lys Gly Gln Pro Arg Glu
                245                 250                 255

```
Pro Gln Val Tyr Thr Leu Pro Pro Ser Arg Glu Glu Met Thr Lys Asn
                260                 265                 270

Gln Val Ser Leu Thr Cys Leu Val Lys Gly Phe Tyr Pro Ser Asp Ile
            275                 280                 285

Ala Val Glu Trp Glu Ser Asn Gly Gln Pro Glu Asn Asn Tyr Lys Thr
        290                 295                 300

Thr Pro Pro Met Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
            355

<210> SEQ ID NO 56
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Lys Ser Val Asn Asn Asp Met Ile Val Thr Asp Asn Asn Gly Ala
1               5                   10                  15

Val Lys Phe Pro Gln Leu Cys Lys Phe Cys Asp Val Arg Phe Ser Thr
            20                  25                  30

Cys Asp Asn Gln Lys Ser Cys Met Ser Asn Cys Ser Ile Thr Ser Ile
        35                  40                  45

Cys Glu Lys Pro Gln Glu Val Cys Val Ala Val Trp Arg Lys Asn Asp
    50                  55                  60

Glu Asn Ile Thr Leu Glu Thr Val Cys His Asp Pro Lys Leu Pro Tyr
65                  70                  75                  80

His Asp Phe Ile Leu Glu Asp Ala Ala Ser Pro Lys Cys Ile Met Lys
                85                  90                  95

Glu Lys Lys Lys Pro Gly Glu Thr Phe Phe Met Cys Ser Cys Ser Ser
            100                 105                 110

Asp Glu Cys Asn Asp Asn Ile Ile Phe Ser Glu Glu Tyr Asn Thr Ser
        115                 120                 125

Asn Pro Asp Thr Gly Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
```

```
                    245                 250                 255
Arg Glu Pro Gln Val Tyr Thr Leu Pro Pro Ser Arg Glu Glu Met Thr
                260                 265                 270

Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
        290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
            355                 360

<210> SEQ ID NO 57
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Met Ile Val Thr Asp Asn Asn Gly Ala Val Lys Phe Pro Gln Leu
1               5                   10                  15

Cys Lys Phe Cys Asp Val Arg Phe Ser Thr Cys Asp Asn Gln Lys Ser
            20                  25                  30

Cys Met Ser Asn Cys Ser Ile Thr Ser Ile Cys Glu Lys Pro Gln Glu
        35                  40                  45

Val Cys Val Ala Val Trp Arg Lys Asn Asp Glu Asn Ile Thr Leu Glu
    50                  55                  60

Thr Val Cys His Asp Pro Lys Leu Pro Tyr His Asp Phe Ile Leu Glu
65                  70                  75                  80

Asp Ala Ala Ser Pro Lys Cys Ile Met Lys Glu Lys Lys Lys Pro Gly
                85                  90                  95

Glu Thr Phe Phe Met Cys Ser Cys Ser Ser Asp Glu Cys Asn Asp Asn
            100                 105                 110

Ile Ile Phe Ser Glu Glu Tyr Asn Thr Ser Asn Pro Asp Thr Gly Gly
        115                 120                 125

Gly Val Glu Cys Pro Pro Cys Pro Ala Pro Val Ala Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Phe Arg Val Val
        195                 200                 205

Ser Val Leu Thr Val Val His Gln Asp Trp Leu Asn Gly Lys Glu Tyr
    210                 215                 220

Lys Cys Lys Val Ser Asn Lys Gly Leu Pro Ala Pro Ile Glu Lys Thr
225                 230                 235                 240
```

```
Ile Ser Lys Thr Lys Gly Gln Pro Arg Glu Pro Gln Val Tyr Thr Leu
            245                 250                 255

Pro Pro Ser Arg Glu Glu Met Thr Lys Asn Gln Val Ser Leu Thr Cys
        260                 265                 270

Leu Val Lys Gly Phe Tyr Pro Ser Asp Ile Ala Val Glu Trp Glu Ser
            275                 280                 285

Asn Gly Gln Pro Glu Asn Asn Tyr Lys Thr Thr Pro Pro Met Leu Asp
        290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350
```

<210> SEQ ID NO 58
<211> LENGTH: 354
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Asp Met Ile Val Thr Asp Asn Asn Gly Ala Val Lys Phe Pro Gln Leu
1               5                   10                  15

Cys Lys Phe Cys Asp Val Arg Phe Ser Thr Cys Asp Asn Gln Lys Ser
            20                  25                  30

Cys Met Ser Asn Cys Ser Ile Thr Ser Ile Cys Glu Lys Pro Gln Glu
        35                  40                  45

Val Cys Val Ala Val Trp Arg Lys Asn Asp Glu Asn Ile Thr Leu Glu
    50                  55                  60

Thr Val Cys His Asp Pro Lys Leu Pro Tyr His Asp Phe Ile Leu Glu
65                  70                  75                  80

Asp Ala Ala Ser Pro Lys Cys Ile Met Lys Glu Lys Lys Lys Pro Gly
                85                  90                  95

Glu Thr Phe Phe Met Cys Ser Cys Ser Ser Asp Glu Cys Asn Asp Asn
            100                 105                 110

Ile Ile Phe Ser Glu Glu Tyr Asn Thr Ser Asn Pro Asp Thr Gly Gly
        115                 120                 125

Gly Thr His Thr Cys Pro Pro Cys Pro Ala Pro Glu Leu Leu Gly Gly
    130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255
```

Thr Leu Pro Pro Ser Arg Glu Met Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys

<210> SEQ ID NO 59
<211> LENGTH: 358
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Thr Gly Gly Gly Val Glu Cys Pro Pro Cys Pro Ala Pro
    130                 135                 140

Pro Val Ala Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Gln Phe Asn Trp Tyr Val Asp Gly
            180                 185                 190

Val Glu Val His Asn Ala Lys Thr Lys Pro Arg Glu Glu Gln Phe Asn
        195                 200                 205

Ser Thr Phe Arg Val Val Ser Val Leu Thr Val Val His Gln Asp Trp
    210                 215                 220

Leu Asn Gly Lys Glu Tyr Lys Cys Lys Val Ser Asn Lys Gly Leu Pro
225                 230                 235                 240

Ala Pro Ile Glu Lys Thr Ile Ser Lys Thr Lys Gly Gln Pro Arg Glu
                245                 250                 255

```
Pro Gln Val Tyr Thr Leu Pro Pro Ser Arg Glu Glu Met Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Met Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
            355

<210> SEQ ID NO 60
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Thr Gly Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
```

```
                245                 250                 255
Arg Glu Pro Gln Val Tyr Thr Leu Pro Pro Ser Arg Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
            355                 360

<210> SEQ ID NO 61
<211> LENGTH: 358
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asp
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Thr Gly Gly Gly Val Glu Cys Pro Cys Pro Ala Pro
    130                 135                 140

Pro Val Ala Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Gln Phe Asn Trp Tyr Val Asp Gly
            180                 185                 190

Val Glu Val His Asn Ala Lys Thr Lys Pro Arg Glu Glu Gln Phe Asn
        195                 200                 205

Ser Thr Phe Arg Val Val Ser Val Leu Thr Val Val His Gln Asp Trp
    210                 215                 220

Leu Asn Gly Lys Glu Tyr Lys Cys Lys Val Ser Asn Lys Gly Leu Pro
225                 230                 235                 240
```

```
Ala Pro Ile Glu Lys Thr Ile Ser Lys Thr Lys Gly Gln Pro Arg Glu
            245                 250                 255

Pro Gln Val Tyr Thr Leu Pro Pro Ser Arg Glu Glu Met Thr Lys Asn
        260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
        290                 295                 300

Thr Pro Pro Met Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
            325                 330                 335

Ser Val Met His Glu Ala Leu His Asn His Tyr Thr Gln Lys Ser Leu
            340                 345                 350

Ser Leu Ser Pro Gly Lys
            355

<210> SEQ ID NO 62
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asp
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
            85                  90                  95

Pro Lys Cys Ile Met Lys Glu Lys Lys Pro Gly Glu Thr Phe Phe
        100                 105                 110

Met Cys Ser Cys Ser Ser Asp Glu Cys Asn Asp Asn Ile Ile Phe Ser
        115                 120                 125

Glu Glu Tyr Thr Gly Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
            165                 170                 175

Val Asp Val Ser His Glu Asp Pro Glu Val Lys Phe Asn Trp Tyr Val
        180                 185                 190

Asp Gly Val Glu Val His Asn Ala Lys Thr Lys Pro Arg Glu Glu Gln
    195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240
```

```
Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 63

His His His His His His
1               5

<210> SEQ ID NO 64
<211> LENGTH: 38
<212> TYPE: PRT
<213> ORGANISM: Homo sapiens

<400> SEQUENCE: 64

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val
        35

<210> SEQ ID NO 65
<211> LENGTH: 16
<212> TYPE: PRT
<213> ORGANISM: Homo sapiens

<400> SEQUENCE: 65

Thr Ile Pro Pro His Val Gln Lys Ser Val Asn Asn Asp Met Ile Val
1               5                   10                  15

<210> SEQ ID NO 66
<211> LENGTH: 10
<212> TYPE: PRT
<213> ORGANISM: Homo sapiens

<400> SEQUENCE: 66

Gln Lys Ser Val Asn Asn Asp Met Ile Val
1               5                   10
```

-continued

```
<210> SEQ ID NO 67
<211> LENGTH: 4
<212> TYPE: PRT
<213> ORGANISM: Homo sapiens

<400> SEQUENCE: 67

Asp Met Ile Val
1

<210> SEQ ID NO 68
<211> LENGTH: 63
<212> TYPE: PRT
<213> ORGANISM: Homo sapiens

<400> SEQUENCE: 68

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
            20                  25                  30

Val Glu Met Glu Ala Gln Lys Asp Glu Ile Ile Cys Pro Ser Cys Asn
        35                  40                  45

Arg Thr Ala His Pro Leu Arg His Ile Asn Asn Asp Met Ile Val
    50                  55                  60

<210> SEQ ID NO 69
<211> LENGTH: 41
<212> TYPE: PRT
<213> ORGANISM: Homo sapiens

<400> SEQUENCE: 69

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val
        35                  40
```